United States Patent
Romagne et al.

(10) Patent No.: US 10,253,095 B2
(45) Date of Patent: Apr. 9, 2019

(54) ANTI-KIR COMBINATION TREATMENTS AND METHODS

(75) Inventors: Francois Romagne, Marseille (FR); Peter Andreas Nicolai Reumert Wagtmann, Rungsted Kyst (DK); Joakim Glamann, Gentofte (DK)

(73) Assignees: INNATE PHARMA S.A.S., Marseilles (FR); NOVO NORDISK A/S, Bagsvaerd (DK)

( * ) Notice: Subject to any disclaimer, the term of this patent is extended or adjusted under 35 U.S.C. 154(b) by 0 days.

(21) Appl. No.: 13/183,602

(22) Filed: Jul. 15, 2011

(65) Prior Publication Data

US 2011/0293561 A1 Dec. 1, 2011

Related U.S. Application Data

(63) Continuation of application No. 11/813,363, filed as application No. PCT/EP2006/050072 on Jan. 6, 2006, now abandoned.

(60) Provisional application No. 60/642,128, filed on Jan. 8, 2005.

(30) Foreign Application Priority Data

Jan. 6, 2005 (DK) ................. 2005 00026

(51) Int. Cl.
  *C07K 16/28* (2006.01)
  *A61K 39/395* (2006.01)
  *A61K 38/20* (2006.01)
  *A61K 39/00* (2006.01)

(52) U.S. Cl.
  CPC ...... *C07K 16/2803* (2013.01); *A61K 38/2013* (2013.01); *A61K 2039/505* (2013.01)

(58) Field of Classification Search
  CPC . C07K 14/55; C07K 16/2803; A61K 38/2013
  See application file for complete search history.

(56) References Cited

U.S. PATENT DOCUMENTS

| | | | | |
|---|---|---|---|---|
| 7,803,376 B2* | 9/2010 | Velardi | ........... | C07K 16/28 424/144.1 |
| 8,119,775 B2* | 2/2012 | Moretta | ........... | C07K 16/2803 530/388.15 |
| 8,222,376 B2* | 7/2012 | Padkjaer | ........... | C07K 16/2803 424/153.1 |
| 8,388,970 B2* | 3/2013 | Padkjaer | ........... | C07K 16/2803 424/142.1 |
| 8,637,258 B2* | 1/2014 | Padkjaer | ........... | C07K 16/2803 435/7.1 |
| 8,709,411 B2* | 4/2014 | Farag | ........... | A61K 31/4439 424/130.1 |
| 8,981,065 B2* | 3/2015 | Moretta | ........... | C07K 16/2803 530/388.15 |
| 9,067,997 B2* | 6/2015 | Romagne | ........... | C07K 16/2803 |
| 9,090,876 B2* | 7/2015 | Velardi | ........... | C07K 16/28 |
| 9,415,104 B2* | 8/2016 | Farag | ........... | A61K 31/4439 |
| 9,844,593 B2* | 12/2017 | Andre | ........... | A61K 39/3955 |
| 2005/0037002 A1* | 2/2005 | Velardi | ........... | C07K 16/28 424/143.1 |
| 2006/0280740 A1 | 12/2006 | Padkjaer et al. | | |
| 2007/0178106 A1* | 8/2007 | Romagne | ........... | C07K 16/2803 424/155.1 |
| 2008/0305117 A1 | 12/2008 | Padkjaer et al. | | |
| 2009/0075340 A1 | 3/2009 | Padkjaer et al. | | |
| 2009/0081240 A1 | 3/2009 | Moretta et al. | | |
| 2009/0191213 A9 | 7/2009 | Padkjaer et al. | | |
| 2010/0189723 A1* | 7/2010 | Wagtmann et al. | ....... | 424/173.1 |
| 2011/0293561 A1* | 12/2011 | Romagne | ........... | A61K 38/2013 424/85.2 |
| 2012/0208237 A1* | 8/2012 | Moretta | ........... | C07K 16/2803 435/69.6 |
| 2012/0328615 A1* | 12/2012 | Romagne | ........... | C07K 16/2803 424/135.1 |
| 2013/0251711 A1* | 9/2013 | Andre | ........... | A61K 39/3955 424/133.1 |
| 2013/0287770 A1* | 10/2013 | Moretta | ........... | C07K 16/2803 424/133.1 |
| 2015/0191547 A1* | 7/2015 | Moretta | ........... | C07K 16/2803 424/131.1 |
| 2015/0197569 A1* | 7/2015 | Wagtmann | ....... | A61K 39/39541 424/172.1 |
| 2015/0299319 A1* | 10/2015 | Velardi | ........... | C07K 16/28 424/133.1 |
| 2015/0344576 A1* | 12/2015 | Moretta | ........... | C07K 16/2803 424/139.1 |

(Continued)

FOREIGN PATENT DOCUMENTS

| JP | 2008-500947 | 1/2008 |
|---|---|---|
| WO | WO 2004/003019 | 1/2001 |

(Continued)

OTHER PUBLICATIONS

ATCC website search , "1-7F9"; p. 1; May 30, 2012.*
Berenbaum (Clin. Exp. Immunol. 28:1-18 (1977)).*
Berenbaum (Pharmacol. Rev. 41:93-141 (1989)).*
Tallarida "Drug Synergism and Dose Effect Analysis" Ed. Chapman & Hall ((2000), pp. 1-8, 10-13 and 57-71).*
Benson DM Jr, et al., Blood. Nov. 2012;120(22):4324-33. doi: 10.1182/blood-2012-06-438028. Epub Oct. 1, 2012.*
Vey N, et al., Blood. Nov. 22, 2012;120(22):4317-23. doi: 10.1182/blood-2012-06-437558. Epub Sep. 21, 2012.*
Benson DM Jr, et al., Blood. Dec. 8, 2011;118(24):6387-91. doi: 10.1182/blood-2011-06-360255. Epub Oct. 26, 2011.*

(Continued)

*Primary Examiner* — Jessica H Roark
(74) *Attorney, Agent, or Firm* — Robin L. Teskin; LeClairRyan PLLC

(57) ABSTRACT

Compositions comprising anti-KIR antibodies and one or more secondary anti-cancer agents or anti-viral agents and methods of using such combinations (as combination compositions or in separate administration protocols) in the treatment of cancers (e.g., lung cancer) or viral infection (e.g., HIV or HCV infection) are provided.

7 Claims, 5 Drawing Sheets

Specification includes a Sequence Listing.

(56) References Cited

U.S. PATENT DOCUMENTS

2015/0376275 A1* 12/2015 Romagne ............ C07K 16/2803
424/135.1

FOREIGN PATENT DOCUMENTS

| WO | WO 2005/009465 | 7/2004 | |
|---|---|---|---|
| WO | WO-2004056392 A1 * | 7/2004 | ............ A61K 38/20 |
| WO | WO 2005/003168 | 1/2005 | |
| WO | WO 2005/003172 | 1/2005 | |
| WO | WO-2006003179 A2 * | 1/2006 | ......... C07K 16/2803 |
| WO | 2006/072625 | 7/2006 | |
| WO | WO-2006072626 A1 * | 7/2006 | ......... C07K 16/2803 |

OTHER PUBLICATIONS

Medilexicon definition for "potentiation"; pp. 1-2; Dec. 16, 2015.*
Benson et al. (Blood 2011;118(24):6387-6391).*
Kohrt et al. (Blood. 2014;123(5):678-686).*
Knorr et al., Seminars in Immunology 26 (2014) 161-172).*
George et al. (Circulation. 1998; 97: 900-906).*
Vahlne et al., Eur. J. Immunol. 40:813-823 (Year: 2010).*
Farag et al., Clin. Cancer Res. 8:2812-19 (Year: 2002).*
Rigel & Carucci, CA Cancer J Clin, 50:215-236 (Year: 2000).*
European Search Reported for Application No. 11181366.3-2406 dated Apr. 2, 2012.
Brady, (2004), J Immunol., 172:2048-2058.
Vivier, (2004), Nature Review, 4:190-197.
Abi-Rached, L. and Parham, P., "Natural selection drives recurrent formation of activating killer cell immunoglobulin-like receptor and Ly49 from inhibitory homologues", JEM; The Rockefeller University Press, 2005; 201(8):1319-1332.
Foa, R., "IL2 treatment for cancer: from biology to gene therapy", Br J Cancer 1992; 66:992-998.
Gluck, W., et al., "Phase I Studies of Interleukin (IL)-2 and Rituximab in B-Cell Non-Hodgkin's Lymphoma: IL-2 Mediated Natural Killer Cell Expansion Correlations with Clinical Response", Clin Cancer Res 2004; 10:2253-2264. Published online Apr. 8, 2004.
Grande, C., et al., "Interleukin-2 for the treatment of solid tumors other than melanoma and renal cell carcinoma", Anti-Cancer Drugs 2006, 17:1-12.
Hooijberg, E., et al., "Eradication of Large Human B Cell Tumors in Nude Mice with Unconjugated CD20 Monoclonal Antibodies and Interleukin 2", Cancer Res. 1995, 55:2627-2634.
McQueen, K. and Parham, P., "Variable receptors controlling activation and inhibition of NK cells", Current Opinion in Immunology 2002; 14:615-621.
Minton, K., "Down the Drain?" Nature Reviews Cancer, Jul. 2003, vol. 3, No. 7, p. 472-473.
Ruggeri, L., et al., "Effectiveness of Donor Natural Killer Cell Alloreactivity in Mismatched Hematopoietic Transplants", Science, 2002; 295:2097-2100.
Tahara, H., "Therapy of digestive system cancer with use of cytokine" Cytokine and Pathology, 6th, G.I. Research, Oct. 2001, vol. 9, No. 5, p. 448-455.
English language translation of Tahara et al. (Cite No. 9) Excerpts.
Yamada, S., "Induction of systemic and therapeutic anti-tumor immunity using systemic administration of IL-2 selective agonist", Medical Proceedings of Gifu University, Mar. 31, 2003, vol. 51, No. 1, p. 176-181.
Farag, S. et al. "New Directions in Natural Killer Cell-Based Immunotherapy of Human Cancer" Expert Opinion Biological Therapy, 2003, pp. 237-250, vol. 3, No. 2.
Kogure, T. et al. "Killer-Cell Inhibitory Receptors, CD158a/b, are Upregulated by Interleukin-2, but not Interferon-γ or interleukin-4" Mediators of Inflammation, 1999, pp. 313-318, vol. 8, No. 6.
Koh, C. et al. "Augmentation of antitumor effects by NK cell inhibitory receptor blockade in vitro and in vivo" Blood, May 15, 2001, pp. 3132-3137, vol. 97, No. 10.
Koh, C. et al. "NK Inhibitory-Receptor Blockade for Purging of Leukemia: Effects on Hematopoietic Reconstitution" Biology of Blood and Marrow Transplantation, 2002, pp. 17-25, vol. 8, No. 1.
Radaev, S. et al. "Structure and Function of Natural Killer Cell Surface Receptors" Annual Review of Biophysics & Biomolecular Structure, 2003, pp. 93-114, vol. 32.
Shin, J. et al. "Monoclonal Antibodies with Various Reactivity to p58 Killer Inhibitory Receptors" Hybridoma, Nov. 6, 1999, pp. 521-527, vol. 18, No. 6.
Sondel, P. et al. "Combination Therapy with Interleukin-2 and Antitumor Monoclonal Antibodies" The Cancer Journal from Scientific American, 1997, pp. S121-S127, vol. 3, Sup. 1.
Spaggiari, G. et al. "Soluble HLA class I induces NK cell apoptosis upon the engagement of killer-activating HLA class I receptors through FasL-Fas interaction" Blood, 2002, pp. 4098-4107, vol. 100, No. 12.
Spaggiari, G. et al. "Soluble HLA class I molecules induce natural killer cell apoptosis through the engagement of CD8: evidence for a negative regulation exerted by members of the inhibitory receptor superfamily" Blood, 2006, p. 1706-1714, vol. 99, No. 5.
Thurber, G. et al. "Antibody tumor penetration: Transport opposed by systemic and antigen-mediated clearance" Advanced Drug Delivery Reviews, 2008, pp. 1421-1434, vol. 60.
Rudnick, S. et al. "Affinity and Avidity in Antibody-Based Tumor Targeting" Cancer Biotherapy and Radiopharmaceuticals, 2009, pp. 155-162, vol. 24, No. 2.
Cespedes, M. et al. "Mouse models in oncogenesis and cancer therapy" Clinical and Translational Oncology, 2006, pp. 318-329, vol. 8, No. 5.
Talmadge, J. et al. "Murine Models to Evaluate Novel and Conventional Therapeutic Strategies for Cancer" The American Journal of Pathology, Mar. 2007, pp. 793-804, vol. 170, No. 3.
Fujimori, K. et al. "A Modeling Analysis of Monoclonal Antibody Percolation Through Tumors: A Binding-Site Barrier" Journal of Nuclear Medicine, 1990, pp. 1191-1198, vol. 31.
Beckman, R. et al. "Antibody Constructs in Cancer Therapy— Protein Engineering Strategies to Improve Exposure in Solid Tumors" Cancer, Jan. 15, 2007, pp. 170-179, vol. 109, No. 2.
Fundamental Immunology (William E. Paul, M.D. ed., 3$^{rd}$ Edition, 1993, p. 242).
Romagne, F. et al. "Preclinical characterization of 1-7F9, a novel human anti-KIR receptor therapeutic antibody that augments natural killer-mediated killing of tumor cells" Blood, Sep. 2009, pp. 2667-2677, vol. 114, No. 13.
Voskoglou-Nomikos, T. et al. "Clinical Predictive Value of the in Vitro Cell Line, Human Xenograft, and Mouse Allograft Preclinical Cancer Models" Clinical Cancer Research, Sep. 15, 2003, pp. 4227-4237, vol. 9.
Dennis, C. "Off by a whisker" Nature, 2006, pp. 739-741, vol. 442.
Vajdos, F. et al. "Comprehensive Functional Maps of the Antigen-binding Site of an Anti-erbB2 Antibody Obtained with Shotgun Scanning Mutagenesis" Journal of Molecular Biology, 2002, pp. 415-428, vol. 320, No. 2.
Maccallum, R. et al. "Antibody-antigen Interactions: Contact Analysis and Binding Site Topography" Journal of Molecular Biology, 1996, pp. 732-745, vol. 262.
De Pascalis, R. et al. "Grafting of 'Abbreviated' Complementarity-Determining Regions Containing Specificity-Determining Residues Essential for Ligand Contact to Engineer a Less Immunogenic Humanized Monoclonal Antibody" The Journal of Immunology, 2002, pp. 3076-3084, vol. 169.
Casset, F. et al. "A peptide mimetic of an anti-CD4 monoclonal antibody by rational design" Biochemical and Biophysical Research Communications, 2003, pp. 198-205, vol. 307.
Holm, P. et al. "Functional mapping and single chain construction of the anti-cytokeratin 8 monoclonal antibody TS1" Molecular Immunology, 2007, pp. 1075-1084, vol. 44.
Chen, Y. et al. "Selection and Analysis of an Optimized Anti-VEGF Antibody: Crystal Structure of an Affinity-matured Fab in Complex with Antigen" Journal of Molecular Biology, 1999, pp. 865-881, vol. 293.

(56) References Cited

OTHER PUBLICATIONS

Wu, H. et al. "Humanization of a Murine Monoclonal Antibody by Simultaneous Optimization of Framework and CDR Residues" *Journal of Molecular Biology*, 1999, pp. 151-162, vol. 294.

Ward, E. et al. "Binding activities of a repertoire of single immunoglobulin variable domains secreted from *Escherichia coli*" *Nature*, 1989, pp. 544-546, vol. 341.

Smith-Gill, S. et al. "Contributions of Immunoglobulin Heavy and Light Chains to Antibody Specificity for Lysozyme and Two Haptens" *The Journal of Immunology*, 1987, pp. 4135-4144, vol. 139.

Kumar, S. et al. "Molecular Cloning and Expression of the Fabs of Human Autoantibodies in *Escherichia coli*" *The Journal of Biological Chemistry*, Nov. 2000, pp. 35129-35136, vol. 275.

Song, M. et al. "Light Chain of Natural Antibody Plays a Dominant Role in Protein Antigen Binding" *Biochemical and Biophysical Research Communications*, 2000, pp. 390-394, vol. 268.

Brummell, D. et al. "Probing the combining site of an anti-carbohydrate antibody by saturation-mutagenesis: role of the heavy-chain CDR3 residues" *Biochemistry*, Feb. 2, 1993, pp. 1180-1187, vol. 32, No. 4.

Kobayashi, H. et al. "Tryptophan H33 plays an important role in pyrimidine (6-4) pyrimidone photoproduct binding by a high-affinity antibody" *Protein Engineering*, 1999, pp. 878-884, vol. 12, No. 10.

Burks, E. et al. "In vitro scanning saturation mutagenesis of an antibody binding pocket" *Proceedings of the National Academy of Sciences*, Jan. 1997, pp. 412-417, vol. 94.

Jang, Y. et al. "The structural basis for DNA binding by an anti-DNA autoantibody" *Molecular Immunology*, 1998, pp. 1207-1217, vol. 35.

Brorson, K. et al. "Mutational Analysis of Avidity and Fine Specificity of Anti-Levan Antibodies" *The Journal of Immunology*, 1999, pp. 6694-6701, vol. 163.

Colman, P. "Effects of amino acid sequence changes on antibody-antigen interactions" *Research in Immunology*, 1994, pp. 33-36, vol. 145.

Dufner, P. et al. "Harnessing phage and ribosome display for antibody optimisation" *Trends in Biochemistry*, 2006, pp. 523-529, vol. 24, No. 11.

Moretta A, et al. "P58 molecules as putative receptors for major histocompatibility complex (MHC) class I molecules in human natural killer (NK) cells. Anti-p58 antibodies reconstitute lysis of MHC class I-protected cells in NK clones displaying different specificities." J Exp Med. Aug. 1, 1993;178(2):597-604.

Cambiaggi A, et al. "Natural killer cell acceptance of H-2 mismatch bone marrow grafts in transgenic mice expressing HLA-Cw3 specific killer cell inhibitory receptor." Proc Natl Acad Sci U S A. Jul. 22, 1997;94(15):8088-92.

\* cited by examiner

FIGURE 3A

```
                                  1                                                      50
DF-200 light variable        (1)  M--ESQTLVF SILLWF YCADGNTVMTQSPKSMSMSVGERVT TCKASEN
PAN2D-Light-variable         (1)  MDFQVQIFSF LLISASV IMSRGTVMTQSPASMSASLGERVTMTCTASSS
          Consensus          (1)           Q    FI I  L A GNIVLTQSP SMS SLGERVTLTC AS 51                                                     100
DF-200 light variable       (49)  VVT-YVSWYQQKPEQSPKLLIYGASNRYTGVPDRF TGSGSATDF TLTISS
PAN2D-Light-variable        (51)  VSSSYLYWYQQKPGSSPKLWIYSTSNLASGVPARFSGSGSGTSYSLTISS
          Consensus         (51)  V S YL WYQQKP SPKL IY  SN  SGVP RFSGSGSAT FSLTISS 101                              131
DF-200 light variable       (98)  MQAEDLADYHCGQGYSYPYTFGGGTKLEIKR
PAN2D-Light-variable       (101)  MEAEDAATYCHQYHRSPPTFGGGTKLEIKR
          Consensus        (101)  M AED A YHC Q H P TFGGGTKLEIKR
```

FIGURE 3B

```
DF-200 light variable       (44)  KASENVT-YVS         (SEQ ID NO.3)
PAN2D-Light-variable        (46)  TASSSVSSSYLY        (SEQ ID NO.4)
          Consensus               AS   V S  YL
```

FIGURE 3C

```
DF-200 light variable       (70)  GASNRYT             (SEQ ID NO.5)
PAN2D-Light-variable        (73)  STSNLAS             (SEQ ID NO.6)
          Consensus               SN  S
```

FIGURE 3D

```
DF-200 light variable      (109)  GQGYSYPYT           (SEQ ID NO.7)
PAN2D-Light-variable       (112)  HQYHRSPPT           (SEQ ID NO.8)
          Consensus                Q H  PT
```

MAVLGLLFCLVTFPSCVLS

QVQLEQSGPGLVQPSQSLSITCTVS<u>GFSFTPYGVH</u>WVRQSPGKGLEWLG<u>VIWSGGNTDY
NAAFIS</u>RLSINKDNSKSQVFFKMNSLQVNDTAIYYCAR<u>NPRPGNYPYGMDY</u>WGQGTSVT
VSS (SEQ ID NO:9)

FIGURE 4B

GFSFTPYGVH (SEQ ID NO:10)

FIGURE 4C

VIWSGGNTDYNAAFIS (SEQ ID NO:11)

FIGURE 4D

NPRPGNYPYGMDY (SEQ ID NO:12)

1-7F9 VL and VH

FIGURE 5A

EIVLTQSPVTLSLSPGERATLSCRASQSVSSYLAWYQQKPGQAPRLLIYDASNRAT
GIPARFSGSGSGTDFTLTISSLEPEDFAVYYCQQRSNWMYTFGQGTKLEIKRT
(SEQ ID NO:13)

FIGURE 5B

Gaaattgtgttgacacagtctccagtcaccctgtctttgtctccaggggaaagagccaccctctcctgcagggccagtc
agagtgttagcagctacttagcctggtaccaacagaaacctggccaggctcccaggctcctcatctatgatgcatcca
acagggccactggcatcccagccaggttcagtggcagtgggtctgggacagacttcactctcaccatcagcagccta
gagcctgaagattttgcagtttattattgtcagcagcgtagcaactggatgtacacttttggccaggggaccaagctgga
gatcaaacgaact (SEQ ID NO:14)

FIGURE 5C

QVQLVQSGAEVKKPGSSVKVSCKASGGTFSFYAISWVRQAPGQGLEWMGGFIPIF
GAANYAQKFQGRVTITADESTSTAYMELSSLRSDDTAVYYCARIPSGSYYYDYDMD
VWGQGTTVTVSS (SEQ ID NO:15)

FIGURE 5D

Caggtccagctggtgcagtctggggctgaggtgaagaagcctgggtcctcggtgaaggtctcctgcaaggcttctgg
aggcaccttcagtttctatgctatcagctgggtgcgacaggcccctggacaagggcttgagtggatgggagggttcat
ccctatctttggtgcagcaaactacgcacagaagttccagggcagagtcacgattaccgcggacgaatccacgagc
acagcctacatggaactgagcagcctgagatctgacgacacggccgtgtattactgtgcgagaatccctagtgggag
ctactactacgactacgatatggacgtctggggccaagggaccacggtcaccgtctcctca (SEQ ID NO:16)

ANTI-KIR COMBINATION TREATMENTS AND METHODS

CROSS REFERENCE TO RELATED APPLICATIONS

This application is a continuation of U.S. application Ser. No. 11/813,363, filed May 21, 2008, which is the U.S. national stage application of International Patent Application No. PCT/EP2006/050072, filed Jan. 6, 2006, which claimed priority of Danish Patent Application PA 2005 00026, filed Jan. 6, 2005; this application further claims priority under 35 U.S.C. § 119 of U.S. Provisional Application 60/642,128, filed Jan. 7, 2005.

FIELD OF THE INVENTION

This invention relates to the treatment of cancer and pre-cancerous conditions or viral infections wherein an antibody against a killer immunoglobulin-like receptor (KIR) is employed in combination with other cancer or cancer preventive treatments or anti-viral treatments.

BACKGROUND OF THE INVENTION

Natural killer (NK) cells are a subset of large granular lymphocytes that act as cyto-toxic immune cells. NK cells can be identified by any number of known cell surface markers which vary between species (e.g., in humans CD56, CD16, NKp44, NKp46, and NKp30 are often used; in mice NK1.1, Ly49A-W, CD49b are often used). In an active state, NK cells are capable of killing certain autologous, allogeneic, and even xenogeneic tumor cells, virus-infected cells, certain bacteria (e.g., *Salmonella typhi*), and other target cells. NK cells appear to preferentially kill target cells that express little or no Major Histocompatibility Class I ("MHCI" or "MHC-I") molecules on their surface. NK cells also kill target cells to which antibody molecules have attached, a mechanism known as antibody-dependent cellular cytotoxicity (ADCC). In action against target cells, NK cells can release pore-forming proteins called perforins, proteolytic enzymes called granzymes, and cytokines/chemokines (e.g., TNFα, IFNγ, etc.) that directly lead to target cell apoptosis or lysis, or that regulate other immune responses. Upon activation, NK cells also may express Fas ligand (FasL), enabling these cells to induce apoptosis in cells that express Fas.

Sufficient NK cell activity and NK cell count typically are both necessary to mounting an adequate NK cell-mediated immune response. NK cells may be present in normal numbers in an individual, but if not activated these cells will be ineffective in performing vital immune system functions, such as eliminating abnormal cells. Decreased NK cell activity is linked to the development and progression of many diseases. For example, research has demonstrated that low NK cell activity causes greater susceptibility to diseases such as chronic fatigue syndrome (CFS), viral infections, and the development of cancers.

NK cell activity is regulated by NK cell activity-modulating receptors ("NKCAMRs" or simply "AMRs"), which may be specific for various ligands such as MHC-I molecules, MHC-I homologs, or other biological molecules expressed on target cells. NK cells in an individual typically present a number of activating and inhibitory receptors. The activity of NK cells is regulated by a balance of signals transduced through these activating and inhibitory receptors. Each type of NKCAMR is briefly discussed in turn below.

When somatic cells are either under stress, such in cancer progression or are infected, various molecules, such as MICA and MICB, are typically displayed on the surface of the stressed cells and normally displayed MHC-I molecules are "lost" from the cell surface (reduced in number and/or glycosylated such that they are not "seen" as "foreign" by the immune system). NKCAMRs are sensitive to these and other changes in potential NK target cells associated with cellular stress, disease, and disorder.

Most NKCAMRs appear to belong to one of two classes of proteins: the immunoglobulin (Ig)-like receptor superfamily (IgSF) or the C-type lectin-like receptor (CTLR) super family (see, e.g., Radaev and Sun, Annu. Rev. Biomol. Struct. 2003 32:93-114). However, other forms of NKCAMRs are known. The structures of a number of NKCAMRs have been elucidated (Id.). To better illustrate the invention, types of well understood NKCAMRs, with reference to particular examples thereof, are described here. However, several additional NKCAMRs are known besides those receptors explicitly described here (see, e.g., Farag et al., Expert Opin. Biol. Ther. 3(2):237-250) and the inventive compositions and methods described herein typically will also be applicable to these and other NKCAMRs.

NK Cell Activating Receptors (NKCARs)

Many NK cell activating receptors (NKCARs) belong to the Ig superfamily (IgSF) (such receptors also may be referred to as Ig-like receptors or "ILRs" herein). Activating ILR NK receptors (AILRs) include, e.g., CD2, CD16, CD69, DNAX accessory molecule-1 (DNAM-1), 2B4, NK1.1; killer immunoglobulin (Ig)-like activating receptors (KARs); ILTs/LIRs; and natural cytotoxicity receptors (NCRs) such as NKp44, NKp46, and NKp30. Several other NKCARs belong to the CLTR superfamily (e.g., NKRP-1, CD69; CD94/NKG2C and CD94/NKG2E heterodimers, NKG2D homodimer, and in mice, activating isoforms of Ly49 (such as Ly49A-D)). Still other NKCARs (e.g., LFA-1 and VLA-4) belong to the integrin protein superfamily and other activating receptors may have even other distinguishable structures. Many NKCARs possess extracellular domains that bind to MHC-I molecules, and cytoplasmic domains that are relatively short and lack the inhibitory (ITIM) signaling motifs characteristic of inhibitory NK receptors. The transmembrane domains of these receptors typically include a charged amino acid residue that facilitates their association with signal transduction-associated molecules such as CD3zeta, FcεRIγ, DAP12, and DAP10 (2B4, for example, appears to be an exception to this general rule), which contain short amino acid sequences termed an 'immunoreceptor tyrosine-based activating motif' (ITAMs) that propagate NK cell-activating signals. Receptor 2B4 contains 4 so-called ITSM motifs (Immunoreceptor Tyrosine-based Switch Motif) in its cytoplasmic tail; ITSM motifs can also be found in NKCARs CS1/CRACC and NTB-A. The cytoplasmic domains of 2B4 and SLAM contain two or more unique tyrosine-based motifs that resemble motifs presents in activating and inhibitory receptors and can recruit the SH2-domain containing proteins SHP-2 and SAP (SLAM-associated protein).

Stress-induced molecules, such as MIC-A, MIC-B, and ULBPs in humans, and Rae-1 and H-60 in mice, can serve as ligands for NKCARs, such as the NKG2D homodimer. Cellular carbohydrates, pathogenic antigens, and antibodies can also be NKCAR ligands. For example, NKR-P1 may bind to carbohydrate ligands and trigger NK cell activation, particularly against tumor cells which exhibit aberrant glycosylation patterns. Viral hemagglutinins may serve as ligands for natural cytotoxic receptors (NCRs), such as ILR NKCARs NKp30, NKp44, NKp46, and NKp80.

NKCARs can either directly transduce activating signals or can act in connection with adaptor molecules or other receptors (either in the context of a coordinated response between receptors that are sometimes singularly effective or in the context of coreceptor-receptor pairings). For example, NKCAR NCRs typically lack ITAMs and, accordingly, bind to adaptor molecules through a charged residue in their transmembrane domains (e.g., NKp30 associates with the CD3 zeta chain; NKp44 associates with DAP12 and/or KARAP; NKp46 is coupled to the CD3 zeta chain and FcRIγ chain), which are, in turn, able to recruit protein tyrosine kinases (PTKs) in order to propagate NK cell-activating signals. CD16, which is a NKCAR important to NK cell-mediated ADCC and cytokine production, associates with homodimers or heterodimers formed of CD3 zeta and/or gamma chains. NKG2D appears to play a complementary and/or synergistic role with NCRs and NKCARs in NK cell activation. Activation of NK cells against particular targets may require coordinated activation of multiple NKCARs or NCRs, or only action of a single receptor. Other triggering surface molecules including 2B4 and NKp80 appear to function as coreceptors for NK cell activation.

Activating isoforms of human KIRs (e.g., KIR2DS and KIR3DS) and murine Ly-49 proteins (e.g., Ly-49D and Ly-49H) are expressed by some NK cells. These molecules differ from their inhibitory counterparts (discussed below) by lacking inhibitory motifs (ITIMs) in their relatively shorter cytoplasmic domains and possessing a charged transmembrane region that associates with signal-transducing polypeptides, such as disulfide-linked dimers of DAP12, NKCIRs NK Cell Inhibitory Receptors ILR (IgSF) NK cell inhibitory receptors (NKCIRs) (I) include a number of different human KIRs, specific for HLA-A, -B, or -C allotypes (KIRs may recognize multiple alleles within a particular allotype—e.g., KIR2DL1 recognizes HLA-Cw-2, 4, and 6 allotypes). CTLR superfamily inhibitory receptors include members of the CD94/NKG2 protein family, which comprise receptors formed by lectin-like CD94 with various members of the NKG2 family, such as NKG2A, and recognize the nonclassical class I molecules HLA-E and Qa-1 in humans and mice, respectively, and the murine Ly49 molecules that recognize the classical class I MHC molecules in mice. In even further contrast, NKRP1A, Nkrp1f and Nkrp1d are inhibitory receptors whose ligands are not MHC-related but are CTLR family members expressed on various cell types, such as dendritic cells, macrophages, and lymphocytes.

MHC class I-specific NKCIRs include CTLR Ly-49 receptors (in mice); the IgSF receptors LIRs (Leukocyte Immunoglobulin-like Receptors, in humans), KIRs (e.g., p58 and p70 Killer-cell Immunoglobulin-like Receptors, in humans), and CTLR CD94/NKG2 receptors (in mice and humans). All MHC-I-specific NKCIRs appear to use a common inhibitory mechanism apparently involving phosphorylation of immunotyrosine inhibitory motifs (ITIMs) in their cytoplasmic domains in the course of MHC-I binding and recruitment of tyrosine phosphatases (e.g., SHP-1 and SHP-2) to the phosphorylated ITIMs, resulting in the inhibition of proximal protein tyrosine kinases (PTKs) involved in NK activation through NKCARs Inhibitory CD94/NKG2 heterodimers formed from CTLR glycoproteins, comprise an ITIM-bearing NKG2 molecule (e.g., NKG2A) and bind to non-classical MHC-I molecules (e.g., HLA-E in humans and Qa-1 in mice).

Inhibitory Ly-49 receptors are murine type II membrane disulfide-linked homodimer CTLR glycoproteins, which bind to various MHC-I molecules and deliver typically dominant inhibitory (negative) signals to NK cells. Ly-49A, for example, binds to alpha1/alpha2 domains of MHC-I molecule H-2Dd, whereas Ly-49C binds H-2 Kb. Human NK cells appear to lack homologs of the murine Ly-49 receptors. Instead, human NK cells express KIRs, which are not found in mouse NK cells. Although human KIRs and mouse Ly-49 receptors lack structural homology, they are functionally orthologous: Both types of receptors bind to HLA class I on target cells, resulting in inhibition of NK-mediated cytotoxicity.

An important type of NKCIRs is the KIRs. Generally, KIRs are cell surface glycoproteins, comprising one to three extracellular immunoglobulin-like domains, which are expressed by some T cells as well as most human NK cells. A number of KIRs are well characterized (see, e.g., Carrington and Norman, The KIR Gene Cluster, May 28, 2003, available through the National Center for Biotechnology Information (NCBI) Worldwide Website: ncbi.nlm.nih.gov/books/bookres.fcgi/mono_003/ch1d1.pdf). Human KIRs include KIR2DL and KIR3DL (KIRs also may be referred to by various other names such as CD158e1, CD158k, CD158z, p58 KIR CD158e1 (p70), CD244, etc.) (see, e.g., US Patent Application 20040038894, Radaev et al., Annu. Rev. Biophys. Biomol. Struct., 32:93-114 (2003), Cerweknka et al., Nat. Rev. Immunol. 1:41-49 (2001); Farag et al., Expert Opin. Biol. Ther., 3(2):237-250 (2003); Biassoni et al., J. Cell. Mol. Med., 7(4):376-387 (2003); and Warren et al., British J. Haematology, 121:793-804 (2003), each of which being hereby incorporated in their entirety). The structure of a number of KIRs has been elucidated and reveals remarkable structural similarity between these proteins. See, e.g., Radaev et al., supra.

KIRs can be classified structurally as well as functionally. For example, most KIRs have either two Ig domains (58 kDa KIR2D KIRs), whereas others have three Ig domains (70 kDa KIR3D KIRs) (sometimes respectively referred to as p58 and p70 molecules). KIRs vary also in cytoplasmic tail length. Typically, KIRs with a relatively long cytoplasmic tail (L) deliver an inhibitory signal, whereas KR with a short cytoplasmic tail (S) can activate NK or T cell responses. Nomenclature for KIRs accordingly can be based upon the number of extracellular domains (KIR2D or KIR3D) and whether the cytoplasmic tail is long (KIR2DL or KIR3DL) or short (KIR2DS or KIR3DS). Additional nomenclature information for KIRs is provided in the following Detailed Description of the Invention. Some members of the "KIR family" are NKCARs, or more particularly "KARs" (e.g., KIR2DS2 and KIR2DS4); they typically comprise one or more charged transmembrane residues (e.g., Lys) that associate with an adapter molecule having an immunostimulatory motif (ITAM) (e.g., DAP12). The intracytoplasmic portion of inhibitory KIRs typically comprises one or more ITIMs that recruit phosphatases. Inhibitory KIRs bind to alpha1/alpha2 domains of HLA molecules. Inhibitory KIRs do not appear to typically require adaptor-molecule association for activity. Unless otherwise stated, terms such as "KIR", "KIRs", and the like refer to NKCIR members of the "KIR family" and terms such as "KAR", "KARs", and the like refer to NKCAR members of the "KIR family."

KIRs can bind MHC-I molecules (e.g., certain HLA class I allotypes), typically resulting in the transmission of a negative signal that counteracts, and may override stimulatory, activating signal(s) to the NK cell, thereby preventing the NK cell from killing the associated potential target cell (apparently via ITIM phosphorylation and tyrosine phosphatase (e.g., SH2-domain containing protein tyrosine phosphatases such as SHP-1 and SHP-2) recruitment, leading to PTK (e.g., Syk, TcR and/or ZAP70) dephosphorylation and/or LAT/PLC complex formation inhibition and associated disruption of ITAM cascade(s)). Because viruses often suppress class I MHC expression in cells they infect, such virus-infected cells become susceptible to killing by NK cells. Because cancer cells also often have reduced or no class I MHC expression, these cells, too, can become susceptible to killing by NK cells. Infected cells can also change the proteins bound in the MHC in terms of glycosylation. If this occurs, the MHC-I:protein complex the cell expresses will be altered. If NK-associated KIRs cannot bind to these "foreign" complexes, no inhibitory signal can be generated, and lysis will proceed.

All confirmed inhibitory KIRs appear to interact with different subsets of HLA/MHC antigens depending upon the KIR subtype. In humans, KIRs having two Ig domains (KIR2D) recognize HLA-C allotypes: KIR2DL2 (formerly designated p58.2) and the closely related gene product KIR2DL3 both recognize an epitope shared by group 1 HLA-C allotypes (Cw1, 3, 7, and 8), whereas KIR2DL1 (p58.1) recognizes an epitope shared by the reciprocal group 2 HLA-C allotypes (Cw2, 4, 5, and 6). The specificity of KIR2DL1 appears to be dictated by the presence of a Lys residue at position 80 of group 2 HLA-C alleles. KIR2DL2 and KIR2DL3 recognition appears to be dictated by the presence of an Asn residue at position 80. A substantial majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains, KIR3DL2 (p140), recognizes HLA-A3 and -A11.

Individual MHC-I-specific NK cell receptors of either type (activating or inhibitory) typically do not interact with all MHC class I molecules, but specifically bind to certain allotypes (proteins encoded by different variants of a single genetic locus). Also, an individual NK cell may express several different inhibitory and/or activating receptors which function independently of each other. For example, in humans the presence or absence of a given KIR is variable from one NK cell to another within a single individual. There also is relatively high level of polymorphism of KIRs in humans, with certain KIR molecules being present in some, but not all individuals. Although KIRs and other MHC-recognizing inhibitory receptors may be co-expressed by NK cells, in any given individual's NK repertoire there are typically cells that express a single KIR; accordingly, the corresponding NK cell activity in this latter type of NK cells is inhibited only by cells expressing a specific MHC-I allele group. In fact, recent estimates of the extent of KIR genotype diversity within the population suggest that <0.24% of unrelated individuals can expect to have identical genotypes. The most common Caucasian haplotype, the "A" haplotype (frequency of ~47-59%), contains only one activating KIR gene (KIR2DS4) and six inhibitory KIR loci (KIR3DL3, -2DL3, -2DL1, -2DL4, -3DL1, and -3DL2). The remaining "B" haplotypes are very diverse and contain 2-5 activating KIR loci (including KIR2DS1, -2DS2, -2DS3, and -2DS5).

Antibodies against NK receptors, such as KIRs, have been previously described and there also has been at least some suggestion of combining anti-NK receptor antibodies, such as anti-KIR antibodies, with other anti-cancer agents in the prior art. For example, WO2004056392 describes anti-NKp30 and/or anti-NKp46 antibodies used in admixture with interleukin-2 (IL-2). WO2005009465 describes the combination of a therapeutic antibody (e.g., Rituxan) in combination with a compound that blocks an inhibitory receptor or stimulates an activating receptor of an NK cell (e.g., an anti-KIR mAb, such as the mAb DF200) in order to enhance the efficiency of the treatment with therapeutic antibodies in human subjects (see also US 20050037002). WO2005079766 also describes combinations of antibodies (e.g., anti-tissue factor antibodies) including anti-KIR antibodies for use in cancer therapies. WO2005003168 and WO2005003172 describe combinations of a number of anti-KIR antibodies with a variety of agents, including IL-2 and IL-21. WO2005037306 similarly describes combinations of IL-21, IL-21 derivatives, and IL-21 analogues in combination with anti-KIR antibodies.

The invention described herein relates to the treatment of cancer and pre-cancerous conditions wherein an antibody against a KIR is employed in combination with other cancer or cancer preventive treatments. Specific combinations described herein are new with respect to the prior art and in at least some instances associated with surprising properties, such as unexpected synergistic effects. The invention also relates to new methods and compositions useful for the treatment of viral infections, comprising a combination of an antibody against a KIR and an anti-viral medicament or therapeutic technique.

SUMMARY OF THE INVENTION

This invention relates to the treatment of cancer and pre-cancerous conditions wherein an antibody against a killer immunoglobulin-like receptor (KIR) is employed in combination with other cancer or cancer preventive treatments. The invention provides a method of treating cancer or viral infections comprising administration of a therapeutically active amount of one or more anti-KIR antibodies and a therapeutically active amount of one or more antibodies against inhibitory receptors on Natural Killer (NK) cells.

The invention further provides a method of treating cancer or viral infections comprising administration of a therapeutically active amount of one or more anti-KIR antibodies and a therapeutically active amount of one or more antibodies against inhibitory receptors on T cells, cytokines that stimulate NK cells, other agents that stimulate NK cells, and other inhibitory receptors on other cell types such as macrophages.

To better illustrate the invention described herein, a nonlimiting list of exemplary aspects and features of the invention is provided here:

In one aspect, the invention relates to a method of treating cancer or viral infections comprising administration of a therapeutically active amount of an anti-KIR antibody (e.g., an anti-KIR2DL1 antibody and an anti-KIR2DL2 antibody, or an anti-KIR2DL1 antibody and an anti-KIR2DL3 antibody, or an anti-KIR2DL1 antibody and an anti-KIR2DL2 antibody and an anti-KIR2DL3 antibody, or an anti-KIR antibody that binds at least two different human inhibitory KIR receptor gene products, wherein said antibody is capable of neutralizing KIR-mediated inhibition of NK cell cytotoxicity in NK cells expressing at least one of the two different human inhibitory KIR receptors, or an anti-KIR2D antibody and an anti-KIR3D antibody) and a therapeutically active amount of one or more antibodies against inhibitory receptors on Natural Killer (NK) cells. In a particular variation of this aspect, the other inhibitory receptors is selected from CTLA4, CD94, NKG2A, LIR, and KIR.

In another aspect, the invention provides a method of treating cancer or viral infections comprising administration of a therapeutically active amount of one or more anti-KIR antibodies and a therapeutically active amount of one or more antibodies against receptors responsible for negative regulation of responses by white blood cells.

In still another aspect, the invention relates to a method of treating cancer or viral infections comprising administration of a therapeutically active amount of one or more anti-KIR antibodies and a therapeutically active amount of one or more cytokines that stimulates NK cells, selected from interferon alpha, interferon beta, interleukin-2 (IL-2), IL-7, IL-12, IL-15, IL-18, IL-20, and IL-21, IL-28, IL-29, and IL-31.

In a further aspect, the invention relates to a method of treating cancer or viral infections comprising administration of a therapeutically active amount of one or more anti-KIR antibodies and a therapeutically active amount of one or more agents that stimulate NK cells. In a particular variation of this aspect, the one or more agents that stimulate NK cells is selected from Gleevec and histamine dihydrochloride.

Any of the various aspects described above can be modified by the additional or alternative use of one or more therapeutic antibodies specific for a ligand on cancer cells or virus infected cells. In a particular variation of this additional/alternative feature, the one or more therapeutic antibodies specific for a ligand on cancer cells or virus infected cells is selected from anti-HER-2 (e.g., Trastuzumab), anti-CD20 (e.g., Rituximab, Ibritumomab tiuxetan or Tositumumab-I131), anti-EGFR (Cetuximab), anti-VEGF (e.g., Gemtuzumab ozogamizin), anti-CD22, end-CD33 (e.g. Gemtuzumab) and anti-CD52 (e.g., Alemtuzumab).

In another aspect, any one of the various above-described methods may further optionally or alternatively (e.g., as a substitute for the other antibody) be modified by application of a chemotherapy treatment with one or more chemotherapy agents. In a particular aspect, the optional or additional chemotherapy agent is a taxane. In another particular aspect, the chemotherapy agent is cyclophosphamide.

In still another aspect, any of the various methods are alternatively or additionally modified by the inclusion of radiation therapy in the method.

In a further aspect, the invention relates to a method for treating cancer comprising administration of a therapeutically active amount to a patient in need thereof of an anti-KIR antibody and a further therapeutic agent selected from the group consisting of
Anti-cancer monoclonal antibodies
Chemotherapy agents
Anti-cancer Nucleic Acids
Oncolytic Viruses
Cancer Vaccines
Anti-Cancer Cytokines
Tumor internalization promoters
Telomerase and Telomerase-related Compositions
Immunomodulators
Cell Cycle Control and Apoptosis-Related Agents
Growth factor inhibitors
Angiogenesis inhibitors
Hormone regulating agents
Whole-cell Vaccines and Adoptive Immunotherapy
Immune System and Intracellular Signaling Inhibitors
Anti-anergic agents
Internal vaccines In still another aspect, the invention provides a method for treating cancer comprising administration of a therapeutically active amount to a patient in need thereof of an anti-KIR antibody and a further therapeutic agent selected from the group consisting of PTK/ZK, fluoropyrimidines, carbamates, such as capecitabine; non-polyglutamatable thymidylate synthase inhibitors; nucleoside analogs, such as tocladesine; antifolates such as pemetrexed disodium; taxanes and taxane analogs; topoisomerase inhibitors; polyamine analogs; mTOR inhibitors (e.g., rapamcyin ester); alkylating agents (e.g., oxaliplatin); lectin inhibitors; vitamin D analogs, anti-angiogenesis compounds (e.g., endostatin, angiocol, anti-PDGF mAbs and other PDGF (platelet derived growth factor) inhibitors, PEDFs (pigment epithelium derived growth factors), and the like); carbohydrate processing inhibitors; antimetabolism folate antagonists; thumidylate synthase inhibitors; antimetabolites (e.g., raltitrexed); ribonuclease reductase inhibitors; dioxolate nucleoside analogs; thimylate syntase inhibitors; gonadotropin-releasing hormone (GRNH) peptides; human chorionic gonadotropin; chemically modified tetracyclines (e.g., CMT-3; COL-3), cytosine deaminase, thymopentin, DTIC, carmustine, carboplatin, vinblastine, temozolomide, vindesine, and thymosin-α, Histone deacetylase inhibitors (e.g., phenylbutyrate), DNA repair agents (e.g., DNA repair enzymes and related compositions such as DIMERICINE (T4 endonuclease V-containing liposome)).

In another aspect, the invention relates to the use of a therapeutically effective amount of an anti-KIR antibody and an interleukin-2, an interleukin-2 derivative, or an interleukin-2 analogue (collectively, an "interleukin-2 protein"), such as recombinant human interleukin-2, for the manufacture of a medicament for treating cancer. In a particular variation of this aspect, the cancer is a lung cancer. In another particular facet of this aspect, the medicament is characterized as being free from Rituxan and/or Campath, or (in some instances) any other pharmaceutically active agents besides the anti-KIR antibody and interleukin-2 protein. In another particular facet, the anti-KIR antibody is characterized as competing with mAb DF200 or 1-7F9. In another facet, the anti-KIR antibody is 1-7F9. In yet another facet, the antibody is not 1-7F9, but comprises the VL and VH domain of 1-7F9. In still another particular facet, the antibody is not 1-7F9, but comprises the VL and VH CDRs of 1-7F9. In still another aspect, the anti-KIR antibody is a non-cross-reactive antibody.

The invention also relates to the provision of a pharmaceutically acceptable composition comprising an effective amount of anti-KIR antibody and an interleukin-2, an intereukin-2 derivative, or an interleukin-2 analogue. The composition can be characterized by any of the features described above with respect to the use of interleukin-2 protein and anti-KIR antibody in the production of a medicament for the treatment of cancer.

In still another aspect, the invention relates to the use of a therapeutically effective amount of an anti-KIR antibody and an anti-viral agent, such as an interleukin-2, an interleukin-2 derivative, or an interleukin-2 analogue, for the manufacture of a medicament for treating viral infections. In a particular facet, the viral infection to be treated is a hepatitis C virus (HCV) infection. In another particular facet, the viral infection to be treated is a HIV infection.

These aspects are more fully described in, and additional aspects, features, and advantages of the invention will be apparent from, the description of the invention provided herein.

BRIEF DESCRIPTION OF THE FIGURES

FIG. 3 shows an alignment of the VL domain and VL CDR sequences of anti-KIR antibodies Pan-2D and DF200. (A) Alignment of variable light (VL) regions of DF200 (SEQ ID NO:1) and Pan-2D (SEQ ID NO:2); consensus SEQ ID NO:17). Numbers above amino acid sequences indicate position respective to initiation of translation Met (+1) in the immature (non-secreted) immunoglobulin. (B) Alignment of CDR-L1 sequences (SEQ ID NOs:3 and 4); consensus (SEQ ID NO:18). (C) Alignment of CDR-L2 sequences (SEQ ID NOs:5 and 6); consensus (SEQ ID NO:19). (D) Alignment of CDR-L3 sequences (SEQ ID NOs:7 and 8); consensus (SEQ ID NO:20).

FIG. 4 shows the sequences of the VH domain and VH CDRs of anti-KIR antibody DF200. (A) DF-200 VH region, immature protein. The secreted, mature VH starts at position 20: residue Q. (B) CDR-H1. (C) CDR-H2. (D) CDR-H3.

FIG. 5 shows the sequences of the VH and VL domains of anti-KIR antibody 1-7F9. (A) Translation of HuKIR 1-7F9 mature variable light chain. (B) Nucleotide sequence encoding HuKIR 1-7F9 mature variable light chain. (C) Translation of HuKIR 1-7F9 mature variable heavy chain. (D) Nucleotide sequence encoding HuKIR 1-7F9 mature heavy chain.

DESCRIPTION OF THE INVENTION

Figure 1:
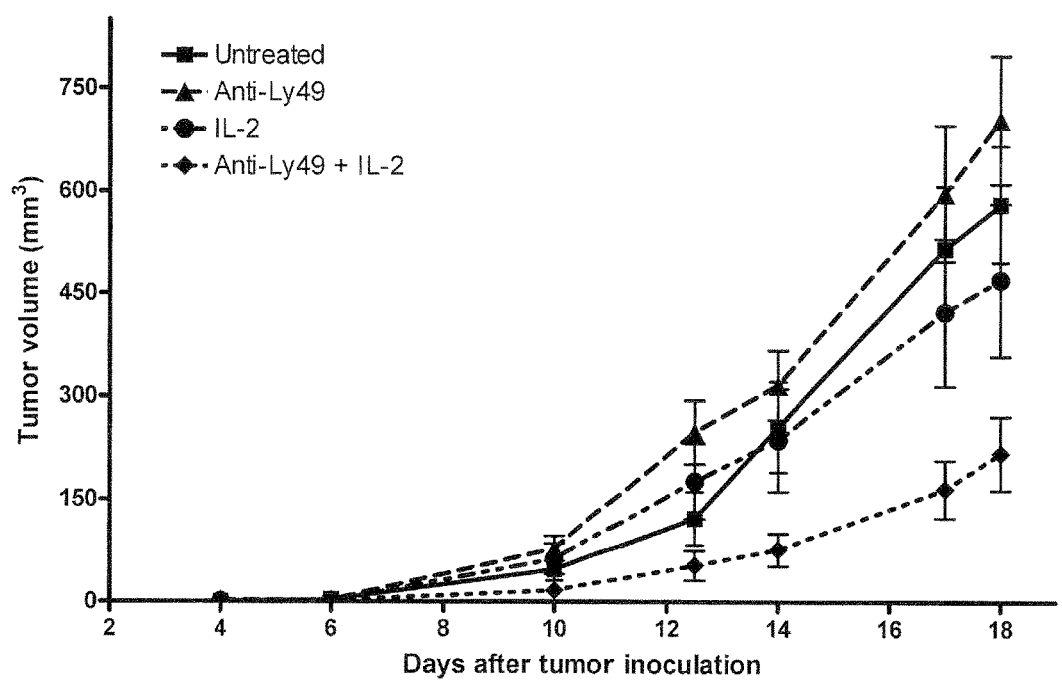
FIG. 1 shows the results of experiments performed with a NK CIR antibody (the anti-Ly49(5E6) mAb reacts with the mouse ortholog of KIR) and interleukin-2 (IL-2), alone and in combination, in a mouse cancer model.

Unless otherwise stated or clearly contradicted by context, the term antibody in the context of this invention refers to an immunoglobulin (Ig) molecule, a fragment of an Ig molecule, or a derivative of either thereof that has the ability to (a) specifically bind to at least one target antigen under typical physiological conditions for significant periods of time and/or (b) modulate a physiological response associated with its target KIR, such as modulating KIR-modulated NK cell activity. A significant period of time in this respect means any period suitable for detection of the antibody-antigen complex in a standard immunological assay, such as an ELISA. Typically, a significant period of time is a period of at least about 30 minutes, at least about 45 minutes, at least about one hour, at least about two hours, at least about four hours, at least about 8 hours, at least about 12 hours, about 24 hours or more, about 48 hours or more, etc.

Immunoglobulins are a class of structurally related proteins comprising heavy chains (e.g., α, Δ, ε, γ, and μ chains) and light chains (e.g., κ and λ chains). In humans, immunoglobulins may be divided into five major classes (IgA, IgD, IgE, IgG, and IgM) according to which heavy chains are contained in the Ig molecule.

The structure of immunoglobulins is well characterized. See, e.g., Fundamental Immunology (Paul, W., ed., 2nd ed. Raven Press, N.Y. (1989)). IgG molecules, the most common type of immunoglobulin, comprise two pairs of polypeptide chains, one pair of light (L), low molecular weight chains and one pair of heavy (H) chains, all four interconnected by disulfide bonds. Briefly, each heavy chain typically is comprised of a heavy chain variable region (abbreviated herein as HCVR or VH) and a heavy chain constant region. The heavy chain constant region typically is comprised of three domains, CH1, CH2, and CH3. Each light chain typically is comprised of a light chain variable region (abbreviated herein as LCVR or VL) and a light chain constant region. The light chain constant region typically is comprised of one domain, CL. The VH and VL regions can be further subdivided into regions of hypervariability (or hypervariable regions, which can be hypervariable in sequence and/or form of structurally defined loops), also termed complementarity determining regions (CDRs), interspersed with regions that are more conserved, termed framework regions (FR). In full length, naturally produced antibodies, each VH and VL typically is composed of three CDRs and four FRs, arranged from amino-terminus to carboxy-terminus in the following order: FR1, CDR1, FR2, CDR2, FR3, CDR3, FR4 (which also may be referred to as FR L1, CDR L1, etc. or loop L1, L2, L3 in the light chain variable domain and loop H1, H2, and H3 in the heavy chain domain in the case of hypervariable loop regions (see, e.g., Chothia and Lesk J. Mol. Biol. 196:901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat" and "according to Kabat" herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the anti-body with a "standard" Kabat numbered sequence.

As indicated above, an anti-KIR antibody can be in the form of (or comprise) an antibody "fragment" that retains the ability to specifically bind to a KIR. Such antibody fragments can be characterized by possessing any one or combination of the aforementioned features associated with full length antibodies, discussed elsewhere herein, to the extent appropriate (e.g., many antibody fragments lack an Fc domain and, accordingly, do not induce or promote antibody-associated complement functions). The antigen-binding function of antibodies can be performed by any number of suitable fragments thereof. Examples of anti-body fragments include (i) a Fab fragment, a monovalent fragment consisting essentially of the VL, VH, CL and CH I domains; (ii) F(ab)₂ and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain antibodies or single chain Fv (scFv); see e.g., Bird et al. (1988) Science 242:423-426: and Huston et al. (1988) Proc. Natl. Acad. Sci. USA 85:5879-5883). Such single chain antibodies also are encompassed within terms such as antibody fragment and antibody-like peptide/molecule, unless otherwise noted or clearly indicated by context. Other forms of single chain antibodies, such as diabodies also are intended be encompassed by these terms. Diabodies are bivalent, bispecific antibodies in which VH and VL domains are expressed on a single polypeptide chain, but using a linker that typically is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123; and Cao et al. (1998), Bioconjugate Chem. 9, 635-644). Although having similar binding properties as full-length antibodies, such antibody fragments collectively and each independently are unique features of the invention, exhibiting different biological and/or physiochemical properties and utilities than antibodies. These and other useful antibody fragments and antibody-like molecules provided by this invention are discussed further herein. It should be generally understood that any suitable antibody fragment can be used as a surrogate for an antibody in inventive compositions and methods described herein, and visa versa, unless otherwise stated or clearly contradicted by context.

In a general sense, the term antibody includes polyclonal antibodies and monoclonal antibodies (mAbs). The term "monoclonal antibody" refers to a composition comprising a homogeneous antibody population having a uniform structure and specificity. Polyclonal antibodies typically are derived from the serum of an animal that has been immunogenically challenged, but they can also be derived by recombinant technology. Anti-KIR antibodies can be considered monoclonal antibodies, regardless of the manner in which they are produced.

An antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. No. 5,916,771), and other suitable techniques known in the art. Thus, for example, the effector function of multispecific multivalent antibodies provided by the invention may be "changed" with respect to the isotype of one or both parent antibodies by isotype switching to, e.g., an IgG1, IgG2, IgG3, IgG4, IgD, IgA, IgE, or IgM antibody for various therapeutic uses.

It should be noted that KIRs are known by several aliases, as reflected here in Table 1 and Table 2:

TABLE 1

KIR Nomenclature

| KIR | Full name | Aliases | Accession ID |
|---|---|---|---|
| KIR2DL1 | killer cell immunoglobulin-like receptor, two domains, long cytoplasmic tail, 1 | cl-42, nkat1, 47.11, p58.1, CD158a | L41267 |
| KIR2DL2 | killer cell immunoglobulin-like receptor, two domains, long cytoplasmic tail, 2 | cl-43, nkat6, CD158b1 | L76669 |
| KIR2DL3 | killer cell immunoglobulin-like receptor, two domains, long cytoplasmic tail, 3 | cl-6, nkat2, nkat2a, nkat2b, p58, CD158b2 | L41268 |
| KIR2DL4 | killer cell immunoglobulin-like receptor, two domains, long cytoplasmic tail, 4 | 103AS, 15.212, CD158d | X97229 |
| KIR2DL5A | killer cell immunoglobulin-like receptor, two domains, long cytoplasmic tail, 5A | KIR2DL5.1, CD158f | AF217485 |
| KIR2DL5B | killer cell immunoglobulin-like receptor, two domains, long cytoplasmic tail, 5B | KIR2DL5.2, KIR2DL5.3, KIR2DL5.4 | AF217486 |
| KIR2DS1 | killer cell immunoglobulin-like receptor, two domains, short cytoplasmic tail, 1 | EB6ActI, EB6ActII, CD158h | X89892 |
| KIR2DS2 | killer cell immunoglobulin-like receptor, two domains, short cytoplasmic tail, 2 | cl-49, nkat5, 183ActI, CD158j | L76667 |
| KIR2DS3 | killer cell immunoglobulin-like receptor, two domains, short cytoplasmic tail, 3 | nkat7 | L76670 |
| KIR2DS4 | killer cell immunoglobulin-like receptor, two domains, short cytoplasmic tail, 4 | cl-39, KKA3, nkat8, CD158i | L76671 |
| KIR2DS5 | killer cell immunoglobulin-like receptor, two domains, short cytoplasmic tail, 5 | nkat9, CD158g | L76672 |
| KIR2DP1 | killer cell immunoglobulin-like receptor, two domains, pseudogene 1 | KIRZ, KIRY, KIR15, KIR2DL6 | AF204908 |
| KIR3DL1 | killer cell immunoglobulin-like receptor, three domains, long cytoplasmic tail, 1 | cl-2, NKB1, cl-11, nkat3, NKB1B, AMB11, KIR, CD158e1 | L41269 |
| KIR3DL2 | killer cell immunoglobulin-like receptor, three domains, long cytoplasmic tail, 2 | cl-5, nkat4, nkat4a, nkat4b, CD158k | L41270 |
| KIR3DL3 | killer cell immunoglobulin-like receptor, three domains, long cytoplasmic tail, 3 | KIRC1, KIR3DL7, KIR44, CD158z | AF352324 |
| KIR3DS1 | killer cell immunoglobulin-like receptor, three domains, short cytoplasmic tail, 1 | nkat10, CD158e2 | L76661 |
| KIR3DP1 | killer cell immunoglobulin-like receptor, three domains, pseudogene 1 | KIRX, KIR48, KIR2DS6, KIR3DS2P, CD158c | AF204919, AF204915- AF204917 |

Obtained from the Hugo Gene Nomenclature Committee, See Worldwide Website: gene.ucl.ac.uk/nomenclature/gene-family/kir.html.

TABLE 2

KIR CD Nomenclature

| Common Name 1 | Common Name 2 | CD Designation |
|---|---|---|
| KIR3DL7 | KIRC1 | CD158z |
| KIR2DL2/L3 | p58.2/p58.3 | CD158b1/b2 |
| KIR2DL1 | p58.1 | CD158z |
| KIR2DS6 | KIRX | CD158b1/b2 |
| KIR2DL4 | — | CD158c |
| KIR3DL1/S1 | p70 | CD158d |
| KIR2DL5 | — | CD158e1/e2 |
| KIR2DS5 | — | CD158f |
| KIR2DS1 | p50.1 | CD158h |
| KIR2DS4 | p50.3 | CD158i |
| KIR2DS2 | p50.2 | CD158j |
| KIR3DL2 | p140 | Cd158k |

Andre et al., Nature Immunol. 2(8): 661 (2001).

Functional Characteristics of Anti-KIR Antibodies

Advantageous Anti-KIR antibodies may be classified based on functional characteristics, particularly with respect to their ability to cross-react or cross-bind more than one KIR, such as more than one type of inhibitory KIR, and/or the ability to effectively neutralize NK inhibitory signals.

i. KIR Cross-reactivity

Anti-KIR antibodies that effectively bind to more than one type of KIR are a particularly advantageous feature of the invention. In a particular exemplary aspect, the invention provides Anti-KIR Antibodies that bind to at least two inhibitory KIR receptors at the surface of NK cells. In an even more particular illustrative aspect, the invention provides Anti-KIR antibodies that bind a common antigenic determinant region of human KIR2DL receptors. In a yet even further specific aspect, the invention provides an anti-KIR antibody that binds to KIR2DL1, KIR2DL2, and KIR2DL3 receptors.

The term "KIR2DL2/3" can be used to refer to either or both of the KIR2DL2 and KIR2DL3 receptors. These two receptors have a very high homology, are allelic forms of the same gene, and are considered by the art to be interchangeable in many respects. Accordingly, KIR2DL2/3 can be considered in certain respects to be a single inhibitory KIR molecule. While Anti-KIR antibodies that cross-react with KIR2DL2/3 are within the invention, Anti-KR antibodies that have a KR-binding profile that only included KIR2DL2 and KIR2DL3 are not considered "cross-reactive."

Because at least one of KIR2DL1 or KID2DL2/3 is present in at least about 90% of the human population, KIR2DL1-KIR2DL2/3 cross-reactive Anti-KIR antibodies can promote or enhance NK activity against most of the HLA-C allotype-associated cells, respectively group 2 HLA-C allotypes and group 1 HLA-C allotypes. A composition comprising a single KIR antibodies having such cross-reactivity may be used in treatment and/or diagnosis of most human subjects, thereby eliminating the necessity of genetic profiling of the patient and reducing the amount of different antibodies that need to be administered to a patient to ensure an effective result.

Cross-reacting Anti-KIR antibodies can have any suitable composition and can be obtained by a number of suitable techniques. For example, a cross-reactive Anti-KIR antibody can comprise a number of KIR ligand and/or anti-Anti-KIR antibody sequences that bind to different KIRs, which may be associated by conjugation, multimerization, or (in the case of peptide ligands) by being comprised in a fusion protein. In another aspect, an anti-KIR antibody is provided that comprises anti-Anti-KIR antibody sequences from a cross-reacting anti-Anti-KIR antibody.

Cross-reacting anti-Anti-KIR antibodies, from which KIR-binding sequences can be obtained or derived, are known. An example of such an antibody is described in, e.g., Watzl et al., Tissue Antigens, 56, p. 240 (2000). Another example of such an antibody is monoclonal antibody NKVSF1, described in G. M. Spaggiara et al., Blood, 100, pp. 4098-4107 (2002), which is said to recognize a common epitope of CD158a (KIR2DL1), CD158b (KIR2DL2) and p50.3 (KIR2DS4). Antibody NKVSF1 (also referred to as pan2D mAb) is available from Serotec (Cergy Sainte-Christophe, France), Catalog ref no. MCA2243. The monoclonal antibody DF200, which reacts with various members of the KIR family including KIR2DL1 and KIR2DL2/3 is another example of such an antibody. A hybridoma that produces DF200 has been deposited at the CNCM culture collection, as Identification no. "DF200", registration no. CNCM I-3224, registered 10 Jun. 2004, Collection Nationale de Cultures de Microorganismes, Institut Pasteur, 25, Rue du Docteur Roux, F-75724 Paris Cedex 15, France. Several additional monoclonal antibodies can be generated and demonstrated to be cross-reactive anti-Anti-KIR antibodies.

A cross-reactive Anti-KIR antibody can have any suitable affinity and/or avidity for the two or more KIRs to which it binds. Affinity refers to the strength of binding of an anti-KIR antibody or other antigen-binding protein to an epitope or antigenic determinant. Typically, affinity is measured in terms of a dissociation constant $K_d$, defined as $[Ab] \times [Ag]/[Ab-Ag]$ where [Ab-Ag] is the molar concentration of the antibody-antigen complex, [Ab] is the molar concentration of the unbound antibody and [Ag] is the molar concentration of the unbound antigen. The affinity constant $K_a$ is defined by $1/K_d$. Suitable methods for determining binding peptide specificity and affinity by competitive inhibition, equilibrium dialysis, and the like can be found in, e.g., Harlow, et al., Antibodies: A Laboratory Manual, Cold Spring Harbor Laboratory Press, Cold Spring Harbor, N.Y., 1988); Colligan et al., eds., Current Protocols in Immunology, Greene Publishing Assoc. and Wiley Interscience, N.Y., (1992, 1993), and Muller, Meth. Enzymol. 92:589-601 (1983).

Typically, an anti-KIR antibody provided by the invention has an affinity for at least one KIR in the range of about $10^4$ to about $10^{10}$ M$^{-1}$ (e.g., about $10^7$ to about $10^9$ M$^{-1}$). The term immunoreact herein typically refers to binding of an anti-KIR antibody to a KIR with a dissociation constant $K_d$ lower than about $10^{-4}$ M. For example, in a particular aspect the invention provides Anti-KIR antibody that have an average disassociation constant ($K_D$) of about $7 \times 10^{-9}$ M or more with respect to KIR2DL1 and KIR2DL2/3, as determined by, e.g., surface plasmon resonance (SPR) screening (such as by analysis with a BIACORE SPR analytical device). In a more particular exemplary aspect, the invention provides Anti-KIR antibodies that have a KD of about $2 \times 10^{-9}$ M (e.g., about $0.1-4 \times 10^{-9}$ M) or more for KIR2DL2/3 and about $11 \times 10^{-9}$ M (e.g., about $7-15 \times 10^{-9}$ M) or more for KIR2DL1.

Affinity can be determined by any of the methods described elsewhere herein or their known equivalents in the art. An example of one method that can be used to determine affinity is provided in Scatchard analysis of Munson & Pollard, Anal. Biochem. 107:220 (1980). Binding affinity also may be determined by equilibrium methods (e.g.

enzyme-linked immunoabsorbent assay (ELISA) or radioimmunoassay (RIA)) or kinetics analysis (e.g. BIA-CORE analysis).

Anti-KIR antibodies also or alternatively can be characterized by exhibiting KIR binding with a disassociation constant of less than about 100 nM, less than about 50 nM, less than about 10 nM, about 5 nM or less, about 1 nM or less, about 0.5 nM or less, about 0.1 nM or less, about 0.01 nM or less, or even about 0.001 nM or less.

Avidity refers to the overall strength of the total interactions between a binding protein and antigen (e.g., the total strength of interactions between an anti-KIR antibody and a KIR). Affinity is the strength of the total noncovalent interactions between a single antigen-binding site on an antibody or other binding peptide and a single epitope or antigenic determinant. Avidity typically is governed by three major factors: the intrinsic affinity of the binding protein for the epitope(s) or antigenic determinant(s) to which it binds, the valence of the antibody or binding protein and antigen (e.g., an anti-KIR antibody with a valency of three, four, or more will typically exhibit higher levels of avidity for an antigen than a bivalent anti-body and a bivalent antibody can will have a higher avidity for an antigen than a univalent antibody, especially where there are repeated epitopes in the antigen), and/or the geometric arrangement of the interacting components. Avidity typically is measured by the same type of techniques used to assess affinity.

In another aspect, the invention provides an anti-KIR antibody that cross-reacts with KIRs from two or more species. For example, in one aspect, the invention provides an anti-KIR antibody that cross-reacts with KIRs of humans and cynomolgus monkeys. In a particular aspect, the invention provides an anti-KIR antibody that cross-reacts with at least two human KIRs and also binds to NK cells of cynomolgus monkeys. Such an anti-KIR antibody can comprise sequences from or that are derived from antibody NKVSF1, which exhibits such a cross-reactivity profile. Such Anti-KIR antibodies can be subjected to toxicity testing and other useful studies in cynomolgus monkeys, if needed.

Antibodies that are cross-reactive with a variety of KIRs can be used in the combination compositions and methods of the invention. Exemplary cross-reactivity profiles of such antibodies include antibodies that cross-react with KIRs 2DL1 plus 3DL1, 2DL1 plus 3DL2, 2DL2/3 plus 3DL1, and 2DL2/3 plus 3DL2 (such antibodies, in and of themselves, represent another feature of the invention).

Thus, for example, the inventive methods or compositions can comprise an anti-KIR antibody that binds KIR2DL1, KIR2DL2, and KIR2DL3 and reduces or blocks inhibition of KIR-mediated NK cell cytotoxicity, as described in, e.g., WO2005003168.

Exemplary anti-KIR antibodies useful in the combination methods and compositions of the invention include anti-KIR antibodies comprising a VL region that corresponds to that of anti-KIR antibody DF200, or consists essentially of such a VL region (by being substantially similar and retaining a similar binding profile and affinity), or a VL sequence/domain that is highly similar (e.g., at least about 90% identical or 95% identical) to the VL sequence of DF200. The VL sequence of DF200 is shown in FIG. 3. Such anti-KIR antibodies also may alternatively be defined by comprising the set of light variable CDRs of DF200 (also shown in FIG. 3). Such an antibody typically also will comprise either the VH domain of DF200 or a highly similar sequence (e.g., a sequence having high identity to the DF200 VH domain or otherwise consisting essentially of such a sequence) or at least the heavy variable CDRs of DF200 (shown in FIG. 4).

In another exemplary aspect, the combination composition or method of the invention includes an anti-KIR antibody comprising VH and VL sequences that correspond to or are highly similar to (e.g., consists essentially of) the VH and VL sequences of antibody 1-7F9 (shown in FIG. 5) or at least comprises the VL and VH CDRs of 1-7F9.

In another aspect, the inventive methods or compositions are characterized by comprising an anti-KIR antibody that competes with one of these antibodies or one of the other anti-KIR antibodies descried in the references incorporated herein (e.g., Pan-2D)

Antibodies that compete with exemplary anti-KIR antibodies, such as DF200, 1-7F9, and/or NKVSF1, can be identified using known screening assays. A number of such assays are routinely practiced and well known in the art (see, e.g., U.S. Pat. No. 5,660,827, which is specifically incorporated herein by reference). Protocols based on, e.g., ELISAs, radio-immunoassays, Western blotting, and the use of BIA-CORE analysis are suitable for use in such competition studies.

One can, e.g., pre-mix the control antibody (e.g., DF200, NKVSF1, or 1-7F9) with varying amounts of the test antibody (e.g., in ratios of about 1:1, 1:2, 1:10 or about 1:100) for a period of time prior to applying to a KIR antigen sample. Alternatively, the control and varying amounts of test antibody can simply be added separately and admixed during exposure to the KIR antigen sample. As long as one can distinguish bound from free antibodies (e.g., by using separation or washing techniques to eliminate un-bound antibodies) and control anti-body from the test antibody (e.g., by using species specific or isotype specific secondary antibodies or by specifically labelling the control antibody with a detectable label) one will be able to determine if the test antibody reduce the binding of the control antibody to the different KIR2DL antigens, indicating that the test antibody recognizes substantially the same epitope as the control. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of control antibody to one or both of KIR2DL1 and KIR2DL3 antigens by at least about 50%, such as at least about 60%, or more preferably at least about 70% (e.g., about 65-100%), at any ratio of control:test antibody between about 1:1 or 1:10 and about 1:100 is considered to be an antibody that competes with the control.

Competition can also be assessed by, for example, flow cytometry. In such a test, cells bearing a given KIR can be incubated first with a control antibody, and then with the test antibody labeled with a fluorochrome or biotin. The antibody is said to compete with control antibody if the binding obtained upon pre-incubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIACORE chip (or other media suitable for surface plasmon resonance analysis). The binding of a control antibody to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody to both of KIR2DL1 and KIR2DL2/3 antigens by at least about 20% or more, at least about 40%, at least about 50%, at least about 70%, or more, can be considered to be an antibody that competes with the control antibody. Preferably, such test antibody will reduce the binding of the control antibody to each of at least the KIR2DL1, 2, and 3 antigens by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

Determination of whether an antibody or other agent binds to the same or substantially the same epitope region as, e.g., DF200, NKVSF1, or 1-7F9, can be carried out using methods known to the person skilled in the art. In an example of epitope mapping/characterization methods, an epitope region for an anti-KIR antibody may be determined by epitope "foot-printing" using chemical modification of the exposed amines/carboxyls in the KIR2DL1 or KIR2DL2/3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast micro-bore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3): 516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR antibody can subsequently be identified by comparison of samples subjected to trypsin digestion and samples incubated with antibody and then subjected to digestion by e.g. trypsin (thereby revealing a foot print for the antibody). Other enzymes like chymotrypsin, pepsin, etc., also or alternatively can be used in a similar epitope characterization methods. Moreover, enzymatic digestion can provide a quick method for analyzing whether a potential antigenic determinant sequence is within a region of the KIR2DL1 in the context of a KIR-binding agent. If the polypeptide is not surface exposed, it is most likely not relevant in terms of immunogenicity/antigenicity. See, e.g., Manca, Ann 1st Super Sanita. 1991; 27(1):15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant resuction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

Of course, such specific exemplary antibodies (e.g., DF200 and 1-7F9) also may be included in the inventive methods or compositions.

In another aspect, the inventive method or composition is characterized by inclusion of only antibodies that are not cross-reactive with more than one KIR. For example, monoclonal antibodies specific only for KIR2DL1 have been shown to block the interactions between KIR2DL1 and HLA-Cw4 allotypes, as well as similar HLA-C allotypes belonging to the same group as Cw4 (Moretta et al., J Exp Med. 1993; 178(2):597-604; the disclosure of which is incorporated herein by reference). In another example, monoclonal antibodies against KIR2DL2/3 have also been described that block the interactions of KIR2DL2/3 with HLACw3 (or the like) allotypes (Moretta et al., 1993, supra). Optionally, the antibody can be selected from the group consisting of GL183 (KIR2DL2/3/S2-specific, available from Immunotech, France and Beckton Dickinson, USA); EB6 (KIR2DL1/s1-specific, available from Immunotech, France and Beckton Dickinson, USA); AZ138 (KIR3DL1-specific, available from Moretta et al, Univ. Genova, Italy); Q66 (KIR3DL2-specific, available from Immunotech, France); and DX9, Z27 (KIR3DL1-specific, available from Immunotech, France and Beckton Dickinson, USA).

Neutralization of KIR-Associated NK Cell Inhibition

Anti-KIR antibodies also or alternatively can be characterized on the basis of their ability to block or neutralize NK inhibition and thereby potentiate NK cell activity against otherwise blocked target cells. As indicated above, Anti-KIR antibodies that bind to at least one KIR for a sufficient amount of time for detection and/or to deliver a "payload" to target tissues, cells, etc. are important aspects of this invention. However, Anti-KIR antibodies that neutralize KIR-mediated inhibition of NK cell cytotoxicity in NK cells also are an advantageous feature of this invention. Such Anti-KIR antibodies may be used directly as therapeutic agents in a native form (e.g., without conjugation to a cytotoxic agent). A more particular advantageous feature of the invention is Anti-KIR antibodies that cross-react with two or more KIRs and neutralize the inhibitory activity associated with some or all (typically preferably all) of such associated KIRs.

While cross-reacting anti-Anti-KIR antibodies have been reported in the literature, at least some of the cross-reactive anti-Anti-KIR antibodies that are currently known do not appear to exhibit potentiation of NK cell activity (see, e.g., Watzl et al., Tissue Antigens, 56, p. 240 (2000)). Accordingly, such antibodies may be of limited usefulness with respect to serving as a therapeutic agent suitable for use in the majority of the human population (at least in their unmodified native form). In this respect. Anti-KIR antibodies that neutralize KIR-mediated inhibition of NK cell cytotoxicity in NK cells expressing at least one of the at least two different target KIRs associated therewith represent a particularly advantageous aspect of the invention.

Neutralizing Anti-KIR antibodies may partially or fully neutralize the KIR-mediated inhibition of NK cell cytotoxicity. Neutralization refers to any substantial blocking of otherwise present inhibitory signals. Neutralization can be measured by any suitable method. In one aspect, neutralization of inhibition is reflected in that the neutralizing Anti-KIR antibody (ies) cause(s) an least about 20%, preferably at least about 30%, at least about 40%, at least about 50%, at least about 60%, at least about 75% or more (e.g., about 25-100%) increase in NK cell-mediated specific lysis in a particular mixture of NK and NK target cells compared to the amount of specific lysis that typically occurs in a substantially identical setting without the presence of the Anti-KIR antibody (ies). The percentage increase in this aspect can be determined by, e.g., comparison with the results of chromium release toxicity test assays obtained from a mixture of NK target cells and NK cells not blocked their associated KIR(s) (100%) and a mixture of NK cells and NK target cells in which the NK target cells present a cognate MHC class I molecule for the inhibitory KIR on the NK cells (0%). In an advantageous aspect, the invention provides Anti-KIR antibodies that induce lysis of cell(s) that would not be effectively lysed without the presence of such Anti-KIR antibody. Alternatively, neutralization of KIR inhibitory activity can be indicated by, e.g., the results of a chromium assay using an NK cell clone or transfectant expressing one or several inhibitory KIRs and a target cell expressing only one HLA allele that is recognized by one of the KIRs on the NK cell, where the level of cytotoxicity obtained with the antibody is at least about 20%, such as at least about 30%, at least about 40%, at least about 50%, at least about 60%, at least about 70% or more (e.g., about 25-100%) of the cytotoxicity observed with a known blocking anti-MHC class I molecule is administered in a substantially identical setting, such as W6/32 anti-MHC class I antibody (which is currently available from, e.g., Research Diagnostics, Flanders, N.J., USA and described in, e.g., Shields et al., Tissue Antigens. 1998 May; 51(5):567-70).

Chromium release assays and other methods of assessing NK cell cytolytic activity are known in the art. Conditions suitable for such assays also are well known. A typical chromium release assay is performed by labeling target cells (e.g., Cw3 and/or Cw4 positive cell lines—at about, e.g., 5000 cells per well in a microtitration plate) with $Na_2^{51}CrO_4$ (such that $^{51}Cr$ is taken up and retained by viable target cells), washing to remove excess radioactivity, thereafter exposed to NK cells for a period of about 4 hours in the presence or absence of Anti-KIR Antibody(s) at a suitable effector:target ratio (e.g., about 4:1), and measuring for subsequent $^{51}Cr$ levels reflecting target cell death and lysis. An example of such an assay is described in, e.g., Moretta et al., 1993, J Exp Med 178, 597-604. In a similar assay, proliferating target cells can be labeled with $^3H$-thymidine, which is incorporated into the replicating DNA. Upon cytolytic action by NK cells, the DNA of the target cells is rapidly fragmented and retained in a filtrate, while large, unfragmented DNA can be collected on a filter, such that one can measure either the release of these fragments or the retention of $^3H$-thymidine in cellular DNA. Other examples and relevant discussion related to such assays can be found in, e.g., Fridberg et al., Methods, 1996 April; 9(2):316-26 and Motzer et al., Biological Research for Nursing, 2003, vol. 5, no. 2, pp. 142-152(11)). Other examples of NK cell cytolytic activity assays also are known in the art (see, e.g., Vizier et al., Cytometry. 2002 Mar. 1; 47(3):158-62; Wahlberg et al., J Immunol Methods. 2001 Jul. 1; 253(1-2):69-81; Zons et al., Clin Diagn Lab Immunol. 1997 March; 4 (2): 202-207; Marcusson-Stahl at al., Toxicology. 2003 Dec. 1; 193(3):269-79; Kantakamalakul et al., J Immunol Methods. 2003 Jan. 15; 272(1-2):189-97; Lehmann et al., Cancer Immunol Immunother. 1999 July; 48(4):209-13; Goldberg et al., J Immunol Methods. 1999 Apr. 22; 224(1-2):1-9; Borella et al., J Immunol Methods. 1995 Oct. 12; 186(1):101-10; Lovgren et al., J Immunol Methods. 1994 Jul. 12; 173(1): 119-25); Dinota et al., J Immunol Methods. 1988 Nov. 10; 114(1-2):53-9; and Hoshino et al., J Clin Lab Immunol. 1991 September; 36(1):39-43). Thus, for example, $KIR2DL1^+NK$ cells that display little, if any, cytolytic activity against target cells expressing HLA-Cw4, are expected to show significant increases in such activity by way of such assays when allowed to act in the presence of an anti-KIR antibody comprising KIR-binding sequences from or similar to DF200 and/or NKVSF1.

One illustrative feature of this aspect of the invention is embodied in the provision of Anti-KIR antibodies that specifically bind both KIR2DL1 and KIR2DL2/3 human receptors and reverse inhibition of NK cell cytotoxicity mediated by these inhibitory KIRs (and, e.g., their use in the various combination compositions and therapies of the invention, such as in an anti-cancer combination therapy using one or more of the additional agents described herein). Anti-KIR antibodies comprising KIR-binding sequences from antibody DF200 are an example of such an embodiment. Neutralizing Anti-KIR antibodies comprising KIR-binding sequences that are highly similar to KIR-binding sequences of DF200 are another aspect of the invention (e.g., the invention provides Anti-KIR antibodies comprising KIR-binding sequence(s) that is/are at least about 40%, at least about 50%, at least about 60%, at least about 70%, at least about 80%, at least about 90% or more (e.g., about 55-99%) identical to similar sequences in DF200). In another aspect, the invention provides an anti-KIR antibody that competes with DF200 for binding to its cognate KIRs. In another aspect, the invention provides an antibody that competes with antibody 1-7F9 for binding to its cognate KIRs. DF200 or 1-7F9 and antibodies derived from these antibodies and antibody fragments sharing features with these antibodies also can be used in the various combination therapies and compositions of the invention.

In another exemplary aspect, the invention provides Anti-KIR antibodies that specifically inhibit the binding of MHC molecules to KIR receptors. In one exemplary aspect, the invention provides Anti-KIR antibodies that specifically inhibit the binding of HLA-C molecules to KIR2DL1 and KIR2DL2/3 receptors.

iii. Competition with Cross-Reactive and/or Neutralizing Anti-KIR Antibodies

In another aspect, the invention provides Anti-KIR Antibodies characterized by the ability to compete with cross-reactive and/or neutralizing anti-KIR antibodies for binding to cognate KIRs and/or to bind to the same antigenic determinant region/epitope as such known antibodies. For example, in one aspect the invention provides an anti-KIR Antibody characterized by its ability to compete with antibody NKVSF1 and/or antibody DF200.

The phrase "competes with" when referring to a particular monoclonal antibody (e.g. DF200, NKVSF1, etc.) means that the Anti-KIR Antibody competes with the referenced antibody or other molecule in a binding assay using either recombinant KIR molecules or surface expressed KIR molecules. For example, if an anti-KIR Antibody detectably reduces binding of DF200 to a KIR molecule normally bound by DF200 in a binding assay, the Anti-KIR Antibody can be said to "compete" with DF200. An anti-KIR Antibody that "competes" with DF200 may compete with DF200 for binding to the KIR2DL1 human receptor, the KIR2DL2/3 human receptor, or both KIR2DL1 and KIR2DL2/3 human receptors.

Although often related, describing a protein in terms of competition with a reference binding protein versus the ability of the protein to bind to the same or substantially similar epitope as a reference protein in some cases imply significantly different biological and physiochemical properties. Competition between binding proteins implies that the test Anti-KIR Antibody binds to an epitope that at least partially overlaps with an epitope bound by an anti-KIR antibody or is located near enough to such an epitope so that such an Anti-KIR Antibody competes with known anti-KIR antibodies due to steric hindrance. A large Anti-KIR Antibody, such as an anti-KIR Antibody that consists of or comprises an antibody, may compete with a reference anti-KIR antibody, without binding to the same or similar epitope due to the large size of the antibodies. Such a competing Anti-KIR Antibody can be useful in blocking interactions associated with the same antigenic determining region as the reference anti-KIR antibody even though it binds a different antigenic determinant.

In an exemplary aspect, the invention provides an anti-KIR Antibody that binds both KIR2DL1 and KIR2DL2/3 human receptors, reverses inhibition of NK cell cytotoxicity mediated by these KIRs, and competes with DF200 and/or NKVSF1 for binding to the KIR2DL1 human receptor, the KIR2DL2/3 human receptor, or both KIR2DL1 and KIR2DL2/3 human receptors.

In another exemplary aspect, the invention provides an anti-KIR Antibody that binds to substantially the same antigenic determinant region as an anti-KIR antibody, such as DF200 and/or NKVSF1.

In another exemplary aspect, the invention provides Anti-KIR antibodies that bind to one or more KIR2DS proteins, without binding to any inhibitory KIR2DL receptors.

Competition refers to any significant reduction in the propensity for a particular molecule to bind a particular binding partner in the presence of another molecule that binds the binding partner. Typically, competition means an at least about 15% reduction in binding, such as an at least about 20% reduction in binding (e.g., a reduction in binding of about 25% or more, about 30% or more, about 15-35%, etc.) between, e.g., an anti-KIR antibody and at least one KIR in the presence of the competing molecule, e.g., an anti-KIR Antibody. In certain situations, such as in cases where epitopes belonging to competing antibodies are closely located in an antigen, competition can be marked by greater than about 40% relative inhibition of receptor (e.g., KIR) binding, at least about 50% inhibition, at least about 55% inhibition, at least about 60% inhibition, at least about 75% inhibition, or higher level of inhibition (such as a level of inhibition of about 45-95%).

Assessing competition typically involves an evaluation of relative inhibitory binding using a first amount of a first molecule (e.g., an anti-KIR Antibody); a second amount of a second molecule (e.g., a known anti-KIR antibody); and a third amount of a third molecule (e.g., a KIR), wherein the first, second, and third amounts all are sufficient to make a comparison that imparts information about the selectivity and/or specificity of the molecules at issue with respect to the other present molecules. Usually, for ELISA competition assays, about 5-50 µg (e.g., about 10-50 µg, about 20-50 µg, about 5-20 µg, about 10-20 µg, etc.) of an anti-KIR Antibody, a known anti-KIR antibody, and at least one KIR are used to assess whether competition exists. Conditions also should be suitable for binding of the competing molecules to their putative/known target. Physiological or near-physiological conditions (e.g., temperatures of about 20-40° C., pH of about 7-8, etc.) can typically be suitable for Anti-KIR Antibody:KIR.

The identification of one or more molecules that compete with and/or that bind(s) to substantially or essentially the same antigenic determinant region or epitope as an anti-KIR antibody can be readily determined using any one of a variety of immunological screening assays in which antibody competition can be assessed. A number of such assays are routinely practiced and well known in the art (see, e.g., U.S. Pat. No. 5,660,827).

Determination of competition (or relative inhibition of binding) between two or more molecules can be made by use of immunoassays in which the control KIR-binding molecule (antibody DF200, for example) and test Anti-KIR Antibody are admixed (or pre-adsorbed) and applied to a sample containing relevant KIRs, such as both KIR2DL1 and KIR2DL2/3 (each of which is known to be bound by DF200). Protocols based upon ELISAs, radioimmunoassays, Western blotting, and the like are suitable for use in such competition studies. Competition ELISAs are typically performed under conditions suitable for binding of the molecules (e.g., physiological conditions, particularly in the case of antibodies that bind conformational/nonlinear epitopes).

Competition also can be assessed by, for example, a flow cytometry test. In such a test, cells bearing a given KIR can be incubated first with an anti-KIR antibody or other KIR-binding protein (DF200, for example) and then with an anti-KIR Antibody labeled with a fluorochrome or biotin. The Anti-KIR Antibody can be said to compete with DF200 if the binding obtained upon pre-incubation with saturating amount of DF200 is about 80% or less, such as about 50% or less, about 40% or less (e.g., about 30% or less) or any other suitable amount (e.g., about 15-95%) of the KIR binding by the Anti-KIR Antibody (as measured by mean of fluorescence) without pre-incubation with DF200. Alternatively, an anti-KIR Antibody can be said to compete with a known anti-KIR antibody, such as DF200, if the binding obtained with a labeled antibody (by a fluorochrome or biotin) on cells pre-incubated with saturating amount of an anti-KIR Antibody is about 80% or less, such as less than about 50%, less than about 40%, or less (e.g., about 30% or less) or any other suitable amount (e.g., about 15-95%) of the binding obtained by the labeled anti-KIR antibody without pre-incubation with the Anti-KIR Antibody.

Competition also or alternatively can be assessed by SPR analysis. In such an assay, relevant KIRs (e.g., KIR2DL1 and/or KIR2DL2/3) are immobilized to the surface of a BIACORE chip (or other media suitable for surface plasmon resonance analysis). The control antibody (e.g., DF200) is then brought into contact with the surface at saturating concentration and the KIR binding of the control antibody measured. This binding of the control antibody is compared with the binding of the control antibody to the KIR-bound surface in the presence of the test Anti-KIR Antibody. In a test assay, a significant reduction in binding of the KIR-containing surface by the control antibody in the presence of a test antibody indicates that the test Anti-KIR Antibody recognizes substantially the same epitope as the control antibody such that the test Anti-KIR Antibody competes with the control antibody. It will be appreciated that the order of control antibody and test Anti-KIR Antibody reaction with the immobilized KIR(s) can be reversed: that is the control antibody can be first bound to the surface and the test Anti-KIR Antibody can be brought into contact with the surface thereafter in a competition assay. Preferably, the molecule believed to have higher affinity for KIR(s) is bound to the surface first, as it will be expected that the decrease in binding seen for the second molecule will be of greater magnitude. Further examples of such assays are provided in, e.g., Saunal and Regenmortel, (1995) J. Immunol. Methods 183: 33-41. Typically suitable levels of competition (e.g., 15-85% or less binding of a molecule in the presence of the competing molecule) are described above and can be generally applied to the competition assay methods described herein.

Additional methods for determining mAb specificity by competitive inhibition are known in the art and useful examples of such techniques can be found in, e.g., Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), Ausubel et al., Eds., Short Protocols in Molecular Biology, ($5^{th}$ edition), John Wiley & Sons (2002), and Muller, Meth. Enzymol. 92:589-601 (1983)).

An antigenic determinant region or epitope can be identified by a number of known techniques. For example, an antigenic determinant region can be identified quickly by "foot printing" assays, such as through a chemical modification of the exposed amines/carboxyls in target KIRs, such as in the KIR2DL1 or KIR2DL2/3 proteins. One specific example of such a foot-printing technique is the use of HXMS (hydrogen-deuterium exchange detected by mass spectrometry), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H. Analytical Biochemistry, Vol. 267 (2) pp. 252-259 (1999) and/or Engen, J. R. and Smith, D. L. (2001) Anal. Chem. 73, 256A-265A.

Another example of a suitable epitope identification technique is nuclear magnetic resonance (NMR) epitope mapping, where typically the position of the signals in two-dimensional NMR spectres of the free antigen and the antigen complexed with the antigen-binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3): 516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR-binder can subsequently be identified by comparison of samples subjected to trypsin digestion and samples incubated with antibody and then subjected to digestion by e.g. trypsin (thereby revealing a foot print for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR2DL1 in the context of an anti-KIR polypeptide that is not surface exposed and, accordingly, most likely not relevant in terms of antigenicity. See, e.g., Manca, Ann 1st Super Sanita. 1991; 27(1):15-9 for a discussion of similar techniques.

Various phage display techniques also can be used to identify epitopes. See, e.g., Wang and Yu, Curr Drug Targets. 2004 January; 5(1):1-15; Burton, Immunotechnology. 1995 August; 1(2):87-94; Cortese et al., Immunotechnology. 1995 August; 1(2):87-94; and Irving et al., Curr Opin Chem. Biol. 2001 June; 5(3):314-24. Consensus epitopes also can be identified through modified phage display-related techniques (see, Mumey et al., *J. Comput. Biol.* 10:555-567 and Mumey, *Proceedings of the Sixth Annual International Conference on Computational Molecular Biology* (RECOMB-02), pp. 233-240 (ACM Press, New York)) for discussion (see also Bailey et al., *Protein Science* (2003), 12:2453-2475; Dromey et al., J Immunol. 2004 Apr. 1; 172(7):4084-90; Parker et al., Mol. Biotechnol. 2002 January; 20(1):49-62; and Czompoly et al., Biochem Biophys Res Commun. 2003 Aug. 8; 307(4):791-6).

Epitope mapping by competitive binding to a KIR with two KIR-binding molecules where one is biotinylated (e.g., a known anti-KIR antibody) or otherwise similarly labeled is another method for identifying relevant antigenic determinant regions.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology.

Computer-based methods such as sequence analysis and three dimensional structure analysis and docking also can be used to identify antigenic determinants. For example, an epitope also can be determined by molecular modeling using a structure of a KIR or portion thereof with docking of the structure of the Fab fragment of an individual mAb. Where necessary, models of KIRs can be produced by homology modeling with structure-characterized KIRs using programs such as MOE (Molecular Operating Environment), which is available from Chemical Computing Group (Montreal, Quebec, Canada—See Worldwide Website: chemcomp.com). These and other mapping methods are discussed in Epitope Mapping A Practical Approach (Westwood and Hay Eds.) 2001 Oxford University Press (see also, Cason, J Virol Methods. 1994 September; 49(2):209-19).

In additional aspects, the invention provides Anti-KIR Antibodies that are directed to particular antigenic regions and/or epitopes presented on various KIRs. In one exemplary aspect, the invention provides Anti-KIR Antibodies that specifically bind KIR2DL1 within a region defined by one or more of the amino acid residues selected from 105, 106, 107, 108, 109, 110, 111, 127, 129, 130, 131, 132, 133, 134, 135, 152, 153, 154, 155, 156, 157, 158, 159, 160, 161, 162, 163, 181, and 192. In another embodiment the invention provides Anti-KIR Antibodies that specifically bind to KIR2DL1 and KIR 2DL2/3 in a region defined by one or more of amino acid residues 105, 106, 107, 108, 109, 110, 111, 127, 129, 130, 131, 132, 133, 134, 135, 152, 153, 154, 155, 156, 157, 158, 159, 160, 161, 162, 163, 181, and 192 thereof.

In a further aspect, the invention provides Anti-KIR Antibodies that bind to KIR2DL1, but that bind to a mutant of KIR2DL1 in which R131 is Ala with significantly reduced binding affinity relative thereto (about 20% or less, about 30% or less, about 40% or less, about 50% or less, about 60% or less, about 70% or less, etc., of the affinity exhibited for KIR2DL1). In another aspect, the invention provides Anti-KIR Antibodies that bind to KIR2DL1 but that which bind to a mutant of KIR2DL1 in which R157 is Ala with relatively reduced binding affinity (about 20% or less, about 30% or less, about 40% or less, about 50% or less, about 60% or less, about 70% or less, etc., of the affinity exhibited for KIR2DL1). In another aspect, the invention provides Anti-KIR Antibodies that bind to KIR2DL1 and which binds a mutant of KIR2DL1 in which R158 is Ala with relatively reduced binding affinity (about 20% or less, about 30% or less, about 40% or less, about 50% or less, about 60% or less, about 70% or less, etc., of the affinity exhibited for KIR2DL1).

In a further aspect, the invention provides Anti-KIR Antibodies that bind to KIR2DL1 residues 131, 157, and 158.

In an additional aspect, the invention provides Anti-KIR Antibodies that bind to KIR2DS3(R131W), but not to wild type KIR2DS3. In yet another aspect, the invention provides Anti-KIR Antibodies that bind to KIR2DL1 and KIR2DL2/3 as well as KIR2DS4. In still another aspect, the invention provides Anti-KIR Antibodies that bind to both KIR2DL1 and KIR2DL2/3, but not to KIR2DS4.

To illustrate the use of anti-KIR antibody sequences in the composition and construction of Anti-KIR Antibodies, exemplary anti-KIR antibody sequences and antibody sequence variants will be described here.

In one exemplary aspect, the invention provides an anti-KIR Antibody comprising a CDR-L1 sequence that consists or consists essentially of the sequence Lys Ala Ser Gln Asn Val Val Thr Tyr Val Ser (SEQ ID NO:21). In another aspect, the invention provides an anti-KIR Antibody that comprises a CDR-L1 that consists or consists essentially of the sequence Thr Ala Ser Ser Ser Val Ser Ser Ser Tyr Leu Tyr (SEQ ID NO:4).

In another illustrative aspect, the invention provides an anti-KIR antibody that also or alternatively comprises a CDR-L2 sequence that consists or consists essentially of the sequence Gly Ala Ser Asn Arg Tyr Thr (SEQ ID NO:5). In a further aspect, the invention provides an anti-KIR antibody that also or alternatively comprises a CDR-L2 that consists or consists essentially of the sequence Ser Thr Ser Asn Leu Ala Ser (SEQ ID NO:6).

In another demonstrative facet, the invention provides an anti-KIR antibody that also or alternatively comprises a CDR-L3 that consists or consists essentially of the sequence Gly Gln Gly Tyr Ser Tyr Phe Tyr Thr (SEQ ID NO:22). In yet another aspect, the invention provides an anti-KIR antibody that also or alternatively comprises a CDR-L3 that consists or consists essentially of the sequence His Gln Tyr His Arg Ser Pro Pro Thr (SEQ ID NO:8).

As a further exemplary feature, the invention provides an anti-KIR antibody that comprises a CDR-H1 that consists or consists essentially of the sequence Gly Phe Ser Phe Thr Phe Tyr Gly Val His (SEQ ID NO:23).

In still another exemplary aspect, the invention provides an anti-KIR antibody that comprises a CDR-H2 that consists or consists essentially of the sequence Val Ile Trp Ser Gly Gly Asn Thr Asp Tyr Asn Ala Ala Phe Ile Ser (SEQ ID NO:11).

In yet another exemplary aspect, the invention provides an anti-KIR antibody that comprises a CDR-H3 that consists or consists essentially of the sequence Asn Pro Arg Pro Gly Asn Tyr Pro Tyr Gly Met Asp Tyr (SEQ ID NO:12).

In a different aspect, the invention provides an anti-KIR antibody that comprises a CDR-H1 that consists or consists essentially of the sequence Gly Tyr Thr Phe Thr Ser Tyr Trp Met His (SEQ ID NO:24).

In an additional aspect, the invention provides an anti-KIR antibody that comprises a CDR-H2 that consists or consists essentially of the sequence Thr Ile Tyr Pro Gly Asn Ser Asp Thr Asn Tyr Asn Gln Lys Phe Lys Gly (SEQ ID NO:25).

Another aspect of the invention is embodied by an anti-KIR antibody that comprises a CDR-H3 that consists or consists essentially of the sequence Pro Thr Thr Ala Thr Arg Ser Ser Ala Met Asp Tyr (SEQ ID NO:26).

The basic and novel properties of these CDR sequences is the ability to, in combination with other necessary CDR and FR sequences, bind to epitope(s) presented on one or more KIRs. As indicated above, it may be the case that certain residues in such sequences contribute little or nothing to KIR epitope binding. Moreover, it also or alternatively may be the case that such CDR sequences may tolerate one or a few insertions without impacting their epitope binding characteristics substantially (specificity and/or affinity). However, in another aspect of the invention significant changes can be made in such sequences to produce useful variants. Such changes are discussed further below.

These exemplary CDR sequences can be combined with one another, variant CDR sequences described below, or other anti-KIR CDRs (typically from KIR-binding anti-KIR antibodies). In one exemplary aspect, the invention provides an anti-KIR antibody that comprises most or all of the CDR sequences selected from SEQ ID NOS:1, 3, 5, 7, 8, and 9 SEQ ID NOS:1, 5, 22, 23, 11 and 12.

In another illustrative aspect, the invention provides an antibody comprising a light variable (VL) sequence consisting essentially of the sequence Met Glu Ser Gln Thr Leu Val Phe Ile Ser Ile Leu Leu Trp Leu Tyr Gly Ala Asp Gly Asn Ile Val Met Thr Gln Ser Pro Lys Ser Met Ser Met Ser Val Gly Glu Arg Val Thr Leu Thr Cys Lys Asn Ser Glu Asn Val Val Thr Tyr Val Ser Trp Tyr Gln Gln Lys Pro Glu Gln Ser Pro Lys Leu Leu Ile Tyr Gly Ala Ser Asn Arg Tyr Thr Gly Val Pro Asp Arg Phe Thr Gly Ser Gly Ser Ala Thr Asp Phe Thr Leu Thr Ile Ser Ser Val Gln Ala Glu Asp Leu Ala Asp Tyr His Cys Gly Gln Gly Tyr Ser Tyr Pro Tyr Thr Phe Gly Gly Thr Lys Leu Asp Ile Lys Arg (SEQ ID NO:27). The basic and novel properties of such a sequence are its contribution to KIR binding. It may be possible that some amino acids can be deleted, add, or substituted in this sequence without substantial impact to such properties.

In an additional exemplary aspect, the invention provides an antibody comprising a VL sequence consisting essentially of the sequence Met Asp Phe Gln Val Gln Ile Phe Ser Phe Leu Leu Ile Ser Ala Ser Val Ile Met Ser Arg Gly Gln Ile Val Leu Thr Gln Ser Pro Ala Ser Met Ser Ala Ser Leu Gly Glu Arg Val Thr Met Thr Cys Thr Ala Ser Ser Ser Val Ser Ser Ser Tyr Leu Tyr Trp Tyr Gln Gln Lys Pro Gly Ser Ser Pro Lys Leu Trp Ile Tyr Ser Thr Ser Asn Leu Ala Ser Gly Val Pro Ala Arg Phe Ser Gly Ser Gly Ser Gly Thr Ser Tyr Ser Leu Thr Ile Ser Ser Met Gln Ala Glu Asp Ala Ala Thr Tyr Tyr Cys His Gln Tyr His Arg Ser Pro Pro Thr Phe Gly Gly Gly Thr Lys Leu Glu Ile Lys Arg (SEQ ID NO:28).

The N-terminal portion of both SEQ ID NO:27 and SEQ ID NO:28 may be cleaved in a suitable host cell if the sequence is presented in an appropriate context (e.g., the first about 23 amino acids of SEQ ID NO:27 may be cleaved after acting as a signal sequence for the VL sequence where it is the entire content of the peptide at issue or represents an exposed N-terminal portion of a peptide). Accordingly, the invention also provides Anti-KIR antibodies comprising VL sequences consisting essentially of N-terminal truncated versions of SEQ ID NO:27 and SEQ ID NO:28 (e.g., where about 20 amino acids of the N-terminal portion thereof have been removed).

In another aspect, the invention provides an anti-KIR antibody that also or alternatively comprises a variable heavy (VH) sequence consisting essentially of the sequence Met Ala Val Leu Gly Leu Leu Phe Cys Leu Val Thr Phe Pro Ser Cys Val Leu Ser Gln Val Gln Leu Glu Gln Ser Gly Pro Gly Leu Val Gln Pro Ser Gln Ser Leu Ser Ile Thr Cys Thr Val Ser Gly Phe Ser Phe Thr Pro Tyr Gly Val His Trp Val Arg Gln Ser Pro Gly Lys Gly Leu Glu Trp Leu Gly Val Ile Trp Ser Gly Gly Asn Thr Asp Tyr Asn Ala Ala Phe Ile Ser Arg Leu Ser Ile Asn Lys Asp Asn Ser Lys Ser Gln Val Phe Phe Lys Met Asn Ser Leu Gln Val Asn Asp Thr Ala Ile Tyr Tyr Cys Ala Arg Asn Pro Arg Pro Gly Asn Tyr Pro Tyr Gly Met Asp Tyr Trp Gly Gln Gly Thr Ser Val Thr Val Ser Ser (SEQ ID NO:9). The first 20 amino acid residues of this sequence can act as a signal sequence for a peptide consisting or consisting essentially of this sequence or a protein chain comprising this sequence positioned in an appropriate context. Accordingly, the invention also provides an anti-KIR antibody that comprises a VH sequence that consists essentially of a fragment of SEQ ID NO:9—DITTO AS ABOVE COMMENT that lacks the first about 1-20 residues thereof.

In further aspect, the invention provides an anti-KIR antibody that also or alternatively comprises a variable heavy (VH) sequence consisting essentially of the sequence Met Glu Cys Asn Trp Ile Leu Pro Phe Ile Leu Ser Val Thr Ser Gly Val Tyr Ser Glu Val Gln Leu Gln Gln Ser Gly Thr Val Leu Ala Arg Pro Gly Ala Ser Val Lys Met Ser Cys Lys Ala Ser Gly Tyr Thr Phe Thr Ser Tyr Trp Met His Trp Met Lys Gln Arg Pro Gly Gln Gly Leu Glu Trp Ile Gly Thr Ile Tyr Pro Gly Asn Ser Asp Thr Asn Tyr Asn Gln Lys Phe Lys Gly Lys Ala Lys Leu Thr Ala Val Thr Ser Thr Asn Thr Ala Tyr Met Glu Leu Ser Ser Leu Thr Asn Glu Asp Ser Ala Val Tyr Tyr Cys Ser Arg Pro Thr Thr Ala Thr Arg Ser Ser Ala Met Asp Tyr Trp Gly Gln Gly Thr Ser Val Thr Val Ser Ser (SEQ ID NO:29). The first 20 amino acid residues of this sequence can act as a signal sequence for a peptide consisting or consisting essentially of this sequence or a protein chain comprising this sequence positioned in an appropriate context. Accordingly, the invention also provides an anti-KIR antibody that comprises a VH sequence that consists essentially of a fragment of SEQ ID NO:29 that lacks about the first 1-20 residues thereof.

In one aspect, the invention provides an anti-KIR antibody that comprises a VL sequence that consists essentially of SEQ ID NO:27 or an N-terminal truncated portion thereof and a VH sequence that consists essentially of SEQ ID NO:9 or an N-terminal truncated portion thereof.

As already mentioned, suitable sequence variants of antigen-binding antibody sequences, such as anti-KIR antibody sequences, can be incorporated into antibodies of the invention. Variations in most types of antibody sequence may be suitable. Thus, for example, an Anti-KIR antibody can comprise variant constant sequences and/or variant framework sequences.

In one aspect, the invention provides a an Anti-KIR antibody that comprises one or more variant CDR sequences (i.e., a CDR sequence that differs from similar wild-type CDR sequence by one or more amino acid insertions, deletions, additions, and/or substitutions that impact the biological and/or physiochemical properties of the sequence with respect to its wild-type relative sequence). There are a number of techniques known for generating CDR variants, any suitable technique or combination of which can be used in the context of this invention. Examples of such techniques include the removal of nonessential residues as described in, e.g., Studnicka et al., Protein Engineering, Vol 7, 805-814 (1994) (see also Soderlind et al., Immunotechnology. 1999 March; 4(3-4):279-85), CDR walking mutagenesis and other artificial affinity maturation techniques (see, e.g., Journal of Molecular Biology, December 1995; 254(3):392-403), CDR shuffling techniques wherein typically CDRs are amplified from a diverse set of gene templates optionally comprising synthetic oligonucleotides, the constant regions of the VL, VH, and/or CDRs are amplified, and the various fragments mixed (in single-stranded or double-stranded format) and assembled by polymerase chain reaction (PCR) to produce a set of antibody-fragment encoding gene products carrying shuffled CDR introduced into the master framework, which is amplified using external primers annealing to sites beyond inserted restriction sites to ensure production of full-length products, which are inserted into a vector of choice and used to expressed variant CDR-containing proteins. Appropriate structure can be determined by superimposition of the variant/mimetic structures and those of the parent sequences, e.g., by comparison of NMR solution structures. Additional examples of such methods are provided elsewhere herein.

CDR, VH, and VL sequence variants can exhibit any suitable level of identity to one or more "parent" CDR, VH, and VL sequences, respectively, such as the CDR, VH, and VL sequences of anti-KIR mAb DF200 and/or anti-KIR mAb NKVSF1. Typically, a variant sequence that binds to an essentially identical antigenic determinant region as a parent will retain at least about 40% amino acid sequence identity to the parent sequence, such as about 50% or more, about 60% or more, about 70% or more, about 75% or more, about 80% or more, about 85% or more, about 90% or more, or at least about 95% (e.g., about 45-99%, about 55-99%, or about 65-99%) identity to the parent sequence. However, in some cases, particularly with respect to CDR sequences targeted to an essentially identical epitope, variants with even lower levels of identity can be suitable.

CDR, VH, and VL sequence variants that bind to different antigenic determinant regions or a different set (or "profile") of antigenic determinant regions also can be generated by any of the techniques described elsewhere herein (rational design, mutagenesis, directed evolution, etc.). In such instances, significantly lower levels of amino acid sequence identity to a parent sequence can be expected. For example, in the context of a CDR-L1, CDR-H1, CDR-H2, or CDR H3 variant having a different epitope binding profile from a parent sequence, as little as about 20-30% amino acid sequence identity to a parent CDR sequence may be exhibited in variants that contribute to binding of NKCAMRs, such as KIRs.

Typically, variants differ from "parent" sequences mostly through conservative substitutions; e.g., at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of this invention, conservative substitutions can be defined by substitutions within the classes of amino acids reflected in one or more of the following three tables:

TABLE 4

Amino Acid Residue Classes for Conservative Substitutions

| Amino Acid Class | Amino Acid Residues |
| --- | --- |
| Acidic Residues | ASP and GLU |
| Basic Residues | LYS, ARG, and HIS |
| Hydrophilic Uncharged Residues | SER, THR, ASN, and GLN |
| Aliphatic Uncharged Residues | GLY, ALA, VAL, LEU, and ILE |
| Non-polar Uncharged Residues | CYS, MET, and PRO |
| Aromatic Residues | PHE, TYR, and TRP |

TABLE 5

Alternative Conservative Amino Acid Residue Substitution Groups

| | | | |
| --- | --- | --- | --- |
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) |
| 6 | Phenylalanine (F) | Tyrosine (Y) | Tryptophan (W) |

TABLE 6

Further Alternative Physical and Functional Classifications of Amino Acid Residues

| | |
| --- | --- |
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | E, Q, T, K, S, G, P, D, E, and R |

More conservative substitutions groupings include: valine-leucine-isoleucine, phenylalanine-tyrosine, lysine-arginine, alanine-valine, and asparagine-glutamine. Additional groups of amino acids can also be formulated using the principles described in, e.g., Creighton (1984) Proteins: Structure and Molecular Properties (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Substantial changes in function can be made by selecting substitutions that are less conservative than those shown in the defined groups, above. For example, non-conservative substitutions can be made which more significantly affect the structure of the peptide in the area of the alteration, for example, the alpha-helical, or beta-sheet structure; the charge or hydrophobicity of the molecule at the target site; or the bulk of the side chain. The substitutions which generally are expected to produce the greatest changes in the peptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine. Accordingly, these and other nonconservative substitutions can be introduced into peptide variants where significant changes in function/structure is desired and such changes avoided where conservation of structure/function is desired.

Those skilled in the art will be aware of additional principles useful in the design and selection of peptide variants. For example, residues in surface positions of a peptide typically a strong preference for hydrophilic amino acids. Steric properties of amino acids can greatly affect the local structures that a protein adopts or favors. Proline, for example, exhibits reduced torsional freedom that can lead to the conformation of the peptide backbone being locked in a turn and with the loss of hydrogen bonding, often further resulting in the residue appearing on a surface loop of a protein. In contrast to Pro, Gly has complete torsional freedom about a main peptide chain, such that it is often associated with tight turns and regions buried in the interior of the protein (e.g., hydrophobic pockets). The features of such residues often limit their involvement in secondary structures. However, residues typically involved in the formation of secondary structures are known. For example, residues such as Ala, Leu, and Glu (amino acids without much bulk and/or polar residues) typically are associated with alpha-helix formation, whereas residues such as Val, Ile, Ser, Asp, and Asn can disrupt alpha helix formation. Residues with propensity for beta-sheet structure formation/ inclusion include Val and Ile and residues associated with turn structures include Pro, Asp, and Gly. The skilled artisan can consider these and similar known amino acid properties in the design and selection of suitable peptide variants, such that suitable variants can be prepared with only routine experimentation.

Desirably, conservation in terms of hydropathic/hydrophilic properties also is substantially retained in a variant peptide as compared to a parent peptide (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 65-99%) retained). Methods for assessing the conservation of the hydropathic character of residues/sequences are known in the art and incorporated in available software packages, such as the GREASE program available through the SDSC Biology Workbench (see also, e.g., Kyte and Doolittle et al., J. Mol. Biol. 157:105-132 (1982); Pearson and Lipman, PNAS (1988) 85:2444-2448, and Pearson (1990) Methods in Enzymology 183:63-98 for a discussion of the principles incorporated in GREASE and similar programs).

It also typically is advantageous that structure of the variant peptide is substantially similar to the structure of the parent peptide. Methods for assessing similarity of peptides in terms of conservative substitutions, hydropathic properties, weight conservation, and similar considerations are described in e.g., International Patent Applications WO 03/048185, WO 03/070747, and WO 03/027246. Secondary structure comparisons can be made using the EBI SSM program (currently available at Worldwide Website: ebi-.ac.uk/msd-srv/ssm/). Where coordinates of the variant are known they can be compared by way of alignment/comparison programs such as DALI pair alignment (currently available at Worldwide Website: ebi.ac.uk/dali/Interactive.html), TOPSCAN (currently available at Worldwide Website: bio-inf.org.uk/topscan), COMPARER (currently available at Worldwide Website: cryst.bioc.cam.ac.uk/COMPARER/) PRIDE pair (currently available at Worldwide Website: hydra.icgeb.trieste.it/pride/pride.php?method=pair), PINTS (currently available at Worldwide Website: russell.embl.de/ pints/), SARF2 (currently available at Worldwide Website: 123d.ncifcrf.gov/run2.html), the Structural Alignment Server (currently available at Worldwide Website: molmovdb.org/align/), and the CE Calculate Two Chains Server (currently available at Worldwide Website: cl.sdsc.edu/ce/ ce_align.html). Ab initio protein structure prediction methods can be applied, if needed, to the variant sequence, such as through the HMM-ROSETTA or MODELLER programs, to predict the structure for comparison with the parent sequence(s) molecule. Where appropriate other structure prediction methods, such as threading methods, also or alternatively can be used, to predict the structure of the variant and/or parent sequence proteins.

The retention of similar residues also or alternatively can be measured by a similarity score, as determined by use of a BLAST program (e.g., BLAST 2.2.8 available through the NCBI). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

As discussed elsewhere herein, other points of variation/ divergence between a variant and a parent can be acceptable (e.g., inclusion of non-naturally-occurring amino acids, derivatized amino acids, insertions, deletions, and extensions to the sequence, etc.) provided that such changes do not substantially impair the ability of the variant to bind the target antigen as compared to the parent peptide.

Identity in the context of amino acid sequences of the invention can be determined by any suitable technique, typically by a Needleman-Wunsch alignment analysis (see Needleman and Wunsch, J. Mol. Biol. (1970) 48:443-453), such as is provided via analysis with ALIGN 2.0 using the BLOSUM50 scoring matrix with an initial gap penalty of −12 and an extension penalty of −2 (see Myers and Miller, CABIOS (1989) 4:11-17 for discussion of the global alignment techniques incorporated in the ALIGN program). A copy of the ALIGN 2.0 program is available, e.g., through the San Diego Supercomputer (SDSC) Biology Workbench. Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (J. Mol. Biol. (1981) 147:195- 197), which can be obtained through available programs (other local alignment methods that may be suitable for analyzing identity include programs that apply heuristic local alignment algorithms such as FastA and BLAST programs). Further related methods for assessing identity are described in, e.g., International Patent Application WO 03/048185. The Gotoh algorithm, which seeks to improve upon the Needleman-Wunsch algorithm, alternatively can be used for global sequence alignments. See, e.g., Gotoh, J. Mol. Biol. 162:705-708 (1982).

Typically, advantageous sequence changes are those that (1) reduce susceptibility to proteolysis, (2) reduce susceptibility to oxidation, (3) alter binding affinity of the variant sequence (typically desirably increasing affinity), and/or (4) confer or modify other physicochemical or functional properties on the associated variant/analog peptide. In the context of CDR and FR region variants, it is typically desired that residues required to support and/or orientate the CDR structural loop structure(s) are retained; that residues which fall within about 10 angstroms of a CDR structural loop (but optionally only residues in this area that also possess a water solvent accessible surface of about 5 angstroms$^2$ or greater) are unmodified or modified only by conservative amino acid residue substitutions; and/or that the sequence is subject to only a limited number of insertions and/or deletions (if any), such that CDR structural loop-like structures are retained in the variant (a description of related techniques and relevant principles is provided in, e.g., Schiweck et al., J Mol. Biol. 1997 May 23; 268(5):934-51; Morea, Biophys Chem. 1997 October; 68(1-3):9-16; Shirai et al., FEBS Lett. 1996 Dec. 9; 399(1-2):1-8; Shirai et al., FEBS Lett. 1999 Jul. 16; 455(1-2):188-97; Reckzo et al., Protein Eng. 1995 April; 8(4):389-95; and Eigenbrot et al., J Mol. Biol. 1993 Feb. 20; 229(4): 969-95).

As already mentioned, amino acid sequence variations can result in an altered glycosylation pattern in the variant antibody sequence with respect to a parent antibody sequence. "Altering" in this context means removal of one or more glycosylation sites found in the parent antibody and/or adding one or more glycosylation sites that are not present in the parent antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are common recognition sequences for enzymatic attachment of the carbohydrate moiety to the asparagine side chain. Thus, the presence of either of these tripeptide sequences in a polypeptide can create a potential glycosylation site. O-linked glycosylation refers to the attachment of sugars such as N-aceylgalactosamine, galactose, or xylose to a hydroxyamino acid, most commonly serine or threonine, although 5-hydroxyproline or 5-hydroxylysine may also be used. Addition of glycosylation sites to the antibody can be conveniently accomplished by altering the amino acid sequence of the variant with respect to the parent sequence such that it is caused to contain one or more of the above-described tripeptide sequences (for N-linked glycosylation sites) or other suitable glycosylation site. The alteration may also be made by, for example, the addition of, or substitution by, one or more serine or threonine residues to the sequence of the original antibody (for O-linked glycosylation sites).

Using the above-described techniques and other techniques described herein, the invention provides a number of methods for generating useful antibody and antibody-like peptide variants that are similar to one or more "parent" anti-KIR antibody produced by mammals or other chordates (or cells obtained or derived from either thereof—such as a mammalian cell derived hybridoma) in response to immunization with an NKCAMR, NKCAMR portion, or protein comprising NKCAMR sequences (e.g., a KR, KIR portion, or protein comprising KIR sequences).

Amino acid sequence variants generally can be obtained by, for example, introducing appropriate nucleotide changes into an antibody-encoding nucleic acid (e.g., by site directed mutagenesis), by chemical peptide synthesis, or any other suitable technique. Such variants include, for example, variants differing by deletions from, insertions into, additions to (at either end of the parent sequence), and/or substitutions of, residues within the parent amino acid sequences of known anti-KIR antibodies, and within the anti-KIR antibody sequences provided herein. Any combination of deletions, insertions, additions, and substitutions can be made to arrive at a desired variant, provided that the variant possesses suitable characteristics for practice in the methods of the invention (e.g., retention of at least a substantial proportion of the parent antibodies affinity, specificity, and/or selectivity with respect to one or more KIR epitopes). Amino acid sequence changes, with respect to a parent antibody, also may alter post-translational processes of the variant antibody with respect to a parent antibody, such as by changing the number or position of glycosylation sites.

Other potentially suitable techniques for preparing antibody sequence variants include CDR walking mutagenesis, antibody chain shuffling, "parsimonious mutagenesis" (Balint and Larrick Gene 137:109-118 (1993)), and other affinity maturation techniques (see, e.g., Wu et al. PNAS (USA) 95: 6037-6-42 (1998)). Repertoire cloning procedures also can be useful in the production of variant antibodies (see, e.g., International Patent Application WO 96/33279).

Where hypervariable region insertions are made to generate a variant antibody, the typical range of lengths of the hypervariable region in question in known similar antibodies regularly is taken into account. For example, for the first hypervariable region of a light chain variable domain, insertions can be introduced into the CDR L1 sequence of a parent antibody while retaining a substantially similar and thereby expected appropriate size, which according to Kabat et al., supra, e.g., typically has an overall of about 9-20 (e.g., about 10-17) residues. Similarly, CDR L2 typically has an overall length from about 5-10 residues; CDR L3 typically has a length of about 7-20 residues; CDR H1 typically has a length of about 10-15 residues; CDR H2 typically has a length of about 15-20 residues; and CDR H3 typically has a length of about 6-30 residues (e.g., 3-25 residues). Insertions in the VH region typically are made in CDR H3 and typically near the C-terminal of the domain, such as about residues 97-102 of the parent CDR H3 (e.g., adjacent to, and preferably C-terminal in sequence to, residue number 100 of the parent CDR H3 sequence) using the alignment and numbering as described in Kabat. Antibody variants with inserted amino acid residue(s) in a hypervariable region thereof may be prepared randomly, especially where the starting binding affinity of the parent antibody for the target antigen is such that randomly produced antibody variants can be readily screened. For example, phage display provides a convenient method of screening such random variants.

Amino acid sequence insertions include amino- and/or carboxyl-terminal fusions ranging in length from one residue to polypeptides containing a hundred or more residues (sometimes separately referred to as "additions"), as well as intrasequence insertions of single or multiple amino acid residues. Examples of terminal insertions include an antibody with an N-terminal methionyl residue or the antibody fused to an epitope tag. Other insertion variants of the antibody molecule include the fusion to the N- or C-terminus of the antibody to an enzyme or a polypeptide or PEG which increases the serum half-life of the antibody. Such antibody fusion proteins are described separately elsewhere herein.

For antibodies, the sites of greatest interest for substitution variations is the hypervariable regions (or particular CDRs), but framework (FR) alterations also are within the scope of antibody variants and may be associated with advantageous properties and insertions and deletions in the FR regions can be required to obtain a proper or optimal alignment of CDR sequences, for example where hybrid antibody sequences are used. A substitution or other modification (insertion, deletion, or combination of any thereof) in a framework region or constant domain also can be associated with an increase in the half-life of the variant antibody with respect to the parent antibody. A variation in a framework region or constant domain may also be made to alter the immunogenicity of the variant antibody with respect to the parent antibody, to provide a site for covalent or non-covalent binding to another molecule, or to alter such properties as complement fixation. Variations in an antibody variant may be made in each of the framework regions, the constant domain, and/or the variable regions (or any one or more CDRs thereof) in a single variant antibody. Alternatively, variations may be made in only one of the framework regions, the variable regions (or single CDR thereof), or the constant domain in an antibody. Alanine scanning mutagenesis techniques, such as described by Cunningham and Wells (1989), Science 244:1081-1085, can be used to identify suitable residues for substitution or deletion in generating antibodies comprising variant VL, VH, or particular CDR sequences, although other suitable mutagenesis techniques also can be applied. For example, multiple amino acid substitutions also can be made and tested using known methods of mutagenesis and screening, such as those disclosed by Reidhaar-Olson and Sauer, Science 241:53-57 (1988) or Bowie and Sauer Proc. Natl. Acad. Sci. USA 86:2152-2156 (1989). Additional techniques that can be used to generate variant antibodies include the directed evolution and other variant generation techniques described in, e.g., US Patent Application 20040009498; Marks et al., Methods Mol. Biol. 2004; 248:327-43 (2004); Azriel-Rosenfeld et al., J Mol. Biol. 2004 Jan. 2; 335(1):177-92; Park et al., Biochem Biophys Res Commun. 2000 Aug. 28; 275(2):553-7; Kang et al., Proc Natl Acad Sci USA. 1991 Dec. 15; 88(24):11120-3; Zahnd et al., J Biol. Chem. 2004 Apr. 30; 279(18):18870-7; Xu et al., Chem. Biol. 2002 August; 9(8):933-42; Border et al., Proc Natl Acad Sci USA. 2000 Sep. 26; 97(20):10701-5; Crameri et al., Nat. Med. 1996 January; 2(1):100-2; and as more generally described in, e.g., International Patent Application WO 03/048185.

To further improve the quality and/or diversity of antibody sequences, the VL and VH segments of VL/VH pair(s) can be randomly mutated, typically at least within the CDR3 region of VH and/or VL, in a process analogous to the in vivo somatic mutation process responsible for affinity maturation of antibodies during a natural immune response. Such in vitro affinity maturation can be accomplished by, e.g., amplifying VH and VL regions using PCR primers complimentary to VH CDR3 or VL CDR3 encoding sequences, respectively, which primers typically are "spiked" with a random mixture of the four nucleotide bases at certain positions, such that the resultant PCR products encode VH and VL segments into which random mutations have been introduced thereby resulting (at least in some cases) in the introduction of sequence variations in the VH and/or VL CDR3 regions. Such randomly mutated VH and VL segments can thereafter be re-screened by phage display or other suitable technique for binding to targets (such as one or more KIRs) and advantageous variants analyzed and used to prepare novel Anti-KIR antibodies.

In the design, construction, and/or evaluation of CDR variants attention can be paid to the fact that CDR regions can be modified to enable improved epitope binding. Antibody CDRs typically operate by building a "pocket," or other paratope structure, into which the epitope fits. If the epitope does not fit tightly, the antibody may not offer the best affinity. However, as with epitopes, there often are a few key residues in a paratope structure that account for most of this binding. Thus, CDR sequences can vary in length and composition significantly between antibodies specific for the same target protein. The skilled artisan will recognize that certain residues, such as tyrosine residues (e.g., in the context of CDR-H3 sequences), that are often significant contributors to such epitope binding, are typically desirably retained in a CDR variant.

As already mentioned, a convenient way for generating substitution variants is affinity maturation using phage using methods known in the art. In order to identify candidate hypervariable region sites for modification, alanine scanning mutagenesis also can be performed to identify hypervariable region residues contributing significantly to antigen binding. Alternatively or additionally, it may be beneficial to analyze a crystal structure of the antigen-antibody complex to identify contact points between the antibody and antigen. Such contact residues and neighboring residues are likely suitable candidates for substitution.

Useful methods for rational design of CDR sequence variants are described in, e.g., International Patent Applications WO 91/09967 and WO 93/16184. Additional considerations in the production/selection of peptide variants (e.g., conservation of amino acid residue functional characteristics, conservation of amino acid residues based on hydropathic characteristics, and/or conservation of amino acid residues on the basis of weight/size, are described elsewhere herein). Typically, amino acid sequence variations, such as conservative substitution variations, desirably do not substantially change the structural characteristics of the parent sequence (e.g., a replacement amino acid should not tend to disrupt secondary structure that characterizes the function of the parent sequence). Examples of art-recognized polypeptide secondary and tertiary structures are described in, e.g., Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991). Additional principles relevant to the design and construction of peptide variants is discussed in, e.g., Collinet et al., J Biol Chem 2000 Jun. 9; 275(23):17428-33.

The phrase "potential amino acid interactions" can be used to refer to contacts or energetically favorable interactions between one or more amino acid residues present in an antigen and one or more amino acid residues which do not exist in a parent antibody sequence but can be introduced into a variant sequence so as to increase the amino acid contacts between the antigen and an antibody sequence variant comprising such introduced residues. Preferably the amino acid interactions of interest are selected from hydrogen bonding interactions, van der Waals interactions, and/or ionic interactions.

In one particular exemplary aspect, the invention provides an anti-KIR antibody (e.g., a cross-reactive anti-KIR antibody), wherein less than about 10, such as less than about 5, such as 3 or less amino acid variations are present in either the VH or VL regions of the variant antibody sequence with respect to the nearest related wild-type anti-KIR antibody sequence in the context of an anti-KIR antibody (e.g., a sequence from antibody DF200). In another exemplary aspect, the invention provides an anti-KIR antibody comprising a sequence variant wherein less than about 15, such as less than about 10, such as less than about 5 amino acid variations exist in the constant domains of the variant antibody with respect to the most related sequence in a related wild-type anti-KIR, e.g. antibody DF200).

As described elsewhere herein, anti-KIR antibodies can be presented as single chain proteins or as multimers (e.g., dimers, trimers, tetramers (as in the case of wild-type antibodies), or higher-order multimers). Anti-KIR antibodies and antibody fragments will typically be at least in heterotrimeric form if not in higher multimeric forms such as those associated with IgM antibodies. anti-KIR antibodies derived from monomeric proteins can be modified by the inclusion of multimerization-promoting sequences known in the art (examples of which are described elsewhere herein).

Typically, variant sequences desirably retain similar structure as similar parent sequences. Protein structure can be assessed by any number of suitable techniques, such as nuclear magnetic resonance (NMR) spectroscopic structure determination techniques, which are well-known in the art (See, e.g., Wuthrich, NMR of Proteins and Nucleic Acids, Wiley, New York, 1986; Wuthrich, K. Science 243:45-50 (1989); Clore et al., Crit. Rev. Bioch. Molec. Biol. 24:479-564 (1989); Cooke et al. Bioassays 8:52-56 (1988)), typically in combination with computer modeling methods (e.g., by use of programs such as MACROMODEL. INSIGHT, and DISCOVER), to obtain spatial and orientation requirements for structural analogs. Using information obtained by these and other suitable known techniques, structural analogs can be designed and produced through rationally-based amino acid substitutions, insertions, and/or deletions. Computer-based protein structure modeling methods, which may also be useful in this respect, are described elsewhere herein.

As already indicated, it typically is desirable that variant sequences retain at least a substantial proportion of the functionality of the parent sequences from which they are derived, such as with respect to antigen affinity and/or specificity (exceptions may occur where, for example, the particular function, such as constant domain-mediated functions, are sought to be reduced or eliminated). Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or other NKCAMR-binding protein. See, e.g., Zoller M J et al. Nucl. Acids Res. 10:6487-500 (1982) for discussion of related principles.

2. Variants of Anti-KIR Antibody Sequences

For purpose of better illustrating the use of variant sequences in Anti-KIR Antibodies, a number of specific strategies and formulas for generating antibody sequence variants to be incorporated into Anti-KIR Antibodies and used in the production thereof are provided here.

In one aspect, the invention provides an anti-KIR antibody that comprises a CDR L1 sequence variant that consists essentially of a sequence according to the formula $Xaa_1$ Ala Ser $Xaa_4$ $Xaa_5$ Val $Xaa_7$ Ser $Xaa_9$ Tyr Leu $Xaa_{12}$ (SEQ ID NO:30), wherein each "Xaa" represents any suitable amino acid residue (Formula I). In one aspect, the invention provides an anti-KIR antibody comprising a CDR L1 variant sequence according to Formula I wherein the sequence is further characterized by one or more of the following: $Xaa_1$ is Lys or Thr; $Xaa_4$ is Glu or Ser; $Xaa_5$ is Asn or Ser; $Xaa_7$ is Val or Ser; $Xaa_9$ is Ser or is absent; and $Xaa_{12}$ is Ser or Tyr (Formula Ia).

In another aspect, the invention provides an anti-KIR antibody that comprises a CDR L1 sequence variant that consists essentially of a sequence according to the formula $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ (SEQ ID NO:31), wherein (a) $Xaa_1$ is Lys or Thr; $Xaa_4$ is Glu or Ser; $Xaa_5$ is Asn or Ser; $Xaa_7$ is Val or Ser; and $Xaa_{12}$ is Ser or Tyr; (b) $Xaa_8$ and $Xaa_{11}$ are any suitable amino acid residue, $Xaa_8$ is Thr or Ser, $Xaa_{11}$ is Val or Leu, or $Xaa_8$ is Thr or Ser and $Xaa_{11}$ is Val or Leu; (c) $Xaa_9$ is Ser, absent, or any suitable amino acid residue other than Ser (e.g., Gly); and (d) $Xaa_2$ $Xaa_3$ $Xaa_6$ $Xaa_{10}$ and $Xaa_{11}$ are each defined by the corresponding positions in Formula I (e.g., $Xaa_2$ is Ala), optionally except for one or more of the following: $Xaa_2$ is any suitable residue other than Ala; $Xaa_3$ is any suitable residue other than Ser; $Xaa_6$ is any suitable residue other than Val; $Xaa_{10}$ is any suitable residue other than Tyr; and $Xaa_{11}$ is any suitable residue other than Leu (Formula II). In another aspect, the invention provides a similar CDR L1 variant that differs from SEQ ID NO:1 and/or SEQ ID NO:2 only by one or more sequence variations defined by either part (a) or part (b) of Formula (IIa).

In another aspect, the invention provides an anti-KIR antibody comprising a CDR L2 variant that consists essentially of a sequence according to the formula $Xaa_1$ $Xaa_2$ Ser Asn $Xaa_5$ $Xaa_6$ Ser (SEQ ID NO:32), wherein Xaa is any suitable amino acid residue (Formula III). In a more particular aspect, the invention provides an anti-KIR antibody that comprises a CDR L2 variant that consists essentially of a Formula III sequence wherein the sequence is characterized by one or more of the following: $Xaa_1$ is Gly or Ser; $Xaa_2$ is Ala or Thr; $Xaa_5$ is Arg or Leu; and $Xaa_6$ is Tyr or Ala (Formula IIIa).

In a further facet, the invention provides an anti-KIR antibody that comprises a CDR L2 variant that consists essentially of a sequence according to the formula $Xaa_1$ $Xaa_2$ $Xaa_3$ $Xaa_4$ $Xaa_5$ $Xaa_6$ $Xaa_7$ (SEQ ID NO:33), wherein (a) $Xaa_1$ is Gly or Ser, $Xaa_2$ is Ala or Thr, $Xaa_5$ is Arg or Leu, and $Xaa_6$ is Tyr or Ala; (b) $Xaa_7$ is any suitable residue (such as an Ala residue or another flexible residue). Thr, or Ser; and (c) $Xaa_3$ is a Ser and $Xaa_4$ is any suitable residue other than Asn, $Xaa_3$ is any suitable residue other than Ser and $Xaa_4$ is Asn, or $Xaa_3$ is any suitable residue other than Ser and $Xaa_4$ is any suitable residue other than Asn (Formula IV). In another aspect, the invention provides a similar CDR L2 variant sequence wherein the sequence differs from SEQ ID NO:5 and/or SEQ ID NO:6 only by (i) one or more changes defined by part (a) or (ii) one or both changes in part (c) of Formula IV.

In yet another aspect, the invention provides an anti-KIR antibody that comprises a CDR L3 variant sequence that consists essentially of a sequence according to the formula $Xaa_1$ Gln $Xaa_3$ His $Xaa_5$ $Xaa_6$ Pro $Xaa_8$ Thr (SEQ ID NO:34), wherein Xaa is any suitable amino acid residue (Formula V). In a more particular aspect, the invention provides an anti-KIR antibody that comprises a CDR L3 variant consisting essentially of a sequence according to Formula V wherein the sequence is further characterized by one or more of the following $Xaa_1$ is Gly or His, $Xaa_3$ is Gly or Tyr, $Xaa_5$ is Ser or Arg, $Xaa_6$ is Tyr or Ser, and $Xaa_8$ is Tyr or Pro (Formula Va).

In a further facet, the invention provides an anti-KIR antibody that comprises a CDR L3 variant sequence that consists essentially of a sequence according to the formula $Xaa_1$ $Xaa_2$ $Xaa_3$ $Xaa_4$ $Xaa_5$ $Xaa_6$ $Xaa_7$ $Xaa_8$ $Xaa_9$ (SEQ ID NO:35), wherein (a) $Xaa_1$ is Gly or His, $Xaa_3$ is Gly or Tyr, $Xaa_5$ is Ser or Arg, $Xaa_6$ is Tyr or Ser, and $Xaa_8$ is Tyr or Pro; (b) $Xaa_4$ is Tyr, His, or another suitable residue (e.g., another cycloalkenyl-associated residue); and (c) $Xaa_2$, $Xaa_7$, and $Xaa_9$ are defined according to corresponding positions in Formula V except in for one or more of the following: $Xaa_2$ is any suitable residue other than Gln. $Xaa_7$ is any suitable residue other than Pro, and $Xaa_9$ is any suitable residue other than Thr (Formula VI). In another aspect, the invention provides an anti-KIR antibody comprising a CDR L3 variant that consists essentially of a Formula V sequence but wherein either all of $Xaa_1$, $Xaa_3$, $Xaa_6$, and $Xaa_8$ correspond to the identical positions in SEQ ID NO:22 or SEQ ID NO:8 or $Xaa_2$, $Xaa_7$, and $Xaa_9$ correspond to the identical positions in Formula V.

In another facet, the invention provides an anti-KIR antibody that comprises a CDR H1 variant that consists essentially of a sequence according to the formula Gly Phe Ser $Xaa_4$ Thr $Xaa_6$ Tyr Gly Val His (SEQ ID NO:36), wherein $Xaa_4$ is any suitable residue other than Glu (e.g., Leu), $Xaa_6$ is any suitable residue other than Phe (e.g., Ser), or $Xaa_4$ and $Xaa_6$ represent any suitable residue other than Glu and Phe, respectively (Formula VII).

In yet another aspect, the invention provides an anti-KIR antibody that comprises a CDR H1 variant that consists essentially of a sequence according to the formula $Xaa_1$ $Xaa_2$ $Xaa_3$ Glu $Xaa_5$ Phe $Xaa_7$ $Xaa_8$ $Xaa_9$ $Xaa_{10}$ (SEQ ID NO:37), wherein one or more of $Xaa_1$, $Xaa_2$, $Xaa_3$, $Xaa_5$, $Xaa_7$, $Xaa_8$, $Xaa_9$, and $Xaa_{10}$ differ from the corresponding position in SEQ ID NO:23 (Formula VIII). In one aspect, the invention provides an anti-KIR antibody that comprises a CDR H1 variant that consists essentially of a Formula VIII sequence wherein the Formula VIII sequence exhibits at least 70% (such as at least 80% or at least 90%) identity to SEQ ID NO:23.

In a further facet, the invention provides an anti-KIR antibody that comprises a CDR H2 variant that consists essentially of a sequence according to the formula Val Ile Trp Ser Gly Gly $Xaa_7$ Thr Asp Tyr Asn Ala Ala Phe Ile Ser (SEQ ID NO:38), wherein $Xaa_7$ is any suitable residue other than Asn (Formula IX).

In an additional aspect, the invention provides an anti-KIR antibody that comprises a CDR H2 variant that consists essentially of a sequence according to the formula $Xaa_1$ $Xaa_2$ $Xaa_3$ $Xaa_4$ $Xaa_5$ $Xaa_6$ Asn $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ (SEQ ID NO:39), wherein the sequence exhibits at least about 60%, typically at least about 70%, such as about 80% or more (e.g., about 90% or more) identity to SEQ ID NO:11, but differs by one or more substitutions in any one of positions $Xaa_1$-$Xaa_6$ and $Xaa_8$-$Xaa_{16}$ (Formula X).

Another aspect of the invention is an anti-KIR antibody that comprises a CDR H3 variant that consists essentially of a sequence according to the formula Asn Pro Arg Pro Gly Asn Tyr Arg Tyr Gly $Xaa_{11}$ $Xaa_{12}$ Tyr (SEQ ID NO:40), wherein $Xaa_{11}$ is any suitable residue other than Met and $Xaa_{12}$ is Asp. $Xaa_{11}$ is Met and $Xaa_{12}$ is any suitable residue other than Asp, or $Xaa_{11}$ and $Xaa_{12}$ represent any suitable residues other than Met and Asp, respectively (Formula XI).

Another feature of the invention is provided in an anti-KIR antibody that comprises a CDR H3 variant that consists essentially of a sequence according to the formula $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ (SEQ ID NO:41), wherein the sequence exhibits at least about 70% identity to SEQ ID NO:12 (Formula XII), typically by 1-4 substitutions in $Xaa_1$-$Xaa_{13}$. In one aspect, the invention provides such an anti-KIR antibody wherein $Xaa_{11}$ is Met and/or $Xaa_{12}$ is Asp.

The invention also provides an anti-KIR antibody that comprises a CDR-H1 variant that consists essentially of a sequence according to the formula Gly $Xaa_2$ $Xaa_3$ Phe Thr $Xaa_6$ Tyr $Xaa_8$ $Xaa_9$ His (SEQ ID NO:42), wherein $Xaa_2$ is a cycloalkenyl residue, typically an aromatic residue, and more typically Phe or Tyr; $Xaa_3$ is selected from Ser, Thr, Ala, Asn, and Gln and more typically Ser, Thr, and Ala or even more typically Ser or Thr; $Xaa_6$ is Pro or Ser; $Xaa_8$ is Gly or Trp; and $Xaa_9$ is selected from Met, Ile, Leu, Val and Phe or more typically from Met, Ile, Leu, and Val (Formula XIII).

In a further aspect, the invention provides an anti-KIR antibody that comprises a CDR-H1 variant that consists essentially of a sequence according to the formula $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ (SEQ ID NO:43), wherein $Xaa_2$, $Xaa_3$, $Xaa_6$, $Xaa_8$, and $Xaa_9$ are as defined in Formula XIII and $Xaa_1$, $Xaa_4$, $Xaa_5$, $Xaa_7$, and $Xaa_{10}$ represent the same residues as found in the corresponding positions in Formula XIII except for one or more of the following: $Xaa_1$ is any suitable residue other than Gly; $Xaa_4$ is any suitable residue other than Phe; $Xaa_5$ is any suitable residue other than Thr; $Xaa_7$ is any suitable residue other than Tyr; and $Xaa_{10}$ is any suitable residue other than His (Formula XIV).

In a more general sense, the invention provides Anti-KIR antibodies that comprise one or more variant CDRs that are highly similar to SEQ ID NOS:1-6, 22, 8, 23, 11 and 12 (e.g., the invention provides Anti-KIR antibodies comprising at least one CDR variant that exhibits at least about 50%, at least about 60%, at least about 70%, at least about 80%, at least about 90%, at least about 95% or more identity to at least one of SEQ ID NOS:1-6, 22, 8, 23, 11 and 12).

In a further aspect, the invention provides Anti-KIR antibodies that comprise a combination of such CDR variants (e.g., an anti-KIR antibody that comprises a CDR L1 variant according to Formulas I-II, a CDR L2 variant according to Formulas III-IV, a CDR L3 variant according to Formulas V-VI, a CDR H1 variant according to Formulas VII-VIII, a CDR H2 variant according to Formulas IX-X, and/or a CDR H3 variant according to Formulas XI-XII). In an additional facet, the invention provides an anti-KIR antibody that comprises a combination of such CDR variants and one or more CDR sequences selected from SEQ ID NOS:1-6, 22, 8, 23, 11 and 12.

The invention also provides a method of preparing KIR-binding variant antibody sequences (for incorporation in an artificial anti-KIR antibody) comprising preparing an antibody or antibody sequence-comprising protein that comprises a combination of variant CDRs as defined by the foregoing formulas (e.g., Formulas I-XII), assessing the affinity of the variant antibody sequence for at least one KIR, and selecting a sequence that binds to at least one KIR with an at least predetermined affinity level (a level that typically is comparable with those described elsewhere herein).

Monoclonal antibodies in particular may be made using the hybridoma method first described by Kohler et al., Nature, 256:495 (1975), or by other well-known, subsequently-developed methods (see, e.g., Coding, Monoclonal Antibodies: Principles and Practice, pp. 59-103 (Academic Press, 1986)). Hybridomas and other fusion cells may be formed by chemical fusion, electrical fusion, or any other suitable technique, with any suitable type of myelomas, heteromyelomas, phoblastoid cells, plasmacytomas or similar immortalized cell and any suitable type of antibody-expressing cell(s).

Transformed immortalized B cells also can be used to efficiently produce antibodies. Transformed B cells can be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pp 19-33.). Thus, stable and continuous and/or immortalized anti-KIR antibody-expressing cells and cell lines are another feature of the invention. A step of a method for producing anti-KIR antibodies can include, for example, a step of producing immortalized B cells producing an anti-AMR antibody and/or anti-STM antibody which are fused to appropriate partners to produce anti-KIR antibody (s) or which are sequenced and such sequences used to produce a recombinant anti-KIR antibody.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding antibody genes are introduced into mammalian host cells, antibodies can be produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Antibodies may also be recovered from host cell lysates when directly expressed without a secretory signal.

The purification of antibodies from cell cultures, cell lysates, and transgenic animals or biological materials obtained therefrom (e.g., from the ascites fluid of a transgenic animal producing antibodies) can be achieved by application of any number of suitable techniques known in the art including, e.g., immunoaffinity column purification; sulfate precipitation; chromatofocusing; preparative SDS-PAGE, and the like.

Anti-KIR antibodies also can be produced in bacterial cells and eukaryotic unicellular microorganisms, such as yeast. Bacterial cell produced antibodies lack normal glycosylation and accordingly may be deficient in terms of ADCC functions and other aspects of the immune response that may otherwise be associated with essentially identical antibodies produced in mammalian cells and/or animals. Yeast cell-produced antibodies, for example, normally exhibit different types of glycosylation patterns than antibodies produced in mammalian cells. However, methods for producing antibodies with effective glycosylation in yeast have recently been developed and made commercially available by companies such as Glycofi, Inc. (Lebanon, N.H., USA) (see, e.g., Hamilton et al., Science. 2003 Aug. 29; 301(5637):1244-6; Choi et al., Proc Natl Acad Sci USA. 2003 Apr. 29; 100(9):5022-7; and Gerngross et al., "Production of Complex Human Glycoproteins in Yeast" presented at "Anti-body Engineering and Optimization," available through Cambridge Health Institute Proceedings (presented on Apr. 28, 2004)). Glycosylation of proteins also can be modified using techniques such as are described in U.S. Patent Applications 20030124645, 20030180835, 20040063911, and U.S. Pat. No. 6,379,933. Anti-KIR antibodies produced in yeast and similar cells combination of these methods with other method aspects of this invention are an additional facet of the invention. For example, an anti-KR antibody production method of the invention can include the step of producing an anti-KIR antibody in a yeast cell according to such methods, e.g., using nucleic acids encoding anti-KIR antibody portions described herein, so as to produce a anti-KIR antibody exhibiting human glycosylation patterns in human anti-AMR antibody and/or anti-STM antibody sequences produced therein.

Anti-KIR antibodies can be purified from using any one or combination of known biochemical techniques.

For example, anti-KIR antibody-expressing polydoma cell culture broth can centrifuged; the resulting supernatant collected; and the supernatant subjected to salting-out (normally using ammonium sulfate or sodium sulfate). The obtained protein precipitate can be dissolved in an appropriate solution and dialyzed, and subjected to column chromatography (using, e.g., an ion exchange column, gel filtration column, Protein A column, or hydroxyapatite column) to separate and purify the desired anti-KIR antibody. Single step separation and purification can also be conducted by the process using a column in which a target NKCAMR and a target STM (or related molecules) have been immobilized.

Other suitable methods for purifying anti-KIR antibodies include isoelectric focusing, affinity chromatography, including double affinity chromatography (e.g., using sequential mouse anti-idiotype anti-isotype monoclonal antibodies to purify anti-KIR antibodies), hydroxylapatite chromatography, ion-exchange chromatography (e.g., cation exchange chromatography). ELISA, immobilized metal affinity chromatography (IMAC), size exclusion chromatography, polyacrylamide gel electrophoresis (PAGE), western blotting, surface plasmon resonance (SPR), mass spectroscopymimetic affinity methods, gradient thiophilic chromatography, dialysis, filtering methods, and high performance liquid chromatography (HPLC) methods.

Screening and selection of anti-KIR antibodies can be accomplished by any suitable technique or combination of techniques. For example, a variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane, supra. The binding affinity of a monoclonal antibody can, for example, be determined by the Scatchard analysis of Munson et al., Anal. Biochem., 107:220 (1980).

Anti-KIR antibodies typically are screened for the ability to modulate NK cell activity, such as by inhibiting KIR-mediated signals, promoting activation of NK cells through NCR or other KAR-mediated signals, or the like. A number of NK cell assays have been developed that can be useful in such contexts including, for example, flow cytometric screening methods. See, e.g., McGinnes et al., J Immunol Methods 80 1984 70-85. Methods relevant to culturing NK cells, assessing NK cells, and the like are known in the art. See, e.g., Campbell and Colonna, Natural Killer Cell Protocols (Methods in Molecular Biology Series vol. 121) (2000).

In the context of Anti-KIR Antibodies, NK cell neutralizing activity can be demonstrated by the capacity of an anti-KIR Antibody to reconstitute lysis of target cells by KIR-positive NK cells. For example, an assay involving an anti-KIR Antibody comprising one or more KIR-binding portions derived from antibody DF200 can involve measuring the ability of KIR2DL-positive NK clones to lyse HLA-C positive targets in the presence of the Anti-KIR Antibodies as compared to in the absence of the Anti-KIR Antibodies. In such contexts, neutralizing activity of an anti-KIR Antibody also or alternatively can be defined by, e.g., the ability of the Anti-KIR Antibody to inhibit the binding of HLA-C molecules to KIR2DL1 and KIR2DL3 (or the closely related KIR2DL2) receptors. More particularly in such contexts, neutralizing ability can be measured in terms of the ability of the Anti-KIR Antibody to inhibit the binding of a HLA-C molecule selected from Owl, Cw3, Cw7, and Cw8 (or of a HLA-C molecule having an Asn residue at position 80) to KIR2DL2/3 and/or the binding of a HLA-C molecule selected from Cw2, Cw4, Cw5 and Cw6 (or of a HLA-C molecule having a Lys residue at position 80) to KIR2DL1.

NK cell activity changes brought about by anti-KIR antibodies can be determined by a method that comprises taking a biopsy, preparing tissue sections obtained thereby for immunohistochemistry analysis, staining the tissue for NK cells (e.g., using mAbs specific for CD56, NKp30, NKp46, or other NK-specific cell markers), and quantifying the number of NK cells and co-staining for a marker (such as NKp44, CD25, CD69, CD86, or other(s)) that is/are specifically up-regulated on activated NK cells, so as to determine the proportion of activated NK cells in the population. Such measurements also could be made by FACS analysis if cell suspensions are prepared from the tissue samples.

Anti-KIR antibody-associated NK cell modulation (e.g., KIR inhibition) can also be assessed by various cell based cytotoxicity assays.

In another variant, the NK cell activity modulation associated with an anti-KIR anti-body can be assessed in a cytokine-release assay, wherein NK cells are incubated with a test anti-KIR antibody and a target cell line to stimulate NK cell cytokine production (for example IFN-γ and/or GM-CSF production). For example, in the context of Anti-KIR Antibodies, a cell line expressing one HLA-C allele recognized by a KIR molecule of the test NK cell population can be used in such a cytokine release assay. In an even more particularly exemplary protocol, IFN-γ production from PBMC can be assessed by cell surface and intracytoplasmic staining and analysis by flow cytometry after about 4 days in culture. Briefly, Brefeldin A (Sigma Aldrich) can be added at a final concentration of about 5 μg/ml for the least about 4 hours of culture. The cells can then incubated with anti-CD3 and anti-CD56 mAb prior to permeabilization (INTRAPREP; Beckman Coulter) and staining with PE-anti-IFN-γ or PE-IgG1 (Pharmingen). GM-CSF and IFN-γ production from polyclonal activated NK cells can be measured in supernatants using ELISA (GM-CSF: DuoSet Elisa, R&D Systems, Minneapolis, Minn.; IFN-γ: OptE1A set, Pharmingen).

Anti-KIR antibodies can be selected based on any suitable criteria. For example, in one aspect, Anti-KIR antibodies are selected based on the ability to cause at least about 10% specific lysis mediated by NK cells displaying at least one KIR recognized by the Anti-KIR antibody, and desirably at least about 40% specific lysis, at least about 50% specific lysis, or even at least about 70% specific lysis (e.g., about 60-100% specific lysis), as measured in a standard chromium release assay, towards a target cell expressing cognate HLA class I molecule, compared with the lysis or cytotoxicity obtained at the same effector/target ratio with NK cells that are not blocked by their KIR. As another illustrative example, Anti-KIR antibodies derived from DF200 or another anti-KIR antibody can be selected based on the ability to increase the cytotoxicity level against target cells at least about 20%, at least about 30%, at least about 35%, or more in the context of a chromium release assay performed in the presence of NK cells expression one or more KIRs for which the Anti-KIR antibodies are specific.

In another aspect, target cell apoptosis can be used as an indicator of Anti-KIR antibody NK cell activity modulation. Apoptosis can be determined through well known DNA analysis techniques. For example, a characteristic DNA laddering pattern is recognized as a hallmark of apoptotic cell death. Techniques for visualizing such DNA fragmentation are known. Such techniques typically involve resolving fragmented DNA by agarose gel electrophoresis, and the use of dyes that allow visualization of DNA. Another way to confirm cell death is by staining the target cells with trypan blue. An alternative is crystal violet staining, performed as described by Flick and Gifford (J. Immunol. Methods 68:167-175, 1984).

Redirected killing is an experimental system for determining the capacity of a NK-cell receptor to induce cytotoxicity. NK cells coated with antibody specific for a candidate receptor are assessed for their ability to kill target cells that express an Fc receptor to which the antibody binds.

Other biological activities associated with various Anti-KIR antibodies also can be used to evaluate Anti-KIR antibodies. For example, Anti-KIR antibodies can be evaluated for their ability to induce, promote, and/or enhance antibody-dependent cellular cytotoxicity (ADCC). $IgG_{2a}$, $IgG_3$, and some $IgG_1$ subclass antibodies typically mediate ADCC, such that isotype considerations (and possibly modifications) are taken into account if ADCC functioning is desired. The ability to induce ADCC can be assessed using a chromium release assay. Briefly, a cell line expressing the antigen being targeted for lysis by effector cells are labeled with about 100 μCi of $^{51}Cr$ for about 1 hour prior to combining effector cells and Anti-KIR antibodies in a U-bottom microtiter plate. After incubation for about 5 hours at about 37° C., supernatants can be collected and analyzed for radioactivity. Cytotoxicity can be calculated by the formula: % lysis=[((experimental CPM)−(target leak CPM))/((detergent lysis CPM)−(target leak CPM))]×100%. Specific lysis can be calculated using the formula: Specific lysis=(% lysis with antibody)−(% lysis without antibody).

Anti-KIR antibodies also or alternatively can be selected based on their ability to provide or not provide complement fixation and/or induce, promote, and/or enhance complement dependent cytotoxicity (CDC). There are a number of isotypes of antibodies that are capable of complement fixation and CDC, including, without limitation, the following: murine IgM, murine IgG2a, murine IgG2b, murine IgG3, human IgM, human IgG1, and human IgG3. Those isotypes that do not include, without limitation, human IgG2 and human IgG4. Isotype determination and other methods for modifying the complement fixation and CDC functional characteristics of antibodies are known in the art.

Additional ADCC and CDC assays and related principles are described in, e.g., U.S. Pat. No. 5,500,362.

Anti-KIR antibodies also can be selected on the basis of their ability to induce, promote, and/or enhance complement activation. Antibodies of the $IgG_3$, $IgG_{2a}$ and IgM classes typically bind and activate serum complement. Appropriate isotype considerations and/or adjustments can be made if such functions are desired. Complement binding assays are known in the art and generally involve incubation of target cells with candidate Anti-KIR antibodies, washing, contacting with complement, incubating, and adding tryptan blue or other appropriate die to allow measurement of cell number and assessment of cell plasma integrity.

Anti-KIR antibodies also can be assessed on the basis of their ability to induce, promote, and/or enhance phagocytosis. Phagocytosis assays are known. As an example, target cells can be labeled with lipophilic red fluorescent dye PKH 26. Buffy coat cells purified from heparinized, whole blood containing effector cells can be incubated with the labeled targets at about 37° C. for about 6 hours in the absence or in the presence of Anti-KIR antibodies. Effector cells can thereafter be stained with FITC (fluorescein isothiocyanate) labeled antibody, which binds to the effector cell at 0° C. Cells typically are thereafter washed and analyzed using two color fluorescence by FACScan or other scanning method. Percent phagocytosis is expressed as the percent of effector cells (NK cells, monocytes, neutrophils, or macrophages) associated with a PKH 26 stain.

Anti-KIR antibodies can be provided in a homogenous composition or in combination with other active and/or inert ingredients.

Anti-KIR antibodies typically are used in and provided in an at least substantially pure form. A substantially pure molecule is a molecule that is the predominant species in the composition wherein it is found with respect to the class of molecules to which it belongs (e.g., a substantially pure antibody is the predominant protein species in the composition wherein it is found. A substantially pure species makes up at least about 50% of the type of molecule in the composition and typically will make up at least about 70%, at least about 80%, at least about 85%, at least about 90%, at least about 95%, or greater percentage of the species in the composition by weight. Commonly, a composition comprising a Anti-KIR antibody will exhibit at least about 98%, 98%, or 99% homogeneity for the Anti-KIR antibody in the context of all present peptide species in the composition or at least with respect to substantially active peptide species in the context of proposed use. For example, a peptide stabilizer/buffer such as an albumin may be intentionally included in a final pharmaceutical formulation, without impeding the activity of the Anti-KIR antibodies, and, accordingly, may be excluded from such purity calculations. The presence of impurities that do not interfere with the fundamental activity also may be acceptable in the context of a substantially pure composition. Purity can be measured by methods appropriate for the given compound (e.g., chromatographic methods; agarose and/or polyacrylamide gel electrophoresis; HPLC analysis; etc.).

An isolated molecule refers to a molecule that is not associated with significant levels (e.g., more than about 1%, more than about 2%, more than about 3%, or more than about 5%) of any extraneous and undesirable biological molecules, such as non-Anti-KIR antibody biological molecules contained within a cell, cell culture, chemical media, or animal in which the Anti-KIR antibody was produced. An isolated molecule also refers to any molecule that has passed through such a stage of purity due to human intervention (whether automatic, manual, or both) for a significant amount of time (e.g., at least about 10 minutes, at least about 20 minutes, at least about one hour, or longer). In many of the various compositions provided by the invention, such as in a composition comprising one or more pharmaceutically acceptable carriers, a Anti-KIR antibody can be present in relatively small amounts in terms of numbers of total molecular species in the composition (e.g., in the case of a composition comprising a large amount of a pharmaceutically acceptable carrier, stabilizer, and/or preservative). In some cases additional peptides, such as BSA, can be included in such a composition with a previously purified Anti-KIR antibody. However, provided that such additional constituents of the composition are acceptable for the intended application of the Anti-KIR antibody, such a composition can still be described as comprising an isolated Anti-KIR antibody. In other words, the term "isolated" is not meant to exclude artificial or synthetic mixtures with other compounds or materials, such as may form part of a pharmaceutically acceptable preparation.

In one aspect, the invention provides Anti-KIR antibodies that are substantially free of other NKCAMR-binding molecules and/or STM-binding molecules.

In another aspect, the invention provides a composition comprising a number of Anti-KIR antibodies with different specificities and characteristics (e.g., the invention provides in one aspect a "cocktail" of Anti-KIR antibodies having different specificity and/or selectivity characteristics).

Anti-KIR antibody compositions for pharmaceutical use typically contain at least a physiologically effective amount and commonly desirably contain a therapeutically effective amount of an Anti-KIR antibody, combination of Anti-KIR antibodies, or Anti-KIR antibodies and additional active/therapeutic agents.

A "therapeutically effective amount" refers to an amount of a biologically active compound or composition that, when delivered in appropriate dosages and for appropriate periods of time to a host that typically is responsive for the compound or composition, is sufficient to achieve a desired therapeutic result in a host and/or typically able to achieve such a therapeutic result in substantially similar hosts (e.g., patients having similar characteristics as a patient to be treated). A therapeutically effective amount of an Anti-KIR antibody may vary according to factors such as the disease state, age, sex, and weight of the individual, and the ability of the Anti-KIR antibody to elicit a desired response in the individual. A therapeutically effective amount is also one in which any toxic or detrimental effects of the antibody or antibody portion are outweighed by the therapeutically beneficial effects. Exemplary therapeutic effects include, e.g., (a) a reduction in the severity of a disease, disorder, or related condition in a particular subject or a population of substantial similar subject; (b) a reduction in one or more symptoms or physiological conditions associated with a disease, disorder, or condition; or (c) a prophylactic effect. A reduction of the severity of a disease can include, for example, (a) a measurable reduction in the spread of a disorder (e.g., the spread of a cancer in a patient); (b) an increase in the chance of a positive outcome in a subject (e.g., an increase of at least about 5%, 10%, 15%, 20%, 25%, or more); (c) an increased chance of survival or lifespan; and/or (d) a measurable reduction in one or more biomarkers associated with the presence of the disease state (e.g., a reduction in the amount and/or size of tumors in the context of cancer treatment; a reduction in viral load in the context of virus infection treatment; etc.). A therapeutically effective amount can be measured in the context of an individual subject or, more commonly, in the context of a population of substantial similar subjects (e.g., a number of human patients with a similar disorder enrolled in a clinical trial involving an Anti-KIR antibody composition or a number of non-human mammals having a similar set of characteristics being used to test an Anti-KIR antibody in the context of preclinical experiments).

A "prophylactically effective amount" refers to an amount of an active compound or composition that is effective, at dosages and for periods of time necessary, in a host typically responsive to such compound or composition, to achieve a desired prophylactic result in a host or typically able to achieve such results in substantially similar hosts. Exemplary prophylactic effects include a reduction in the likelihood of developing a disorder, a reduction in the intensity or spread of a disorder, an increase in the likelihood of survival during an imminent disorder, a delay in the onset of a disease condition, a decrease in the spread of an imminent condition as compared to in similar patients not receiving the prophylactic regimen, etc. Typically, because a prophylactic dose is used in subjects prior to or at an earlier stage of disease, the prophylactically effective amount will be less than the therapeutically effective amount for a particular Anti-KIR antibody. A prophylactic effect also can include, e.g., a prevention of the onset, a delay in the time to onset, a reduction in the consequent severity of the disease as compared to a substantially similar subject not receiving Anti-KIR antibody composition, etc.

A physiologically effective amount is an amount of an active agent that upon administration to a host that is normally responsive to such an agent results in the induction, promotion, and/or enhancement of at least one physiological effect associated with modulation of NK cell activity (e.g., increase in NK cell-associated apoptosis; increase in NK cell-associated IFNγ secretion; etc.).

"Treatment" refers to the delivery of an effective amount of a therapeutically active compound of the invention with the purpose of preventing any symptoms or disease state to develop or with the purpose of easing, ameliorating, or eradicating (curing) such symptoms or disease states already developed. The term "treatment" is thus meant to include prophylactic treatment. However, it will be understood that therapeutic regimens and prophylactic regimens of the invention also can be considered separate and independent aspects of this invention.

A. Pharmaceutically Acceptable Carriers

An Anti-KIR antibody can be combined with one or more carriers (diluents, excipients, and the like) and/or adjuvants appropriate for one or more intended routes of administration to provide compositions that are pharmaceutically acceptable.

Anti-KIR antibodies may be, for example, admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and optionally further tableted or encapsulated for conventional administration. Alternatively, an Anti-KIR antibody or other Anti-KIR antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier or diluent may include time delay material, such as glyceryl monostearate or glyceryl distearate alone or with a wax, or other functionally similar materials.

Pharmaceutically acceptable carriers generally include any and all suitable solvents, dispersion media, coatings, antibacterial and antifungal agents, isotonic and absorption delaying agents, and the like that are physiologically compatible with an Anti-KIR antibody. Examples of pharmaceutically acceptable carriers include water, saline, phosphate buffered saline, dextrose, glycerol, ethanol, and the like, as well as combinations of any thereof. In many cases, it can be desirable to include isotonic agents, for example, sugars, polyalcohols such as mannitol, sorbitol, or sodium chloride in such a composition. Pharmaceutically acceptable substances such as wetting agents or minor amounts of auxiliary substances such as wetting agents or emulsifying agents, preservatives or buffers, which desirably can enhance the shelf life or effectiveness of the Anti-KIR antibody, related composition, or combination. Suitability for carriers and other components of pharmaceutical compositions is determined based on the lack of significant negative impact on the desired biological properties of the Anti-KIR antibody, related composition, or combination (e.g., less than a substantial impact (10% or less relative inhibition, 5% or less relative inhibition, etc.) on NKCAMR and STM binding in the case of an Anti-KIR antibody fragment).

Anti-KIR antibody compositions, related compositions, and combinations according to the invention may be in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (see, e.g., Baek et al., Methods Enzymol. 2003; 362:240-9; Nigavekar et al., Pharm Res. 2004 March; 21(3): 476-83), microparticles, and suppositories. The optimal form for any Anti-KIR antibody-associated composition depends on the intended mode of administration, the nature of the composition or combination, and therapeutic application or other intended use. Formulations also can include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions, carbowax (polyethylene glycols of various molecular weights), semi-solid gels, and semi-solid mixtures containing carbowax. Any of the foregoing mixtures may be appropriate in treatments and therapies in accordance with the present invention, provided that the binding of the Anti-KIR antibody to its γ2 DIII-associated peptide target(s) is not significantly inhibited and/or the biological activity of related molecule(s) significantly inhibited by the formulation and the formulation is physiologically compatible and tolerable with the route of administration. See also, e.g., Powell et al. "Compendium of excipients for parenteral formulations" PDA J Pharm Sci Technol. 52:238-311 (1998) and the citations therein for additional information related to excipients and carriers well known to pharmaceutical chemists.

In a particular aspect, Anti-KIR antibodies are administered in liposomes (immunoliposomes). In another aspect, Anti-KIR antibodies are administered in liposomes and a secondary agent, such as an antisense RNA, RNAi or siRNA for suppressing a gene in an NK cell, or toxins or drugs for the targeted killing of NK cells (additional secondary agents for combination therapies are described elsewhere herein). The production of liposomes is well known in the art. Immunoliposomes also can be targeted to particular cells by standard techniques.

Anti-KIR antibody compositions also include compositions comprising any suitable combination of an Anti-KIR antibody peptide and a suitable salt therefor. Any suitable salt, such as an alkaline earth metal salt in any suitable form (e.g., a buffer salt), can be used in the stabilization of Anti-KIR antibodies (preferably the amount of salt is such that oxidation and/or precipitation of the Anti-KIR antibody is avoided). Suitable salts typically include sodium chloride, sodium succinate, sodium sulfate, potassium chloride, magnesium chloride, magnesium sulfate, and calcium chloride. In one aspect, an aluminum salt is used to stabilize an Anti-KIR antibody in a composition of the invention, which aluminum salt also may serve as an adjuvant when such a composition is administered to a patient. Compositions comprising a base and Anti-KIR antibodies also are provided. In other aspects, the invention provides an Anti-KIR antibody composition that essentially lacks a tonicifying amount of any salt.

Typically, compositions in the form of injectable or infusible solutions, such as compositions similar to those used for passive immunization of humans with other antibodies, are used for delivery of Anti-KIR antibodies of the invention. A typical mode for delivery of Anti-KIR antibody compositions is by parenteral administration (e.g., intravenous, subcutaneous, intraperitoneal, and/or intramuscular administration). In one aspect, an Anti-KIR antibody is administered to a human patient by intravenous infusion or injection. In another aspect, an Anti-KIR antibody is administered by intramuscular or subcutaneous injection. As indicated above, intratumor administration also may be useful in certain therapeutic regimens.

Thus, Anti-KIR antibodies, such as Anti-KIR antibody antibodies, may be formulated in, for example, solid formulations (including, e.g., granules, powders, projectile particles, or suppositories), semisolid forms (gels, creams, etc.), or in liquid forms (e.g., solutions, suspension, or emulsions). Antibodies and other Anti-KIR antibodies may be applied in a variety of solutions. Suitable solutions for use in accordance with the invention typically are sterile, dissolve sufficient amounts of the antibody and other components of the composition (e.g., an immunomodulatory cytokine such as GM-CSF, IL-2, and/or KGF), stable under conditions for manufacture and storage, and not harmful to the subject for the proposed application. A Anti-KIR antibody may be subjected to conventional pharmaceutical operations such as sterilization and/or may contain conventional adjuvants, such as preservatives, stabilizers, wetting agents, emulsifiers, buffers etc. A composition also can be formulated as a solution, microemulsion, dispersion, powder, macroemulsion, liposome, or other ordered structure suitable to high drug concentration. Desirable fluidity properties of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. These and other components of a pharmaceutically acceptable composition of the invention can impart advantageous properties such as improved transfer, delivery, tolerance, and the like.

A composition for pharmaceutical use also can include various diluents, fillers, salts, buffers, detergents (e.g., a nonionic detergent, such as Tween-80), stabilizers (e.g., sugars or protein-free amino acids), preservatives, tissue fixatives, solubilizers, and/or other materials suitable for inclusion in a composition for pharmaceutical use. Examples of suitable components also are described in, e.g., Berge et al., J. Pharm. Sci., 6661), 1-19 (1977); Wang and Hanson, J. Parenteral. Sci. Tech: 42, S4-S6 (1988);U.S. Pat. Nos. 6,165,779 and 6,225,289; and other documents cited herein. Such a pharmaceutical composition also can include preservatives, antioxidants, or other additives known to those of skill in the art. Additional pharmaceutically acceptable carriers are known in the art and described in, e.g., Urquhart et al., Lancet, 16, 367 (1980), Lieberman et al., Pharmaceutical Dosage Forms-Disperse Systems (2nd ed., vol. 3, 1998); Ansel et al., Pharmaceutical Dosage Forms & Drug Delivery Systems (7th ed. 2000); Martindale, The Extra Pharmacopeia (31st edition), Remington's Pharmaceutical Sciences (16th-20th editions); The Pharmacological Basis Of Therapeutics, Goodman and Gilman, Eds. (9th ed.-1996); Wilson and Gisvolds' Textbook Of Organic Medicinal And Pharmaceutical Chemistry, Delgado and Remers, Eds. (10th ed.-1998), and U.S. Pat. Nos. 5,708,025 and 5,994,106. Principles of formulating pharmaceutically acceptable compositions also are described in, e.g., Platt, Clin. Lab Med., 7:289-99 (1987), Aulton, Pharmaceutics: The Science Of Dosage Form Design, Churchill Livingstone (New York) (1988), Extemporaneous Oral Liquid Dosage Preparations, CSHP (1998), and "Drug Dosage," J. Kans. Med. Soc., 70 (I), 30-32 (1969). Additional pharmaceutically acceptable carriers particularly suitable for administration of Anti-KIR antibody compositions and related compositions (e.g., compositions comprising Anti-KIR antibody-encoding nucleic acids or Anti-KIR antibody-encoding nucleic acid comprising vectors) are described in, for example, International Patent Application WO 98/32859.

Anti-KIR antibody compositions can be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid, and combinations of any thereof, so as to provide such a composition. Methods for the preparation of such compositions are known. See, e.g., Sustained and Controlled Release Drug Delivery Systems, J. R. Robinson, ed., Marcel Dekker, Inc., New York, 1978.

In another aspect, compositions of the invention orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In the case of combination compositions (discussed further herein), Anti-KIR antibodies can be coformulated with and/or coadministered with one or more additional therapeutic agents (e.g., an antigenic peptide and/or an immunostimulatory cytokine). Such combination therapies may require lower dosages of the Anti-KIR antibody and/or the coadministered agents, thus avoiding possible toxicities or complications associated with the various monotherapies.

B. Combination Compositions and Therapies

The invention further provides compositions comprising one or more Anti-KIR antibodies in combination with one or more additional active agents (agents that induce, promote, and/or enhance a biological response in at least a substantial proportion of a target host population in a predictable manner). For example, Anti-KIR antibodies can be combined with an immunomodulatory agent, a hormonal agent, a chemotherapeutic agent, an anti-angiogenic agent, an apoptotic agent, a second antibody, an anti-infective agent, a combination of two or more thereof, etc. Both general Anti-KIR antibody combination compositions (combinations that relate to promoting and/or enhancing NK cell activity in the context of any condition) and combination compositions specific to the treatment of cancer are described in some detail here.

Unless otherwise stated or clearly contradicted by context, any of the various combinations described here also may be used in the context of combination therapies, which are further described elsewhere herein.

1. General Combinations

In one aspect, the invention provides Anti-KIR antibody combination compositions ("combination compositions") that further comprise an at least physiologically effective amount, and desirably a therapeutically effective amount, of one or more cytokines that exhibit the ability to substantially increase NK lytic activity in the absence of induction. A number of cytokines have been shown to exhibit such activity. Examples of such cytokines include IFNα, IFNβ, IL-12, and IL-18.

In another aspect, the invention provides a combination composition that comprises at least a physiologically effective amount, and desirably a therapeutically effective amount, of one or more cytokines that induce IFNγ production by NK cells. Examples of such cytokines include IL-12 and IL-18.

In still another aspect, the invention provides a combination composition comprising a cytokine or combination of cytokines that is able to activate NK cells and induce them to proliferate (to obtain a so-called lymphokine activated killer (LAK) phenotype) in an amount and concentration suitable therefor. IL-2, for example, can be used to induce such effects in NK cells.

In a further aspect, the invention provides a combination composition that comprises a cytokine or combination of cytokines that is able to at least partially override NK inhibitory receptor signals in an amount effective therefor. IFNγ in combination with IL-12 and/or IL-18, for example, has been demonstrated to override NK inhibitory signals.

In another exemplary aspect, the invention provides a combination composition comprising a combination of IL-2 and IFNα in amounts sufficient to enhance NK cell activity.

2. Combination Compositions for Cancer Treatment

In a more particular aspect, the invention provides combination compositions that are useful in the treatment of cancer. Such combinations are characterized by the inclusion of at least one Anti-KIR antibody and at least one second agent that induces or promotes physiological effects that are associated with the treatment of cancer or that enhances the effect of the Anti-KIR antibody(s) in the composition with respect to the treatment of cancer. Such a secondary agent can be any suitable antineoplastic therapeutic agent, such as an antineoplastic immunogenic peptide, antibody, or small molecule drug.

Drugs employed in cancer therapy may have a cytotoxic or cytostatic effect on cancer cells, or may reduce proliferation of the malignant cells. Among the texts providing guidance for cancer therapy is Cancer, Principles and Practice of Oncology, 4th Edition, DeVita et al., Eds. J. B. Lippincott Co., Philadelphia, Pa. (1993). An appropriate therapeutic approach is chosen according to such factors as the particular type of cancer and the general condition of the patient, as is recognized in the pertinent field.

a. Anti-cancer mAbs

In a particular facet, the invention provides a composition comprising an Anti-KIR antibody or other Anti-KIR antibody and a suitable second anti-cancer mAb (which may include a full length mAb, a mAb fragment, or a mAb derivative). Any mAb that does not significantly interfere with the specificity, selectivity, and/or affinity of the Anti-KIR antibody anti-body or other Anti-KIR antibody (e.g., does not cause more than about 5%, more than about 10%, or more than about 20% competition for NKCAMR binding by the Anti-KIR antibody antibody).

Examples of suitable secondary anti-cancer mAbs include anti-CD20 mAbs (such as Rituximab and HuMax-CD20), anti-Her2 mAbs (e.g., Trastuzumab), anti-CD52 mAbs (e.g., Alemtuzumab and CAMPATH 1H), anti-EGFR mAbs (e.g., Cetuximab, HuMax-EGFr, and ABX-EGF), Zamyl, Pertuzumab, anti-A33 antibodies (see U.S. Pat. No. 6,652,853), anti-oncofetal protein mAbs (see U.S. Pat. No. 5,688,505), anti-PSMA mAbs (see, e.g., U.S. Pat. No. 6,649,163), anti-TAG-72 antibodies (see U.S. Pat. No. 6,207,815), anti-aminophospholipid antibodies (see U.S. Pat. No. 6,406,693), anti-neurotrophin antibodies (U.S. Pat. No. 6,548,062), anti-C3b(i) antibodies (see U.S. Pat. No. 6,572,856), anti-MN antibodies (see, e.g., U.S. Pat. No. 6,051,226), anti-mts1 mAbs (see, e.g., U.S. Pat. No. 6,638,504), and anti-VEGF mAbs (e.g., bevacizumab). Other possibly suitable second mAb molecules include alemtuzumab, edrecolomab, tositumomab, Ibritumomab tiuxetan, and gemtuzumab ozogamicin. Additional antibodies that can be useful components of combination compositions or combination administration methods of the invention include antibodies against tissue factor and antibodies against killer Ig-like receptor (anti-KIR antibodies). Where appropriate the targets for these antibodies also can be targeted by multispecific Anti-KIR antibodies of the invention. Where appropriate such antibodies can be conjugated to a cytotoxin, radionuclide, or other anti-cancer agent. Also where appropriate, immunogenic peptide targets of such antibodies can be used to induce an immune response in a combination composition or combination administration method of the invention. IL-20, IL-21, antibodies thereto, and related anti-idiotypic antibodies also can be useful components in such compositions or methods.

Other antibodies developed against lymphomas, leukemia cells, micrometastases, and solid tumors also may be useful in combination methods and/or combination compositions of the invention. Antibodies that inhibit functions vital for tumor cell survival, growth, invasiveness and/or migration; antibodies that induce ADCC or CDC against tumor/cancer cells; antibodies that interrupt key cancer progression-related signaling events; and/or that deliver a toxic payload to preneoplastic and/or neoplastic cells can be particularly useful in such methods and compositions. Death of the tumor cells also might lead to the release of tumor antigens that "vaccinate" the immune system and stimulates it to produce a secondary response that then targets tumor/cancer cells. Thus, in one aspect, the invention provides a method of targeting a particular population of cancer cells or tumor(s) followed by monitoring of the patient for a secondary response, and providing further anti-cancer therapy if such secondary response is deemed unsatisfactory. Overexpressed oncogenes and tumor-specific antigens can be advantageous targets for such antibodies. Tumor antigens, which can be useful in this context or in their own right as immunogenic peptides ("vaccines") are described in, for example, Stauss et al.: Tumor antigens recognized by T cells and antibodies. Taylor and Frances (2003) and Durrant et al., Expert Opin. Emerging Drugs 8(2):489-500 (2003)).

In another aspect, the invention provides combination compositions and combination administration methods involving second antibodies, which are nonsimilar to NKCAMR antibodies, such as anti-HER-2/neu antibodies, anti-PSAn antibodies, etc. Additional examples of such antibodies are described elsewhere herein. In another aspect, a combination composition and/or combination administration method involves an Anti-KIR antibody anti-idiotypic or anti-anti-idiotypic antibody alone or in addition to an Anti-KIR antibody.

b. Chemotherapy

In another aspect, the invention provides combination compositions and combination therapy methods involving a chemotherapeutic agent delivered to a host in association with an anti-cancer Anti-KIR antibody. For example, in one aspect, the invention provides a combination therapy comprising administering an anti-cancer Anti-KIR antibody in association with CHOP or CHOP-R chemotherapy (therapy comprising an anti-cancer effective combination of cyclophosphamide, doxorubicin, vincristine, prednisone and Rituxan), such that an at least additive anti-cancer effect (if not a greater than additive effect) in a patient in need of such treatment or at substantial risk of developing a disease, disorder, or condition wherein such treatment is beneficial in, e.g., reducing the severity of an imminent cancer, reducing the spread of an imminent cancer, reducing the likelihood of developing cancer, reducing the effects of an imminent cancer, or a combination of any thereof, etc.

In a particular aspect, the Anti-KIR antibody or related composition is delivered in association with a chemotherapeutic that acts on the DNA level of cancer progression (non-limiting examples of conventional chemotherapeutic agents at the DNA level include anti-metabolites (such as 6-mercaptopurine, 6-thioguanine, methotrexate, 5-fluorouracil, and hydroxyurea), cytarabine, alkylating agents, procarbazine, topoisomerase inhibitors, platinum derivatives, anthracyclines, and antibiotics)).

In another particular aspect, the Anti-KIR antibody or related composition is delivered to a subject or comprised in a composition with an "RNA level" chemotherapeutic agent (or combination thereof), nonlimiting examples of which include L-asparaginase, Vinca alkaloid, taxanes, anti-cancer taxane combination compositions (such as docetaxel-plus-prednisone), and topoisomerase inhibitors. In another particular aspect, an Anti-KIR antibody and/or related composition is delivered in association with an effective dose of dacarbazine (DTIC).

Anti-KIR antibodies also or alternatively can be administered with one or more anti-cancer cytotoxic agents/chemotherapeutic agents selected from cyclophosphamide, taxol (and other taxanes, such as docetaxel, paclitaxel, and the like), 5-fluorouracil, adriamycin, cisplatin, methotrexate, oxaliplatin, irinotecan, topotecan, leucovorin, carmustine, streptozocin, cytosine arabinoside, mitomycin C, prednisone, vindesine, carbaplatinum, and vincristine.

A general discussion of cytotoxic agents used in chemotherapy which can provide further compositions, methods, and related principles useful in the context of chemotherapy combination compositions and administration methods is provided in, e.g., Sathe. M. et al., Cancer Chemotherapeutic Agents: Handbook of Clinical Data (1978) and the second edition thereof (Preston-1982), and Cancer Chemotherapeutic Agents (ACS Professional Reference Book) (William Foye, Ed. 1995), A number of additional agents that can be useful in such contexts are set forth in Table C of U.S. Pat. No. 6,524,583.

c. Anti-cancer Nucleic Acids

In another exemplary aspect, the invention provides a combination composition or combination administration method, wherein an Anti-KIR antibody is combined or associated with an anti-cancer nucleic acid. For example, an Anti-KIR antibody can be combined with or administered in association with an anti-cancer antisense nucleic acid (e.g., GENASENSE (augmerosen/G3139)), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2—see, e.g., Benimetskaya et al., Clin Prostate Cancer. 2002 June; 1(1):20-30; Tortora et al., Ann N Y Acad. Sci. 2003 December; 1002:236-43; Gleave et al., Ann N Y Acad. Sci. 2003 December; 1002:95-104.; Lahn et al., Ann N Y Acad. Sci. 2003 December; 1002:263-70; Kim et al., Int J Oncol. 2004 January; 24(1):5-17; Stahel et al., Lung Cancer. 2003 August; 41 Suppl 1:S81-8; Stephens at al., Curr Opin Mol. Ther. 2003 April; 5(2):118-22; Cho-Chung, Arch Pharm Res. 2003 March; 26(3):183-91; and Chen, Methods Mol. Med. 2003; 75:621-36)).

In another aspect, an Anti-KIR antibody is administered in association with or combined in a composition with an anti-cancer inhibitory RNA molecule (see, e.g., Lin et al., Curr Cancer Drug Targets. 2001 November; 1(3):241-7, Erratum in: Curr Cancer Drug Targets. 2003 June; 3(3):237; Lima et al., Cancer Gene Ther. 2004 May; 11(5):309-16; Grzmil et al., Int J Oncol. 2004 January; 24(1):97-105; Collis et al., Int J Radiat Oncol Biol Phys. 2003 Oct. 1; 57(2 Suppl):S144; Yang et al., Oncogene. 2003 Aug. 28; 22(36): 5694-701; and Zhang et al., Biochem Biophys Res Commun. 2003 Apr. 18; 303(4):1169-78)).

In another facet, the invention provides combination compositions and combination administration methods where an Anti-KIR antibody is combined with an anti-cancer nucleozyme, such as a ribozyme, an example of which is angiozyme (Ribozyme Pharmaceuticals) (see e.g., Pennati at al., Oncogene. 2004 Jan. 15; 23(2):386-94; Tong et al., Clin Lung Cancer. 2001 February; 2(3):220-6; Kijima et al., Int J Oncol. 2004 March; 24(3):559-64; Tong et al., Chin Med J (Engl). 2003 October; 116(10):1515-8; and Orlandi et al., Prostate. 2003 Feb. 1; 54(2):133-43). In yet another aspect, an Anti-KIR antibody is combined with an immunostimulatory nucleic acid (see, e.g., Krieg, Trends in Microbiol 7: 64-65 (1999); Wooldridge et al., Curr Opin Oncol. 2003 November; 15(6):440-5; Jahrsdorfer et al., Semin Oncol. 2003 August; 30(4):476-82; Jahrsdorfer et al., Curr Opin Investig Drugs. 2003 June; 4(6):686-90; and Carpentier et al., Front Biosci. 2003 Jan. 1; 8:e115-27).

In another aspect, the invention provides combination compositions and methods, wherein an Anti-KIR antibody is combined with or administered in association with a tumor suppressor-encoding nucleic acid. In one exemplary aspect, the tumor suppressor is a p53 tumor suppressor gene (see, e.g., Roth at al., Oncology (Huntingt). 1999 October; 13(10 Suppl 5):148-54) and Nielsen et al., Cancer Gene Ther. 1998 January-February; 5(1):52-63). Additional tumor suppressor targets include, for example, BRCA1, RB1, BRCA2, DPC4 (Smad4), MSH2, MLH1, and DCC.

d. Oncolytic Viruses

In another aspect, the invention provides combination compositions and combination administration methods wherein an Anti-KIR antibody is combined or coadministered with an oncolytic virus. Examples of such viruses include oncolytic adenoviruses and herpes viruses, which may or may not be modified herpes viruses (examples of such viruses and related principles thereto are described in, e.g., Teshigahara et al., J Surg Oncol. 2004 January; 85(1): 42-7; Stiles et al., Surgery. 2003 August; 134(2):357-64; Zwiebel et al., Semin Oncol. 2001 August; 28(4):336-43; Varghese et al., Cancer Gene Ther. 2002 December; 9(12): 967-78; and Wildner et al., Cancer Res. 1999 Jan. 15; 59(2):410-3).

Viruses, viral proteins, and the like also can be used in combination compositions and combination administration methods. Replication-deficient viruses, that generally are capable of one or only a few rounds of replication in vivo, and that are targeted to tumor cells, can, for example, be useful components of such compositions and methods. Such viral agents can comprise or be associated with nucleic acids encoding immunostimulants, such as GM-CSF and/or IL-2. Both naturally oncolytic and such recombinant oncolytic viruses (e.g., HSV-1 viruses; reoviruses; replication-deficient and replication-sensitive adenovirus; etc.) can be useful components of such methods and compositions (see, e.g., Varghese et al., Cancer Gene Ther. 2002 December; 9(12): 967-78; Zwiebel et al., Semin Oncol. 2001 August; 28(4): 336-43; Sunarmura et al., Pancreas. 2004 April; 28(3):326-9; Shah at al., J Neurooncol. 2003 December; 65(3):203-26; and Yamanaka, Int J Oncol. 2004 April; 24(4):919-23).

e. Cancer "Vaccines"

As an additional feature, the invention provides combination administration methods and combination compositions wherein an Anti-KIR antibody is delivered in association with an anti-cancer immunogen, such as a cancer antigen/tumor-associated antigen (e.g., an epithelial cell adhesion molecule (Ep-CAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and the like, additional examples of which are described elsewhere herein) (see also, e.g., Acres et al., Curr Opin Mol Ther 2004 February, 6:40-7; Taylor-Papadimitriou et al., Biochim Biophys Acta. 1999 Oct. 8; 1455(2-3):301-13; Emens et al., Cancer Biol Ther. 2003 July-August; 2(4 Suppl 1):S161-8; and Ohshima et al., Int J Cancer. 2001 Jul. 1; 93(1):91-6). A number of other suitable cancer antigens/tumor-associated antigens described elsewhere herein (e.g., gp75) and similar molecules known in the art also or alternatively can be used in such combination administration methods or incorporated in such combination compositions. Anti-cancer immunogenic peptides also include anti-idiotypic "vaccines" such as BEC2 anti-idiotypic mAb (Mitumomab—see, e.g., Chapman, Curr Opin Investig Drugs. 2003 June; 4(6):710-5 and McCaffery et al., Clin Cancer Res. 1996 April; 2(4):679-86), CEAVAC and related anti-idiotypic mAbs (see, e.g., Foon et al., J Clin Oncol. 1999 September; 17(9):2889-5), anti-idiotypic mAb to MG7 mAb (see, e.g., Fengtian et al., Chin Med Sci J. 2002 December; 17(4):215-9), and other anti-cancer anti-idiotypic Abs (see, e.g., Birebent et al., Vaccine. 2003 Apr. 2; 21(15):1601-12, Li et al., Chin Med J (Engl). 2001 September; 114(9):962-6, Schmitt et al., Hybridoma. 1994 October; 13(5):389-96, Maloney et al., Hybridoma. 1985 Fall;4(3): 191-209, Raychardhuri et al., J Immunol. 1986 Sep. 1; 137(5):1743-9, Pohl et al., Int J Cancer. 1992 Apr. 1; 50(6):958-67, Bohlen et al., Cytokines Mol. Ther. 1996 December; 2(4):231-8, and Maruyama, J Immunol Methods. 2002 Jun. 1; 264(1-2):121-33). Such anti-idiotypic Abs can be advantageously optionally conjugated to a carrier, which may be a synthetic (typically inert) molecule carrier, a protein (e.g., keyhole limpet hemocyanin (KLH) (see, e.g., Ochi et al., Eur J Immunol. 1987 November; 17(11):1645-8)), or a cell (e.g., a red blood cell—see, e.g., Wi et al., J Immunol Methods. 1989 Sep. 1; 122(2):227-34)).

Compositions and combination administration methods of the invention also include the inclusion or coadministration of nucleic acid vaccines, such as naked DNA vaccines encoding such cancer antigens/tumor-associated antigens (see, e.g., U.S. Pat. Nos. 5,589,466, 5,593,972, 5,703,057, 5,879,687, 6,235,523, and 6,387,888). In another aspect, the combination administration method and/or combination composition comprises an autologous vaccine composition. In a further aspect, the combination composition and/or combination administration method comprises a whole cell vaccine or cytokine-expressing cell (e.g., a recombinant IL-2 expressing fibroblast, recombinant cytokine-expressing dendritic cell, and the like) (see, e.g., Kowalczyk et al., Acta Biochim Pol. 2003; 50(3):613-24; Reilly et al., Methods Mol. Med. 2002; 69:233-57; Ferlazzo et al., J. Exp. Med., 153):343-351 (2002); and Tirapu et al., Curr Gene Ther. 2002 February; 2(1):79-89). Another example of a therapeutic autologous cell method that can be useful in combination methods of this invention is the MYVAX Personalized Immunotherapy method (previously referred to as GTOP-99) (available through Genitope Corporation—Redwood City, Calif., USA) (see U.S. Pat. Nos. 5,972,334 and 5,776,746). In a different aspect, the inventive methods can be practiced by methods that also or alternatively comprise co-delivery of one or more types of NK cells (e.g., a population of $CD56^{dim}CD^{16+}$NK cells), which can be genetically modified and/or modified by various contact with substances (e.g., one or more activating factors) prior to delivery.

f. Anti-cancer Cytokines

In another aspect, the invention provides a combination composition or combination administration method comprising an Anti-KIR antibody and an anti-cancer cytokine, chemokine, or combination thereof. Any suitable anti-cancer cytokine and/or chemokine can be used with and/or combined with Anti-KIR antibodies in the methods and compositions of the invention. Suitable chemokines and cytokines result in a detectably greater and/or more comprehensive immune response to cancer cells or related tissues (e.g., tumors) in vivo and do not substantially impede the binding of the Anti-KIR antibody(s) in the composition/method. Examples of suitable cytokines and growth factors include IFNγ, IL-1α, IL-1β, IL-2, IL-4, IL-5, IL-6, IL-7, IL-8, IL-9, IL-10, IL-11, IL-12, IL-13, IL-15, IL-18, IL-21, IL-23, IL-24, IL-27, IL-28a, IL-28b, IL-29, KGF, TGFβ, M-CSF, G-CSF, TNFβ, LAF, TCGF, BCGF, TRF, BAF, BDG, MP, LIF, OSM, TMF, PDGF, IFN-alpha, IFNβ, IFNγ, IFNαs (e.g., INFα2b), IFNβ, GM-CSF, CD40L, Flt3 ligand, stem cell factor, ancestim, and TNFα (see, e.g., Dranoff, Nat Rev Cancer. 2004 January; 4(1):11-22 and Szlosarek, Novartis Found Symp. 2004; 256:227-37; discussion 237-40, 259-69). Suitable chemokines can include Glu-Leu-Arg (ELR)-negative chemokines such as IP-10, MCP-3, MIG, and SDF-1 alpha from the human CXC and C—C chemokine families. Suitable cytokines also include cytokine derivatives, cytokine variants, cytokine fragments, and cytokine fusion proteins (see, e.g., Eliason. BioDrugs, 2001; 15(11): 705-11 (with respect to PEGylated cytokines); Shibuya et al., Laryngoscope. 2003 November; 113(11):1870-84 (other cytokine derivatives); U.S. Pat. Nos. 5,229,109, 5,153,310, 5,312,903, 6,929,791, 6,825,334, 6,168,785, 4,851,512, and 6,906,170 and Fallon et al., J Biol. Chem. 2000 Mar. 10; 275(10):6790-7, Chang et al., Mol Pharmacol. 1995 January; 47(1):206-11; Berndt et al., Biochemistry. 1994 May 31; 33(21):6571-7; Bulchi et al., Arch Biochem Biophys. 1993 December; 307(2):411-5; Teppler et al., J Infect Dis. 1993 February; 167(2):291-8, Landgraf et al., J Biol. Chem. 1992 Sep. 15; 267(26):18511-9; and Landgraf et al., Proteins. 1991; 9(3):207-16 (with respect to exemplary IL-2 analogues and derivatives—the use of IL-2 as a standalone therapeutic agent (e.g., in terms of dosage, administration, etc.) is well-known (see, e.g., WO 2004/056392)) and International Patent Application WO 01/79258 (albumin-cytokine fusion proteins)). As indicated elsewhere herein, these and other methods involving naturally occurring peptide-encoding nucleic acids herein can alternatively or additionally performed by "gene activation" and homologous recombination gene upregulation techniques, such as are described in U.S. Pat. Nos. 5,968,502, 6,063,630, and 6,187, 305 and European Patent Publication 0 505 500. In such aspects, an Anti-KIR antibody can be "delivered" to a cell by an Anti-KIR antibody-encoding nucleic acid or a vector or cell comprising the same.

g. Adjuvants

In another aspect, the invention provides combination compositions and combination administration methods comprising an Anti-KIR antibody and an adjuvant, typically in further combination with an anti-cancer immunogenic peptide. Non-limiting examples of suitable adjuvants are QS21, GM-CSF, SRL-172, histamine dihydrochloride, thymocartin. Tio-TEPA, monophosphoryl-lipid A/micobacteria compositions, alum, incomplete Freund's Adjuvant, Montanide ISA, Ribi Adjuvant System, TiterMax adjuvant, syntex adjuvant formulations, immune-stimulating complexes (ISCOMs), Gerbu$^R$ adjuvant, CpG oligodeoxynucleotides, lipopolysaccharide, and polyinosinic:polycytidylic acid.

h. Tumor Internalization Promoters

In a further aspect, the invention provides combination compositions and combination methods that involve delivery of one or more agents that promote access of the Anti-KIR antibody to the interior of a tumor. Thus, for example, such methods can be performed in association with the delivery of a relaxin that facilitates tumor access (see, e.g., U.S. Pat. No. 6,719,977). As another example of such a technique, an Anti-KIR antibody or related compound (e.g., an Anti-KIR antibody-encoding nucleic acid or vector comprising the same) can be bonded/fused to a cell penetrating peptide (CPP). Cell penetrating peptides and related peptides (such as engineered cell penetrating antibodies) are known in the art and described in, e.g., Zhao et al., J Immunol Methods. 2001 Aug. 1; 254(1-2):137-45; Hong et al., Cancer Res. 2000 Dec. 1; 60(23):6551-6; Lindgren et al., Biochem J. 2004 Jan. 1; 377(Pt 1):69-76; Buerger et al., J Cancer Res Clin Oncol. 2003 December; 129(12):669-75; Pooga et al., FASEB J. 1998 January; 12(1):67-77; and Tseng et al., Mol. Pharmacol. 2002 October; 62(4):864-72. Intratumoral administration of Anti-KIR antibodies or vectors comprising Anti-KIR antibody-encoding nucleic acid sequence(s) also or alternatively can be used to facilitate therapeutic regimen aspects of the invention.

i. Telomerase and Telomerase-related Compositions

In yet another aspect, the invention provides combination compositions and combination administration methods comprising a telomerase inhibitor, telomerase vaccine, or combination thereof in addition to at least one Anti-KIR antibody or related molecule. Examples of such compositions and related techniques and principles are described in, e.g., U.S. Pat. Nos. 6,440,735 and 6,713,055.

j. Immunomodulators

In a further aspect, combination compositions and/or combination administration methods of the invention comprise administration of an immunomodulatory compound or modulator thereof (e.g., an anti-inhibitory immunomodulatory antibody). Examples of such compounds include B7 molecules (B7-1. B7-2, variants thereof, and fragments thereof) (see, e.g., Adv Exp Med. Biol. 2000; 465:381-90), ICOS, and OX40 (see Coyle et al., Springer Semin Immunopathol. 2004 February; 25(3-4):349-59). Another example of such a molecule is an inhibitor of a negative T cell regulator, such as an antibody against CTLA4 or against another negative immune cell regulator, such as BTLA and PD-1. In another aspect, delivery of such inhibitory molecules may be desired, for example in the treatment of autoimmune diseases or other immune system related disorders. In a further exemplary aspect, an inhibitor of CD4, such as an anti-CD4 antibody can be delivered in association with practice of inventive methods provided here.

In another facet, a combination composition or combination administration method comprises one or more immunosuppressive/immunomodulatory agents, such as a T lymphocyte homing modulator (e.g., FTY-720—see, e.g., Yangawa et al., J Immunol. 1998 Jun. 1; 160(11):5493-9); a calcineurin inhibitor (such as valspodar, PSC 833, and other MDR-1 or p-glycoprotein inhibitors); or a TOR-inhibitor (e.g., sirolimus, everolimus, and rapamcyin).

k. Cell Cycle Control & Apoptosis-Related Agents

In another aspect, the invention provides combination compositions and combination administration methods that involve at least one Anti-KIR antibody and one or more cell cycle control/apoptosis regulators (or cell cycle/apoptosis "regulating agents"). A cell cycle control/apoptosis regulator can include, for example, one or more molecules that target and modulate cell cycle control/apoptosis regulators such as (i) cdc-25 (with NSC 663284 as a non-limiting example (see, e.g., Pu et al (2003) J Biol Chem 278, 46877)), (ii) cyclin-dependent kinases that overstimulate the cell cycle (non-limiting examples of which are flavopiridol (L868275, HMR1275; Aventis), 7-hydroxystaurosporine (UCN-01, KW-2401; Kyowa Hakko Kogyo), and roscovitine (R-roscovitine, CYC202; Cyclacel)—as reviewed by Fischer & Gianella-Borradori (2003) Exp Op Invest Drugs 12, 955-970), and (iii) telomerase modulators (such as BIBR1532 (Damm et al (2001) EMBO J 20, 6958-6968) and SOT-095 (Tauchi et al (2003) Oncogene 22, 5338-5347)). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2 (see Igney and Krammer (2002) Nature Rev. Cancer 2, 277-288; Makin and Dive (2003) Trends Mol Med 9, 2519; Smyth et al (2003) Immunity 18, 1-6; Panaretakis et al (2003) Oncogene 22, 4543-4556; and references cited therein).

l. Growth Factor Inhibitors

In yet another aspect, the invention provides combination compositions and combination administration methods that comprise one or more growth factor inhibitors. A number of mAbs against growth factors and growth factor receptors are known that can be useful in promoting the treatment of cancer. For example, antibodies against the extracellular ligand binding domain of epidermal growth factor receptor (EGF-R) proteins that are abnormally activated in epithelial tumors can be useful in the treatment of aggressive epithelial cell-derived tumors. Antibodies against low molecular weight molecules that inhibit the tyrosine kinase domains of such receptors also can be useful in combination compositions or combination administration methods. Non-limiting examples of such mAbs are Herceptin (monoclonal antibody), cetuximab (monoclonal antibody), Xolair (Omalizumab), Tarceva (low molecular weight inhibitor), and Iressa (low molecular weight inhibitor). Additional related and useful antibodies suitable for inclusion in such combination compositions and administration methods are described elsewhere herein.

m. Angiogenesis Inhibitors

Other features of the invention include combination compositions and combination administration methods that comprise an inhibitor of angiogenesis, neovascularization, and/or other vascularization delivered in association with one or more Anti-KIR antibodies. Nonlimiting examples of such agents include endostatin and angiostatin (reviewed in Marx (2003) Science 301, 452-454) and derivatives/analogues thereof; anti-angiogenic heparin derivatives and related molecules (e.g., heperinase III); VEGF-R kinase inhibitors and other anti-angiogenic tyrosine kinase inhibitors (e.g., SU011248—see Rosen et al., Clinical Oncology; May 31-Jun. 3, 2003, Chicago, Ill., USA (abstract 765)); temozolomide; NEOVASTAT (Gingras et al., Invest New Drugs.

2004 January; 22(1):17-26); ANGIOZYME (Weng et al., Curr Oncol Rep. 2001 March; 3(2):141-6); NK4 (Matsumoto et al., Cancer Sci. 2003 April; 94(4):321-7); macrophage migration inhibitory factor (MIF); cyclooxygenase-2 inhibitors; resveratrol (see, e.g., Sala et al., Drugs Exp Clin Res. 2003; 29(5-6):263-9); PTK787/ZK 222584 (see, e.g., Klem, Clin Colorectal Cancer. 2003 November; 3(3):147-9 and Zips et al., Anticancer Res. 2003 September-October; 23(5A):3869-76); anti-angiogenic soy isoflavones (e.g., Genistein—see, e.g., Sarkar and L1, Cancer Invest. 2003; 21(5):744-57); Oltipraz; thalidomide and thalidomide analogs (e.g., CC-5013—see, e.g., Tohnya et al., Clin Prostate Cancer. 2004 March; 2(4):241-3); other endothelial cell inhibitors (e.g., Squalamine and 2-methoxyestradiol); fumagillin and analogs thereof; somatostatin analogues; pentosan polysulfate; tecogalan sodium; molecules that block matrix breakdown (such as suramin and analogs thereof (see, e.g., Marchetti et al., Int J Cancer. 2003 Mar. 20; 104(2):167-74, Meyers et al., J Surg Res. 2000 Jun. 15; 91(2):130-4, Kruger and Figg, Clin Cancer Res. 2001 July; 7(7):1867-72, and Gradishar et al., Oncology. 2000 May; 58(4):324-33)); dalteparin (Scheinowitz et al., Cardiovasc Drugs Ther. 2002 July; 16(4):303-9); and matrix metalloproteinase inhibitors (such as BMS-275291—see Rundhaug, Clin Cancer Res. 2003 February; 9(2):551-4; see generally, Coussens et al. Science 2002; 295:2387-2392); monoclonal antibodies targeted against angiogenic agents and/or their receptors, such as VEGF, bFGF, and angiopoietin-1; and monoclonal antibodies against other relevant targets (such as anti-alpha-v/beta-3 integrin and anti-kininostatin mAbs) (see also, generally. Reisfeld et al., Int Arch Allergy Immunol. 2004 March; 133(3):295-304; Mousa et al., Curr Pharm Des. 2004; 10(1):1-9; Shibuya, Nippon Yakurigaku Zasshi. 2003 December; 122(6):498-503; Zhang et al., Mol. Biotechnol. 2003 October; 25(2):185-200; Kiselev et al., Biochemistry (Mosc). 2003 May; 68(5):497-513; Shepherd, Lung Cancer. 2003 August; 41 Suppl 1:S63-72; O'Reilly, Methods Mol Biol. 2003; 223:599-634; and Zhu et al., Curr Cancer Drug Targets. 2002 June; 2(2):135-56).

n. Hormone Regulating Agents

In yet another aspect, the invention provides combination compositions and combination administration methods wherein at least one Anti-KIR antibody is combined with a hormonal regulating agent, such as an anti-androgen and/or anti-estrogen therapy agent or regimen (see, e.g., Trachtenberg, Can J Urol. 1997 June; 4(2 Supp 1):61-64; Ho, J Cell Biochem. 2004 Feb. 15; 91(3):491-503), tamoxifen, a progestin, a luteinizing hormone-releasing hormone (or an analog thereof or other LHRH agonist), or an aromatase inhibitor (see, e.g., Dreicer et al., Cancer Invest. 1992; 10(1):27-41).

o. Whole-cell Vaccines and Adoptive Immunotherapy

Combination compositions and combination administration methods also or alternatively can involve "whole cell" and "adoptive" immunotherapy methods. For example, such methods can comprise infusion or re-infusion of immune system cells (e.g., tumor-infiltrating lymphocytes (TILs), such as $CD4^+$ and/or $CD8^+$ T cells (e.g., T cells expanded with tumor-specific antigens and/or genetic enhancements), antibody-expressing B cells or other anti-body producing/presenting cells, dendritic cells (e.g., anti-cytokine expressing recombinant dendritic cells, dendritic cells cultured with a DC-expanding agent such as GM-CSF, IL-4, TNFalpha, and/or Flt3-L, and/or tumor-associated antigen-loaded dendritic cells), anti-tumor NK cells, so-called hybrid cells, or combinations thereof (see, e.g., Fishman et al., Expert Rev Anticancer Ther. 2003 December; 3(6):837-49; Whiteside et al., Cancer Immunol Immunother. 2004 March; 53(3):240-8; Conrad et al., Curr Opin Mol. Ther. 2003 August; 5(4):405-12; Trefzer et al., Mol. Biotechnol. 2003 September; 25(1): 63-9; Reinhard et al., Br J Cancer. 2002 May 20; 86(10): 1529-33; Korbelik et al., Int J Cancer. 2001 Jul. 15; 93(2): 269-74; Costa et al., J Immunol. 2001 Aug. 15; 167(4):2379-87; Hanson et al., Immunity. 2000 August; 13(2):265-76; Matsui et al., Int Immunol. 2003 July; 15(7):797-805; and Ho et al., Cancer Cell. 2003 May; 3(5):431-7). Cell lysates also may be useful in such methods and compositions. Cellular "vaccines" in clinical trials that may be useful in such aspects include CANVAXIN, APC-8015 (Dendreon), HSPPC-96 (Antigenics), and MELACINE cell lysates. Antigens shed from cancer cells, and mixtures thereof (see, e.g., Bystryn et al., Clinical Cancer Research Vol. 7, 1882-1887, July 2001), optionally admixed with adjuvants such as alum, also can be advantageous components in such methods and methods. U.S. Pat. No. 6,699,483 provides another example of a whole cell anti-cancer therapy. Additional examples of such whole cell immunotherapies that can be usefully combined in Anti-KIR antibody-related compositions and methods are described elsewhere herein.

p. Immune System and Intracellular Signaling Inhibitors

In another aspect, the invention provides combination compositions and combination administration methods comprising one or more immune system inhibitors Intracellular signaling inhibitors. Examples of such compounds include tyrosine kinase inhibitors (GLEEVEC, imatinib mesylate), modulators of the ras signaling pathway, and regulators of protein trafficking. Other examples include serine/threonine kinase inhibitors, protein-tyrosine phosphatases inhibitors, dual-specificity phosphatases inhibitors, and serine/threonine phosphatases inhibitors.

q. Anti-anergic Agents

Combination compositions and combination administration methods also or alternatively can include anti-anergic agents (e.g., small molecule compounds, proteins, glycoproteins, or antibodies that break tolerance to tumor and cancer antigens). Examples of such compounds include molecules that block the activity of CTLA-4, such as MDX-010 (Phan et al. (2003) Proc. Natl. Acad. Sci. U.S.A. 100: 8372).

r. Internal Vaccination

In yet another aspect, an Anti-KIR antibody can be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that can be used to induce said tumor cell-death induction and internal vaccination methods include conventional chemotherapeutic agents, cell-cycle inhibitors, anti-angiogenesis drugs, monoclonal antibodies, apoptosis-inducing agents, and signal transduction inhibitors.

s. Other Anti-Cancer Agents

Additional agents that can be comprised in the combination compositions and/or combination administration methods of the invention include fluoropyrimidiner carbamates, such as capecitabine; non-polyglutamatable thymidylate synthase inhibitors; nucleoside analogs, such as tocladesine; antifolates such as pemetrexed disodium; taxanes and taxane analogs; topoisomerase inhibitors; polyamine analogs; mTOR inhibitors (e.g., rapamcyin ester); alkylating agents (e.g., oxaliplatin); lectin inhibitors; vitamin D analogs, anti-angiogenesis compounds (e.g., endostatin, angiocol, anti-PDGF mAbs and other PDGF (platelet derived growth factor) inhibitors, PEDFs (pigment epithelium derived growth factors), and the like); carbohydrate processing inhibitors; antimetabolism folate antagonists; thumidylate synthase inhibitors; other antimetabolites (e.g., raltitrexed); ribonuclease reductase inhibitors; dioxolate nucleoside analogs; thimylate syntase inhibitors; gonadotropin-releasing hormone (GRNH) peptides; human chorionic gonadotropin; chemically modified tetracyclines (e.g., CMT-3; COL-3); and cytosine deaminase. Where appropriate, such agents alternatively can be conjugated to an Anti-KIR antibody of the invention.

Other useful components of combination compositions and methods can include, e.g., thymopentin. DTIC, carmustine, carboplatin, vinblastine, temozolomide, vindesine, and thymosin-α. Histone deacetylase inhibitors (e.g., phenylbutyrate) and/or DNA repair agents (e.g., DNA repair enzymes and related compositions such as DIMERICINE (T4 endonuclease V-containing liposome)) also can be useful components of such methods and compositions. Useful prophylactic and therapeutic regimens of the invention also or alternatively can be combined with anti-cancer directed photodynamic therapy (e.g., anti-cancer laser therapy—which optionally can be practiced with the use of photosensitizing agent, see, e.g., Zhang et al., J Control Release. 2003 Dec. 5; 93(2):141-50); anti-cancer sound-wave and shock-wave therapies (see, e.g., Kambe et al., Hum Cell. 1997 March; 10(1):87-94); anti-cancer thermotherapy (see, e.g., U.S. Pat. No. 6,690,976), and/or anti-cancer nutraceutical therapy (see, e.g., Roudebush et al., Vet Clin North Am Small Anim Pract. 2004 January; 34(1):249-69, viii and Rafi, Nutrition. 2004 January; 20(1):78-82). Exemplary combination compositions and combination administration methods also can specifically include a tamoxifen.

In a further aspect a component of combination compositions and methods can include components of combination compositions and methods can include the Oral VEGF receptors tyrosine kinase inhibitor PTK/ZK.

Further teachings relevant to cancer immunotherapy are provided in, e.g., Berczi et al., "Combination Immunotherapy of Cancer" in Neuroimmune Biology Volume 1: New foundation of Biology, Berczi I, Gorczynski R. Editors, Elsevier, 2001; pp. 417-432.

VI. Therapeutic Applications

In another aspect, the invention provides therapeutic methods involving Anti-KIR antibodies, Anti-KIR antibody compositions, and/or related compositions.

Anti-KIR antibodies can be useful in a variety of therapeutic and prophylactic regimens including, for example, the treatment of cancer, viral infections, and immune system-related disorders.

A. Reduction of Cancer Progression

In one exemplary aspect, the invention provides a method of reducing cancer progression in a mammalian host, such as a human patient, having a detectable level of cancer cells comprising administering an Anti-KIR antibody, an Anti-KIR antibody composition, or a related composition (e.g., a nucleic acid encoding an Anti-KIR antibody), in an amount sufficient to detectably reduce the progression of the cancer in the host.

Cancer cells are cells that divide and reproduce abnormally with uncontrolled growth (e.g., by exceeding the "Hayflick limit" of normal cell growth (as described in, e.g., Hayflick, Exp. Cell Res., 37,614 (1965)). "Cancers" generally consist of single or several clones of cells that are capable of partially independent growth in a host (e.g., a benign tumor) or fully independent growth in a host (malignant cancer). Cancer cells arise from host cells via neoplastic transformation ("carcinogenesis").

Terms such as "preneoplastic," "premalignant," and "precancerous" with respect to the description of cells and/or tissues herein refer to cells or tissues having a genetic and/or phenotypic profile that signifies a significant potential of becoming cancerous. Usually such cells can be characterized by one or more differences from their nearest nonneoplastic counterparts that signal the onset of cancer progression or significant risk for the start of cancer progression. Such precancerous changes, if detectable, can usually be treated with excellent results. Accordingly, the delivery of Anti-KIR antibodies to such cells and tissues as part of a prophylactic regimen is an important aspect of the invention. Some cancers have well defined precancer precursors, others do not. In general, a precancerous state will be associated with the incidence of neoplasm(s) or preneoplastic lesion(s). Examples of known and likely preneoplastic tissues include ductal carcinoma in situ (DCIS) growths in breast cancer, cervical intra-epithelial neoplasia (CIN) in cervical cancer, adenomatous polyps of colon in colorectal cancers, atypical adenomatous hyperplasia in lung cancers, and actinic keratosis (AK) in skin cancers. Preneoplastic phenotypes and genotypes for various cancers, and methods for assessing the existence of a preneoplastic state in cells, have been characterized. See, e.g., Medina, J Mammary Gland Biol Neoplasia. 2000 October; 5(4):393-407; Krishnamurthy et al., Adv Anat Pathol. 2002 May; 9(3):185-97; Ponten, Eur J Cancer. 2001 October; 37 Suppl 8:S97-113; Niklinski et al., Eur J Cancer Prev. 2001 June; 10(3):213-26; Walch et al., Pathobiology. 2000 January-February; 68(1):9-17; and Busch, Cancer Surv. 1998; 32:149-79. Gene expression profiles can increasingly be used to differentiate between normal, precancerous, and cancer cells. For example, familial adenomatous polyposis genes prompt close surveillance for colon cancer; mutated p53 tumor-suppressor gene flags cells that are likely to develop into aggressive cancers; osteopontin expression levels are elevated in premalignant cells, and increased telomerase activity also can be a marker of a precancerous condition (e.g., in cancers of the bladder and lung).

"Cancer progression" refers to any event or combination of events that promote, or which are indicative of, the transition of a normal, non-neoplastic cell to a cancerous, neoplastic cell, the migration of such neoplastic cells, and the formation and growth of tumors therefrom (which latter aspect can be referred to as tumor progression). Examples of such events include phenotypic cellular changes associated with the transformation of a normal, non-neoplastic cell to a recognized pre-neoplastic phenotype, and cellular phenotypic changes that indicate transformation of a pre-neoplastic cell to a neoplastic cell.

Aspects of cancer progression (also referred to herein as "cancer progression stages") include cell crisis, immortalization and/or normal apoptotic failure, proliferation of immortalized and/or pre-neoplastic cells, transformation (i.e., changes which allow the immortalized cell to exhibit anchorage-independent, serum-independent and/or growth-factor independent, or contact inhibition-independent growth, or that are associated with cancer-indicative shape changes, aneuploidy, and focus formation), proliferation of transformed cells, development of metastatic potential, migration and metastasis (e.g., the disassociation of the cell from a location and relocation to another site), new colony formation, tumor formation, tumor growth, neotumorogenesis (formation of new tumors at a location distinguishable and not in contact with the source of the transformed cell(s)), and any combinations thereof.

Carcinogenesis is typically associated with the activation of genes that regulate cell growth via bypassing the host cell's regulatory controls (e.g., bypassing or overcoming a host cell's normally active apoptotic signaling pathway(s)) and the reduced expression of tumor-suppressor genes. Multiple genes typically are deregulated in association with the development of fully malignant tumors.

Cancer progression often is also or alternatively described by the general stages of initiation, promotion, and progression. In tumor-forming cancers, for example, cancer progression often is described in terms of tumor initiation, tumor promotion, malignant conversion, and tumor progression (see, e.g., Cancer Medicine, $5^{th}$ Edition (2000) B.C. Decker Inc., Hamilton, Ontario, Canada (Blast et al. eds.)). Tumor initiation, which reflects the presence of morphological, genetic, and/or behavioral changes at the cellular or tissue level (e.g., the induction of mitogenesis, compensatory cell proliferation, preneoplasia and hyperplasia, survival of premalignant or malignant cells (immortalization, immunosuppression), and occurrence of cancer-associated effects on metastatic potential, etc.), typically results from irreversible genetic damage, such as carcinogen-induced mutations. The initiation stage typically is characterized by the conversion of a normal cell to an initiated cell in response to DNA-damaging agents. Tumor promotion comprises the selective clonal expansion of initiated cells. Tumor progression comprises the expression of the malignant phenotype and the tendency of already malignant cells to acquire more aggressive characteristics with time. The promotion stage typically is characterized by the transformation of an initiated cell into a population of preneoplastic cells, due to alterations in gene expression and cell proliferation. The progression stage typically is characterized by the transformation of the preneoplastic cells to a neoplastic cell population as a result of additional genetic alterations.

Terms such as neoplastic transformation or neoplastic conversion also can describe a stage of cancer progression. Neoplastic conversion is the transformation of a preneoplastic cell into one that expresses a neoplastic phenotype. Once neoplastic conversion is complete, cells with altered gene structure need to multiply to express the cancer associated gene structure. Cell duplication determines the rate of expression and the associated cancer risk. Epigenetic events in general, and DNA methylation in particular, are associated with modulating changes from a normal to preneoplastic to neoplastic state. Neoplastic transformation also is associated with the activation of growth regulatory genes, such as growth factor receptors (e.g., erbA, erbB, fims, neu); molecules involved in signal transduction (src, abl, ras); and transcription factors (jun, fos, myc), which often are referred to as cellular oncogenes or "(c) oncogenes". Additional factors involved in neoplastic transformation include genes that inhibit growth (e.g., p53 and Rb) and genes that regulate apoptosis, such as bcl-2. Neoplastic transformation also involves the inappropriate activation of genes that control cell growth.

In another stage of cancer progression, immunogenic tumors typically escape immune-surveillance of the host enabling their growth. Additional related aspects of cancer progression include evasion of apoptosis by the cancer cell, achieving limitless replication potential, achieving self-sufficiency in growth factor expression, achieving abnormal insensitivity to anti-growth signals; achieving sustained angiogenesis, and metastasis.

Metastasis refers to the spread of cancer cells from one site in a medium to another, such as in the tissue(s) of a patient. Metastasis also typically is involved with a number of distinct physiological events, which include the escape of cancer cells from an initial site via lymphatic channels or protease activity; the survival of cancer cells in circulation; arrest in secondary site(s); extravasation into surrounding tissue; initiation and maintenance of growth, and vascularization of metastatic tumor(s). Metastasis also may involve the ability of tumor cells to secrete proteases that allow invasion beyond the immediate location of the primary tumor. A prominent characteristic of malignant phenotype is the propensity for genomic instability and uncontrolled growth.

Metastatic cancer cells typically penetrate the extracellular matrix (ECM) and the basement membrane of the blood vessels to metastasize to a target organ (ectopic site). The EMC consists of proteins embedded in a carbohydrate complex (heparan sulfate peptidoglycans), and proteases surrounding a tumor are active in this breaking down the host tissue. Thus, the penetration of the ECM and basement membranes and breakdown of related host tissues also are relevant aspects of cancer progression. Indeed, there often is a complex mix of the normally consecutive processes of cell attachment, detachment, as well as degradation of extracellular matrix proteins, and migration, which is needed for the locomotion of invasive tumor cells to distant locations. All of these activities are important aspects of cancer progression in the context of the present invention. Thus, for example, delivery of an Anti-KIR antibody, related compound, or combination composition can be used as a means of reducing any one of these physiological activities in association with the treatment of cancer in a patient.

Methods for detecting cancers and cancer progression include (a) clinical examination (symptoms can include swelling, palpable lumps, enlarged lymph nodes, bleeding, visible skin lesions, and weight loss); (b) imaging (X-ray techniques, mammography, colonoscopy, computed tomography (CT and/or CAT) scanning, magnetic resonance imaging (MRI), etc.); (c) immunodiagnostic assays (e.g., detection of CEA, AFP, CA125, etc.); (d) antibody-mediated radioimaging; and (e) analyzing cellular/tissue immunohistochemistry.

Delivering Anti-KIR antibodies to a subject (either by direct administration or expression from a nucleic acid therein, such as from a pox viral gene transfer vector comprising Anti-KIR antibody-encoding nucleic acid sequence(s)) and practicing the other methods of the invention can be used to reduce, treat, prevent, or otherwise ameliorate any suitable aspect of cancer progression. The methods of the invention can be particularly useful in the reduction and/or amelioration of tumor growth, cancer migration, and cancer cell invasiveness, as described further herein. Methods that reduce, prevent, or otherwise ameliorate such aspects of cancer progression, independently and collectively, are advantageous features of the invention.

Additional advantageous aspects of the invention include the reduction of metastases, the reduction of the spread of tumors, the reduction of tumor growth, and combinations of any thereof. Another favorable aspect is the effectiveness of such methods in the treatment of cancers characterized by micrometastases.

The detection of cancer progression can be achieved by any suitable technique, several examples of which are known in the art. Examples of suitable techniques include PCR and RT-PCR (e.g., of cancer cell associated genes or "markers"), biopsy, electron microscopy, positron emission tomography (PET), computed tomography, immunoscintigraphy and other scintegraphic techniques, magnetic resonance imaging (MRI), karyotyping and other chromosomal analysis, immunoassay/immunocytochemical detection techniques (e.g., differential antibody recognition), histological and/or histopathologic assays (e.g., of cell membrane changes), cell kinetic studies and cell cycle analysis, ultrasound or other sonographic detection techniques, radiological detection techniques, flow cytometry, endoscopic visualization techniques, and physical examination techniques. Examples of these and other suitable techniques are described in, e.g., Rieber et al., Cancer Res., 36 (10), 3568-73 (1976), Brinkley et al., Tex. Rep. Biol. Med., 37, 26-44 (1978), Baky et al., Anal. Quant. Cytol., 2 (3), 175-85 (1980), Laurence et al., Cancer Metastasis Rev., 2 (4), 351-74 (1983), Cooke et al., Gut, 25 (7), 748-55 (1984), Kim et al, Yonsei Med. J., 26 (2), 167-74 (1985), Glaves, Prog. Clin. Biol. Res., 212, 151-67 (1986), McCoy et al., Itnmunol. Ser., 53, 171-87 (1990), Jacobsson et al., Med. Oncol. Tumor. Pharmacother., 8 (4), 253-60 (1991), Swierenga et al., IARC Sci. Publ., 165-93 (1992), Hirnle, Lymphology, 27 (3), 111-3 (1994), Laferte et al., J. Cell Biochem., 57 (1), 101-19 (1995), Machiels et al., Eur. J. Cell Biochem., 66 (3), 282-92 (1995), Chaiwun et al., Pathology (Phila), 4 (1), 155-68 (1996), Jacobson et al, Ann. Oncol., 6 (Suppl. 3), S3-8 (1996), Meijer et al., Eur. J. Cancer, 31A (7-8), 1210-11 (1995), Greenman et al., J. Clin. Endocrinol. Metab., 81 (4), 1628-33 (1996), Ogunbiyi et al., Ann. Surg. Oncol., 4 (8), 613-20 (1997), Merritt et al., Arch. Otolaryngol. Head Neck Surg., 123 (2), 149-52 (1997), Bobardieri et al., Q. J. Nucl. Med., 42 (1), 54-65 (1998), Giordano et al., J. Cell Biochem, 70 (1), 1-7 (1998), Siziopikou et al., Breast J., 5 (4), 221-29 (1999), Rasper, Surgery, 126 (5), 827-8 (1999), von Knebel et al., Cancer Metastasis Rev., 18 (1), 43-64 (1999), Britton et al., Recent Results Cancer Res., 157, 3-11 (2000), Caraway et al., Cancer, 90 (2), 126-32 (2000), Castillo et al., Am. J. Neuroadiol., 21 (5), 948-53 (2000), Chin et al., Mayo Clin. Proc., 75 (8), 796-801 (2000), Kau et al., J. Ortohinolaryngol. Relat. Spe., 62 (4), 199-203 (2000), Krag, Cancer J. Sci. Am., 6 (Suppl. 2), S121-24 (2000), Pantel et al., Curr. Opin. Oncol., 12 (1), 95-101 (2000), Cook et al., Q. J. Nucl. Med., 45 (1), 47-52 (2001), Gambhir et al., Clin. Nucl. Med., 26 (10), 883-4 (2001), MacManus et al., Int. J. Radiat. Oncol. Biol. Phys., 50 (2), 287-93 (2001), Olilla et al., Cancer Control., 8 (5), 407-14 (2001), Taback et al., Recent Results Cancer Res., 158, 78-92 (2001), and references cited therein. Related techniques are described in U.S. Pat. Nos. 6,294,343, 6,245,501, 6,242,186, 6,235,486, 6,232,086, 6,228,596, 6,200,765, 6,187,536, 6,080,584, 6,066,449, 6,027,905, 5,989,815, 5,939,258, 5,882,627, 5,829,437, 5,677,125, and 5,455,159 and International Patent Applications WO 01/69199, WO 01/64110, WO 01/60237, WO 01/53835, WO 01/48477, WO 01/04353, WO 98/12564, WO 97/32009, WO 97/09925, and WO 96/15456.

A reduction of cancer progression can include, e.g., any detectable decrease in (1) the rate of normal cells transforming to neoplastic cells (or any aspect thereof), (2) the rate of proliferation of pre-neoplastic or neoplastic cells, (3) the number of cells exhibiting a preneoplastic and/or neoplastic phenotype, (4) the physical area of a cell media (e.g., a cell culture, tissue, or organ (e.g., an organ in a mammalian host)) comprising pre-neoplastic and/or neoplastic cells, (5) the probability that normal cells and/or preneoplastic cells will transform to neoplastic cells, (6) the probability that cancer cells will progress to the next aspect of cancer progression (e.g., a reduction in metastatic potential), or (7) any combination thereof. Such changes can be detected using any of the above-described techniques or suitable counterparts thereof known in the art, which typically are applied at a suitable time prior to the administration of a therapeutic regimen so as to assess its effectiveness. Times and conditions for assaying whether a reduction in cancer potential has occurred will depend on several factors including the type of cancer, type and amount of Anti-KIR antibody, related composition, or combination composition being delivered to the host. The ordinarily skilled artisan will be able to make appropriate determinations of times and conditions for performing such assays applying techniques and principles known in the art with routine experimentation.

Other methods useful for diagnosing cancer progression include tumor grading and staging methods, such as the American Joint Commission on Cancer grading system, the National Program of Cancer Registries "General Staging" method (also known as Summary Staging, California Staging, and SEER Staging), and/or commonly used specialized grading systems (e.g., a high Gleason tumor grade score is indicative of an aggressive cancer in the context of prostate cancer; a TNM (Tumor, Nodes, Metastasis) Staging System often is useful in the context of colorectal cancer, and the Scarff-Bloom-Richardson system often is used in the context of breast cancer assessments) (see, e.g., Fawcett and Drew, Prof Nurse. 2002 April; 17(8):470-2; Toloza et al., Chest. 2003 January; 123(1 Suppl):157S-166S; Fischer et al., Lancet Oncol. 2001 November; 2(11):659-66; and Perrotti et al., Urology. 1999 August; 54(2):208-14; Zinkin, Dis Colon Rectum. 1983 January; 26(1):37-43; see also generally Neal, Clinical Oncology (Oxford University Press—$3^{rd}$ Ed. 2003), Price, Treatment of Cancer (Oxford University Press—$4^{th}$ Ed. 2002), Franks, Introduction to the Cellular and Molecular Biology of Cancer (Oxford University Press—$3^{rd}$ Ed. 1997); Bast et al., Cancer Medicine, 5th Edition (BC Decker Inc.—2000); Adami, Textbook of Cancer Epidemiology (Oxford University Press 2002). Further methods for identifying cancer and/or diagnosing cancer progression include cancer gene-related DNA methylation (see, e.g., Carmen et al., J. Natl. Cancer Inst., 93(22) (2001)), DNA cytometry, mitosis assays (as to frequency, normalcy, or both), pleomorphism evaluations, the presence of autocrine stimulatory loop activity, tubule formation measurements, keritinization assays, intercellular bridge formation assays, epithelial pearl detection, aberrant hormone receptor expression or form production assays (e.g., Her2 overexpression assays), and other cancer-associated gene expression assays (e.g., PRL-3 protein tyrosine phosphatase gene expression assays). Additionally useful diagnostic methods are described in U.S. Pat. No. 6,682,901 and PCT Publication WO 03/033667. The inventive therapeutic regimens of the invention (involving, among other things, the delivery of an Anti-KIR antibody or related compound to a patient in need thereof so as to reduce cancer progression in one or more aspects thereof) can be practiced in association with finding an indication of cancer and/or cancer progression in a patient as determined by any one of these or other diagnostic assays described herein or their equivalents. Such methods are additional features of this invention.

The methods of the invention can be used to reduce the cancer progression of any suitable type of cancer. Forms of cancer that may be treated by the delivery or administration of Anti-KIR antibodies, Anti-KIR antibody compositions, and combination compositions provided by the invention include squamous cell carcinoma, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, Burketts lymphoma, acute or chronic myelogenous leukemias, promyelocytic leukemia, fibrosarcoma, rhabdomyoscarcoma; melanoma, seminoma, teratocarcinoma, neuroblastoma, glioma, astrocytoma, neuroblastoma, glioma, schwannomas; fibrosarcoma, rhabdomyoscaroma, osteosarcoma, melanoma, xeroderma pigmentosum, keratoacanthoma, seminoma, thyroid follicular cancer, and teratocarcinoma. Anti-KIR antibodies also can be useful in the treatment of other carcinomas of the bladder, breast, colon, kidney, liver, lung, ovary, prostate, pancreas, stomach, cervix, thyroid or skin. Anti-KIR antibodies also may be useful in treatment of other hematopoietic tumors of lymphoid lineage, other hematopoietic tumors of myeloid lineage, other tumors of mesenchymal origin, other tumors of the central or peripheral nervous system, and/or other tumors of mesenchymal origin.

In a particular aspect, Anti-KIR antibodies are administered to reduce cancer progression in or associated with a hematopoietic tumor of lymphoid lineage. In more particular aspects, Anti-KIR antibodies are administered to reduce cancer progression in a tumor selected from T-prolymphocytic leukemia (T-PLL) (including small cell and/or cerebriform cell types thereof); large granular lymphocyte leukemia (LGL) of the T-cell type; Sezary syndrome (SS); adult T-cell leukemia lymphoma (ATLL); a/d T-NHL hepatosplenic lymphoma; peripheral/post-thymic T cell lymphoma of the pleomorphic or immunoblastic subtype; angio immunoblastic T-cell lymphoma; angiocentric (nasal) T-cell lymphoma; anaplastic (Ki 1+) large cell lymphoma; intestinal T-cell lymphoma; T-lymphoblastic leukemia; and/or lymphoma/leukemia (T-Lbly/T-ALL).

Advantageously, the methods of the invention also may be useful in reducing cancer progression in prostate cancer cells, melanoma cells (e.g., cutaneous melanoma cells, ocular melanoma cells, and/or lymph node-associated melanoma cells), breast cancer cells, colon cancer cells, and lung cancer cells. The methods of the invention can be used to reduce cancer progression in both tumorigenic and non-tumorigenic cancers (e.g., non-tumor-forming hematopoietic cancers). The methods of the invention are particularly useful in the treatment of epithelial cancers (e.g., carcinomas) and/or colorectal cancers, breast cancers, lung cancers, vaginal cancers, cervical cancers, and/or squamous cell carcinomas (e.g., of the head and neck). Additional potential targets include sarcomas and lymphomas. Additional advantageous targets include solid tumors and/or disseminated tumors (e.g., myeloid and lymphoid tumors, which can be acute or chronic).

In another aspect, the invention provides a method of reducing the risk of cancer progression, reducing the risk of further cancer progression in a cell population that has undergone initiation, and/or providing a therapeutic regimen for reducing cancer progression in a human patient, which comprises administered an amount of an Anti-KIR antibody, a related compound, or combination composition (or applying a combination administration method) to a patient that has been diagnosed as having cells exhibiting preneoplastic and/or neoplastic cell-like levels and/or types of gene expression, such as cancer-associated patterns of erbB2 (Her2/neu) gene expression; p53 gene expression; BRCA1 and/or BRCA2 gene expression; PTEN gene expression; ras family gene expression (k-ras, h-ras, m-ras, RAB2. RAP2A, etc.), c-MYC gene expression or cancer-like expression of one or more of the following Exol, ASPP2, C/EBPD, p16(INK4a) CDKN2A, R24P, P81L, V126D, BNIP3, MYH, PTCH, B-ras, A-ras, PPAR ($\alpha$, $\gamma$, and $\Delta$), MC1R, TP16p14/ARF, SMAD3, SMAD4, CDK4, p73, p15, AXIN1, raf, CHEK2, SHIP, HFE, p21(CIP1/WAF1), FAS, TSG101, MEN1, GSTPI, P2X7, BRAF, HPV type 16 E7, P27 Cyclin E. Cyclin D, Rb, P300, Mdm2, Fos, Jun, N-Ras, Ki-Ras, Raf-1, Abl, Bcl-2, Bcl-6, Bax, APC (Accession No: M74088), Beta catenin, E-cadherin, PI3-kinase, TGF$\alpha$, TGF$\beta$, TGF$\beta$ receptor, Src, Met, Akt, Alk, Grb2, Shc, and E2F 1-5. In a particular exemplary aspect, the invention provides a method of inhibiting cancer progression (either before or after detection of any aspect thereof) in a human exhibiting cancer-like upregulation/expression of Ras and Myc; expression of Ras with loss of regular p53 gene activity; expression of Ras with loss of regular Rb activity; expression of Ras with loss of regular NFK$\beta$ activity; Expression of Ras with loss of regular APC activity; expression of Ras with loss of regular Arf activity; expression of Ras with E7; etc.

In another exemplary aspect, the invention provides a method of increasing the ratio of quiescent to invasive neoplastic cells in a mammalian host comprising administering a therapeutically effective amount of an Anti-KIR antibody (e.g., an Anti-KIR antibody), related composition, or combination composition of the invention so as to increase the ratio of quiescent to invasive cells in the host.

In a further aspect, the invention provides a method of promoting remission of a cancer in a mammalian host, such as a human patient, comprising administering a composition comprising an Anti-KIR antibody, such as an Anti-KIR antibody that competes with mAb DF200 (relatively inhibits at a level of at least about 10% by ELISA assay, such as about 15% or more, 20% or more, 25% or more, etc.), to the host, so as to promote cancer remission in the host.

In an even further aspect, the invention provides a method for reducing the risk of developing a cancerous condition, reducing the time to onset of a cancerous condition, reducing the severity of a cancer diagnosed in the early stages, and/or reducing the affected area of a cancer upon development thereof in a mammalian host, comprising administering to a host a prophylactically effective amount of an Anti-KIR antibody, related compound, or combination composition of the invention so as to achieve the desired physiological effect(s).

In another aspect, the present invention provides methods for inhibiting tumor growth and/or metastasis in an individual in need thereof, comprising contacting the tumor with an amount of an Anti-KIR antibody, related composition, or combination composition of the invention, so as to inhibit tumor growth and/or metastasis. Target tumors can include, but are not limited to, carcinomas. Such carcinomas include, but are not limited to squamous cell carcinomas (including but not limited to squamous cell carcinoma of skin, cervix, and vulva), gastric carcinomas, colon adenocarcinomas, colorectal carcinomas, and cervical carcinomas. Other carcinomas that can be treated by inventive methods described herein include ductal mammary carcinomas. Other common cancers that can be treated by inventive methods described herein include malignant melanomas.

Inhibiting tumor growth generally means causing a reduction in the amount of tumor growth that would occur in the absence of treatment and/or substantially complete cessation of detectable tumor growth, and includes decreases in tumor size and/or decrease in the rate of tumor growth. Inhibiting metastases means to reduce the amount of tumor metastasis that would occur in the absence of treatment, and includes a relative decrease in the number and/or size of metastases.

In still a different aspect, the inventive methods can provide means for eliciting, promoting, and/or enhancing an anti-tumor effect by slowing the growth, spread, or growth and spread of the front of a tumor into surrounding tissues, or the expected growth, spread, or growth and spread of a tumor. Tumor cell growth inhibition can be measured by any suitable standard and technique using, e.g., other methods described herein and/or inhibition assays such as are described in WO 89/06692.

An additional aspect of the invention is to provide a method for inhibiting or slowing the growth and/or spreading of a tumor into surrounding tissue by delivering to a patient in need thereof. Anti-KIR antibody antibody or other effective Anti-KIR antibody, related compound, or combination composition.

The inventive methods also can be particularly advantageous with respect to the elimination of micrometastases and/or for the prevention of a recurrence of cancer in a patient previously diagnosed with cancer but currently in a state of remission. Methods for assessing recurrence and/or the risk of recurrence are known in the art (see, e.g., U.S. Pat. No. 6,656,684) and can include application of other cancer diagnostic methods described herein.

In a further aspect, the invention provides a method of increasing the likelihood of survival over a relevant period in a human patient diagnosed with cancer. For example, the invention provides a method of increasing the likelihood of survival about six months, about nine months, about one year, about three years, or longer after treatment with an Anti-KIR antibody composition of the invention, as compared to not receiving treatment with the Anti-KIR antibody composition (survival rates can be determined by, e.g., studies on a population of similar patients, such as in the context of a clinical trial).

In another aspect, the invention provides a method for improving the quality of life of a cancer patient comprising administering to the patient a composition of the invention in an amount effective to improve the quality of life thereof. Methods for assessing patient quality of life in cancer treatment are well known in the art (see, e.g., Movass and Scott, Hematol Oncol Clin North Am. 2004 February; 18(1):161-86; Dunn et al., Aust N Z J Public Health. 2003; 27(1):41-53; Morton and Izzard, World J Surg. 2003 July; 27(7):884-9; Okamato et al., Breast Cancer. 2003; 10(3): 204-13; Conroy et al., Expert Rev Anticancer Ther. 2003 August; 3(4):493-504; List et al., Cancer Treat Res. 2003; 114:331-51; and Shimozuma et al., Breast Cancer. 2002; 9(3):196-202).

In a further aspect, inventive methods described herein can be applied to significantly reduce the number of cancer cells in a vertebrate host, such that, for example, the total number and/or size of tumors are reduced. Such methods can be applied to treat any suitable type of tumor including chemoresistant tumors, solid tumors, and/or metastasized tumors. In a related sense, the invention provides a method for killing preneoplastic and/or neoplastic cells in a vertebrate, such as a human cancer patient.

Viral Infections

In another aspect, the invention provides a method of treating a viral infection in a patient or host that comprises administering or otherwise delivering a therapeutically effective amount of an Anti-KIR antibody or combination composition so as to reduce the severity, spread, symptoms, or duration of such infection. For example, such a method can be used to treat infection by one or more viruses selected from hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus (CMV—e.g., HCMV), echinovirus, arbovirus, huntavirus, coxsackie virus, mumps virus, measles virus, rubella virus, polio virus, and/or human immunodeficiency virus type 1 or type 2 (HIV-1, HIV-2). The practice of such methods may result in a reduction in the titer of virus (viral load), reduction of the number of virally infected cells, etc. In a particular aspect, these methods are practiced in immunocompromised/immunosuppressed individuals. In another aspect, these methods are practiced in patients at relatively higher risk of immunosuppression or having a relatively defective immune system, such as in young children (e.g., children of about 10 years or less, about 8 years or less, about 6 years or less, about 5 years or less, about 4 years or less, about 3 years or less, about 2 years or less in age, about 1-18 months, about 1-12 months, about 1-9 months, about 1-6 months, or less than about 3 months in age) or the elderly (e.g., patients of about 65 years or more, about 70 years or more, about 75 years or more, about 80 years or more, about 85 years or more in age, etc.). In other inventive methods (e.g., the treatment of cancer) the inventive method can be similarly limited to population groups wherein general effectiveness is expected to be improved. As discussed elsewhere herein, in certain contexts, specificity of an Anti-KIR antibody can lead to definition of significant population groups, such as Caucasians that generally possess a type A haplotype, for example wherein the Anti-KIR antibody is cross-reactive for KIRs relevant to such a population.

Anti-KIR antibodies can be administered with or in association with anti-viral agents, such as protease inhibitor (e.g. acyclovir) in the context of HIV treatment or an anti-viral anti-body (e.g., an anti-gp41 and anti CD4 antibody in the context of HIV treatment, etc.). Numerous types of anti-viral agents are known with respect to each type of target virus. In one aspect, present invention provides a method of treating a viral disease comprising administering to a patient in need thereof a therapeutically efficient amount of a further anti-viral agent. Examples of such agents are:

Against Herpes simplex, varicella zoster virus (VSV) infection: Aciclovir, famciclovir, valaciclovir, penciclovir.

Against CMV infection: Ganciclovir, valganciclovir.

Against retrovirus infection (e.g HIV-1): Lamivudin, zidovudin, emtricitabin, abacavir, tenofovir, didanosin, stavudin, efavirenz, nevirapin, amprenavir, indinavir, saquinavir, ritonavir, lopinavir, atazanavir, nelfinavir, enfuvirtid.

Against influenza virus infection: Oseltamivir.

Against chronic hepatitis B virus infection: Adefovir, lamivudin

Against chronic hepatitis C virus infection: Ribavirin, interferon-alpha, pegylated interferon alpha.

Anti-KIR antibodies for use against viruses can be selected on any suitable basis, such as, for example, the ability to reduce the number of virus-infected cells in a host.

EXAMPLE 1

In vitro correlation of enhanced NK cell activity as a result of combination therapy with anti-KIR antibodies and recombinant interferon alpha/beta.

Human NK cells (freshly isolated or precultivated in vitro with interleukin-2 for 2-14 days) are mixed with chromium labelled target cells (e.g. K562, or EBV transformed B-cells) in a standard 4 hour cytotoxicity assay in the presence of one or more anti-KIR antibodies and interferon alpha or beta. It is expected that the combination results in enhanced specific lysis as compared to 'monotherapy' with either KIR antibodies or interferon alpha/beta alone.

EXAMPLE 2

As discussed above, MHC class I specific, inhibitory NK receptors include KIR in humans (see, e.g., A. Moretta et al., *J Exp Med* 178, 597-604 (1993); N. Wagtmann et al., *Immunity* 2, 439-449 (1995); M. Colonna and J. Samaridis, *Science* 268, 405-408 (1995); and V. Litwin, J. Gumperz, P. Parham, J. H. Phillips, L. L. Lanier, *J Exp Med* 180, 537-543 (1994)), Ly49 in rodents (see, e.g., F. M. Karlhofer, R. K. Ribaudo, W. M. Yokoyama, *Nature* 358, 66-70 (1992)), and the conserved CD94/NKG2A receptors in both species (V. M. Braud et al., *Nature* 391, 795-799 (1998)). Upon engagement of MHC class I molecules, these receptors transmit negative signals that inhibit NK cell-mediated lysis (see, e.g., Karlhofer et al. (1992), supra, Braud et al. (1998), supra, and N. Wagtmann, S. Rajagopalan, C. C. Winter, M. Peruzzi, E. O. Long, *Immunity* 3, 801-809 (1995)).

To test the effects of combination treatments as cancer therapy based on mAb-mediated blocking of inhibitory receptors (IR) together with other anti-cancer agents a mouse model was used in which the NK CIR antibody was represented by 5E6 antibody directed against Ly49I/C (see C. Y. Koh et al., *Blood* 97, 3132-3137 (2001)). The 5E6 antibody functions in an analogous fashion to anti-KIR mAbs (due to the similarity between the Ly49 and KIR receptors). In the mouse tumor model, the anti-IR mAb was used in combination with cytokines that stimulate NK cell proliferation or activation, such as IL-2 (as described in this Example) and IL-21 (as described in Example 3).

C57BL/6 inbred mice were inoculated subcutaneously with B16.F10 murine melanoma cells, and the tumor size was measured at least twice weekly with a digital caliper. Therapeutic treatment was initiated 3 days after tumor cell inoculation. At that time solid tumors were recognizable. The mice were randomized into 4 groups (n=8), receiving either A) no treatment, B) a weekly administration of anti-Ly49I/C mAb (Fab'2), C) a three-day cycle of systemic human IL-2 administration repeated each week, or D) a combination of anti-Ly49I/C and IL-2 administration in the same schedule as above.

As can be seen in FIG. 1, anti-Ly49 alone, showed no effect on growth of B16 tumors in this setting, whereas IL-2 alone, in the doses applied here, had a slight anti-tumor effect, which was not statistically significant. However, when the combination of anti-Ly49I/C mAb and IL-2 was given a strong anti-tumor effect was observed, with highly statistically significant reduction (p>0.002) in tumor burden compared to both the untreated and the anti-Ly49 treated groups, and with significant reduction (p>0.05) in tumor burden compared to the group treated with IL-2 alone (two-tailed T-test with equal variance).

These results indicate that anti-Ly49I/C mAb unexpectedly synergizes with IL-2 in promoting immune-mediated tumor clearance. As indicated above, a similar synergy is expected (based on the relationship of such NK cell receptors) for combinations of anti-KIR antibodies and IL-2 proteins, including IL-2 variants and derivatives having biological activity similar to IL-2, in human patients.

EXAMPLE 3

A 3-hr lung clearance assay, generally based upon the method described in Jia et al., *J. Immunol.*, 165(11):6142-7 (2000), was used to demonstrate that the combination of murine interleukin-21 (mIL-21) and anti-Ly49I/C antibodies (as noted above, these are antibodies against murine counterparts of human KIR) significantly augments lung clearance of B16F10 melanoma and RMA lymphoma compared to either agent administered alone. Specifically, mIL-21 and an antibody fragment having known anti-tumor effects given alone and in combination were tested in the two different well-known syngeneic tumour models, B16F10 melanoma and RMA lymphoma. 5E6 is a monoclonal F(ab)$_2$ fragment against Ly49C and Ly49I inhibitory receptors on NK cells (mouse counterparts of human KIR) (see, e.g., Koh et al., Biol Blood Marrow Transplant. 2002; 8(1):17-25 and Koh et al., Blood, 97(10):3132-3137 (2001)).

Figure 2:
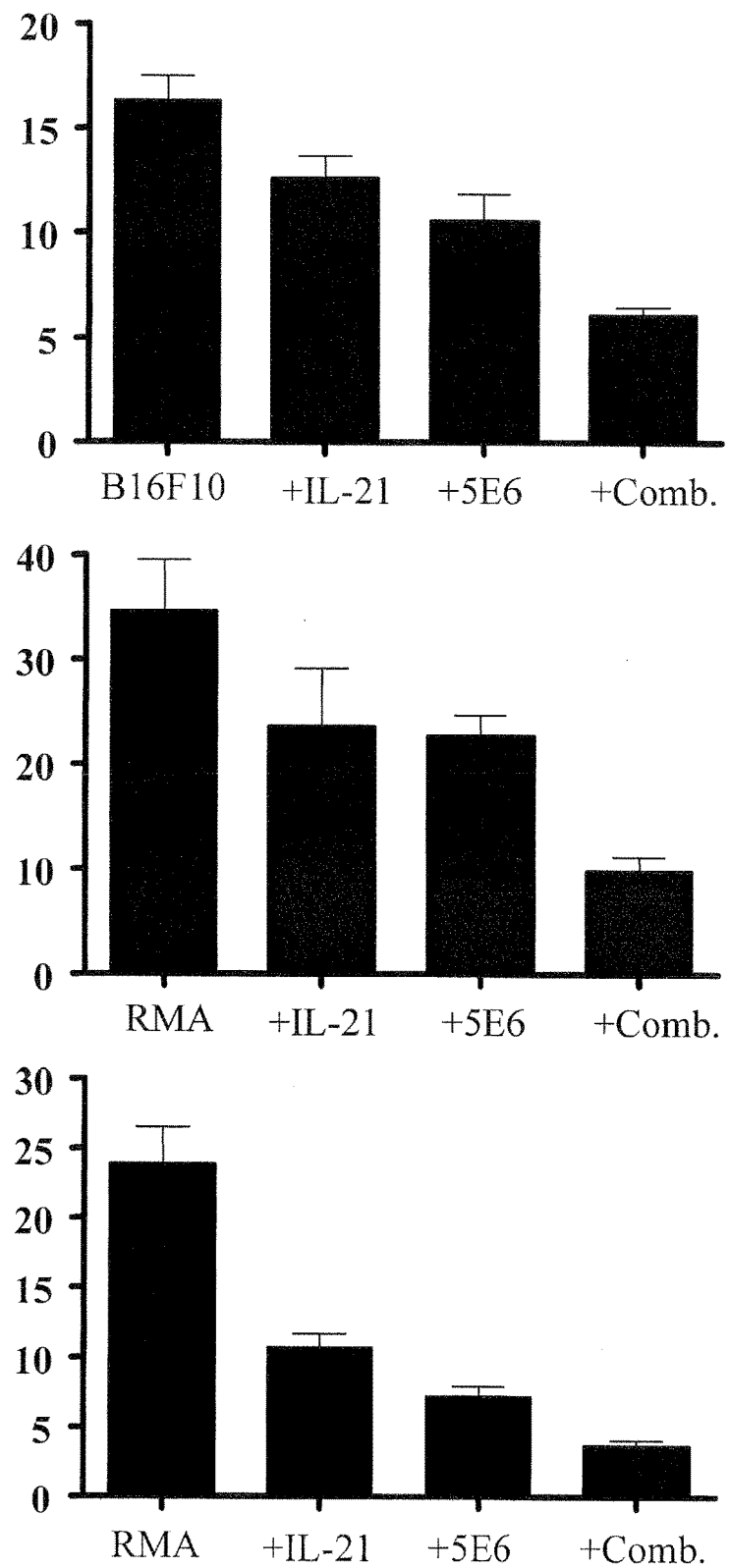
FIG. 2 shows the results of experiments performed in two mouse tumor models when the mice were treated with anti-Ly49 antibody, IL-21, or both.

Particularly, $^{51}$Cr-labelled RMA or B16F10 tumour cells were i.v. injected ($5\times10^5$ cells) into syngeneic C57BL/6 mice. The retention of radioactivity in the lungs was scored after 3 hours. IL-21 treated mice were injected s.c. with a dose of 50 µg day −3, −2, and −1 before tumour cell injection. 5E6 treated mice were injected i.v. with a dose 50 µg (upper and middle panel) or 25 µg (lower panel) day −1 before tumour cell injection. The results are expressed as percentage of the total radioactivity inoculated. Mean±SEM, t-test. The results of these experiments are presented in FIG. 2 (the vertical axis represents the percentage of radioactivity retained in the lungs relative to the control).

These data demonstrate that both mIL-21 cytokine therapy and blockade of Ly49C/I receptors on NK cells augment the anti-tumour activity in the lung. The difference in the treatment with either compound was significantly different from the control and the treatment for the combination with significantly different from either agent taken alone in the lung (measurements in the liver and spleen did not show such differences, possibly due to, e.g., insufficient numbers of cells in the case of the spleen and possible mixture of cells and cell fragments contained in the liver). However, a further anti-tumour activity was found in the groups treated with both compounds, suggesting that the combination of IL-21 and anti-KIR might produce a stronger anti-tumour response than either agent given alone.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

SEQUENCE LISTING

```
<160> NUMBER OF SEQ ID NOS: 43

<210> SEQ ID NO 1
<211> LENGTH: 128
<212> TYPE: PRT
<213> ORGANISM: Mus musculus

<400> SEQUENCE: 1

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys Arg
        115                 120                 125

<210> SEQ ID NO 2
<211> LENGTH: 131
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ser
            20                  25                  30

Met Ser Ala Ser Leu Gly Glu Arg Val Thr Met Thr Cys Thr Ala Ser
        35                  40                  45

Ser Ser Val Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125
```

Ile Lys Arg
    130

<210> SEQ ID NO 3
<211> LENGTH: 11
<212> TYPE: PRT
<213> ORGANISM: Mus musculus

<400> SEQUENCE: 3

Lys Ala Ser Glu Asn Val Val Thr Tyr Val Ser
1               5                   10

<210> SEQ ID NO 4
<211> LENGTH: 12
<212> TYPE: PRT
<213> ORGANISM: Mus musculus

<400> SEQUENCE: 4

Thr Ala Ser Ser Ser Val Ser Ser Ser Tyr Leu Tyr
1               5                   10

<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5

<210> SEQ ID NO 6
<211> LENGTH: 7
<212> TYPE: PRT
<213> ORGANISM: Mus musculus

<400> SEQUENCE: 6

Ser Thr Ser Asn Leu Ala Ser
1               5

<210> SEQ ID NO 7
<211> LENGTH: 9
<212> TYPE: PRT
<213> ORGANISM: Mus musculus

<400> SEQUENCE: 7

Gly Gln Gly Tyr Ser Tyr Pro Tyr Thr
1               5

<210> SEQ ID NO 8
<211> LENGTH: 9
<212> TYPE: PRT
<213> ORGANISM: Mus musculus

<400> SEQUENCE: 8

His Gln Tyr His Arg Ser Pro Pro Thr
1               5

<210> SEQ ID NO 9
<211> LENGTH: 140
<212> TYPE: PRT
<213> ORGANISM: Mus musculus

<400> SEQUENCE: 9

Met Ala Val Leu Gly Leu Leu Phe Cys Leu Val Thr Phe Pro Ser Cys

```
                1               5                  10                 15
            Val Leu Ser Gln Val Gln Leu Glu Gln Ser Gly Pro Gly Leu Val Gln
                        20                  25                 30

Pro Ser Gln Ser Leu Ser Ile Thr Cys Thr Val Ser Gly Phe Ser Phe
                        35                  40                 45

Thr Pro Tyr Gly Val His Trp Val Arg Gln Ser Pro Gly Lys Gly Leu
                        50                  55                 60

Glu Trp Leu Gly Val Ile Trp Ser Gly Gly Asn Thr Asp Tyr Asn Ala
             65                  70                  75                 80

Ala Phe Ile Ser Arg Leu Ser Ile Asn Lys Asp Asn Ser Lys Ser Gln
                        85                  90                 95

Val Phe Phe Lys Met Asn Ser Leu Gln Val Asn Asp Thr Ala Ile Tyr
                        100                 105                110

Tyr Cys Ala Arg Asn Pro Arg Pro Gly Asn Tyr Pro Tyr Gly Met Asp
                        115                 120                125

Tyr Trp Gly Gln Gly Thr Ser Val Thr Val Ser Ser
                        130                 135                140

<210> SEQ ID NO 10
<211> LENGTH: 10
<212> TYPE: PRT
<213> ORGANISM: Mus musculus

<400> SEQUENCE: 10

Gly Phe Ser Phe Thr Pro Tyr Gly Val His
1               5                   10

<210> SEQ ID NO 11
<211> LENGTH: 16
<212> TYPE: PRT
<213> ORGANISM: Mus musculus

<400> SEQUENCE: 11

Val Ile Trp Ser Gly Gly Asn Thr Asp Tyr Asn Ala Ala Phe Ile Ser
1               5                   10                  15

<210> SEQ ID NO 12
<211> LENGTH: 13
<212> TYPE: PRT
<213> ORGANISM: Mus musculus

<400> SEQUENCE: 12

Asn Pro Arg Pro Gly Asn Tyr Pro Tyr Gly Met Asp Tyr
1               5                   10

<210> SEQ ID NO 13
<211> LENGTH: 109
<212> TYPE: PRT
<213> ORGANISM: Homo sapiens

<400> SEQUENCE: 13

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Met Tyr
                 85                  90                  95

Thr Phe Gly Gln Gly Thr Lys Leu Glu Ile Lys Arg Thr
            100                 105

<210> SEQ ID NO 14
<211> LENGTH: 327
<212> TYPE: DNA
<213> ORGANISM: Homo sapiens

<400> SEQUENCE: 14
gaaattgtgt tgacacagtc tccagtcacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ttgtcagcag cgtagcaact ggatgtacac ttttggccag    300
gggaccaagc tggagatcaa acgaact                                        327

<210> SEQ ID NO 15
<211> LENGTH: 123
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Phe Tyr
                 20                  25                  30

Ala Ile Ser Trp Val Arg Gln Ala Pro Gly Gln Gly Leu Glu Trp Met
             35                  40                  45

Gly Gly Phe Ile Pro Ile Phe Gly Ala Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
            115                 120

<210> SEQ ID NO 16
<211> LENGTH: 369
<212> TYPE: DNA
<213> ORGANISM: Homo sapiens

<400> SEQUENCE: 16
caggtccagc tggtgcagtc tggggctgag gtgaagaagc ctgggtcctc ggtgaaggtc     60
tcctgcaagg cttctggagg caccttcagt ttctatgcta tcagctgggt gcgacaggcc    120
cctggacaag gcttgagtg gatgggaggg ttcatcccta tctttggtgc agcaaactac    180
gcacagaagt tccagggcag agtcacgatt accgcggacg aatccacgag cacagcctac    240
atggaactga gcagcctgag atctgacgac acggccgtgt attactgtgc gagaatccct    300
```

-continued

```
agtgggagct actactacga ctacgatatg gacgtctggg gccaagggac cacggtcacc    360
gtctcctca                                                            369
```

<210> SEQ ID NO 17
<211> LENGTH: 91
<212> TYPE: PRT
<213> ORGANISM: Mus musculus

<400> SEQUENCE: 17

```
Gln Phe Ile Ile Leu Ala Gly Asn Ile Val Leu Thr Gln Ser Pro Ser
1               5                   10                  15

Met Ser Ser Leu Gly Glu Arg Val Thr Leu Thr Cys Ala Ser Val Ser
            20                  25                  30

Tyr Leu Trp Tyr Gln Gln Lys Pro Ser Pro Lys Leu Ile Tyr Ser Asn
        35                  40                  45

Ser Gly Val Pro Arg Phe Ser Gly Ser Gly Ser Ala Thr Phe Ser Leu
    50                  55                  60

Thr Ile Ser Ser Met Ala Glu Asp Ala Tyr His Cys Gln His Pro Thr
65                  70                  75                  80

Phe Gly Gly Gly Thr Lys Leu Glu Ile Lys Arg
                85                  90
```

<210> SEQ ID NO 18
<211> LENGTH: 6
<212> TYPE: PRT
<213> ORGANISM: Mus musculus

<400> SEQUENCE: 18

```
Ala Ser Val Ser Tyr Leu
1               5
```

<210> SEQ ID NO 19
<211> LENGTH: 4
<212> TYPE: PRT
<213> ORGANISM: Mus musculus

<400> SEQUENCE: 19

```
Ser Asn Ser Ser
1
```

<210> SEQ ID NO 20
<211> LENGTH: 4
<212> TYPE: PRT
<213> ORGANISM: Mus musculus

<400> SEQUENCE: 20

```
Gln His Pro Thr
1
```

<210> SEQ ID NO 21
<211> LENGTH: 11
<212> TYPE: PRT
<213> ORGANISM: Artificial sequence
<220> FEATURE:
<223> OTHER INFORMATION: CDR-L1

<400> SEQUENCE: 21

```
Lys Ala Ser Gln Asn Val Val Thr Tyr Val Ser
1               5                   10
```

<210> SEQ ID NO 22
<211> LENGTH: 9

```
<212> TYPE: PRT
<213> ORGANISM: Artificial sequence
<220> FEATURE:
<223> OTHER INFORMATION: CDR-L3

<400> SEQUENCE: 22

Gly Gln Gly Tyr Ser Tyr Phe Tyr Thr
1               5

<210> SEQ ID NO 23
<211> LENGTH: 10
<212> TYPE: PRT
<213> ORGANISM: Artificial sequence
<220> FEATURE:
<223> OTHER INFORMATION: CDR-H1

<400> SEQUENCE: 23

Gly Phe Ser Phe Thr Phe Tyr Gly Val His
1               5                   10

<210> SEQ ID NO 24
<211> LENGTH: 10
<212> TYPE: PRT
<213> ORGANISM: Artificial sequence
<220> FEATURE:
<223> OTHER INFORMATION: CDR-H1

<400> SEQUENCE: 24

Gly Tyr Thr Phe Thr Ser Tyr Trp Met His
1               5                   10

<210> SEQ ID NO 25
<211> LENGTH: 17
<212> TYPE: PRT
<213> ORGANISM: Artificial sequence
<220> FEATURE:
<223> OTHER INFORMATION: CDR-H2

<400> SEQUENCE: 25

Thr Ile Tyr Pro Gly Asn Ser Asp Thr Asn Tyr Asn Gln Lys Phe Lys
1               5                   10                  15

Gly

<210> SEQ ID NO 26
<211> LENGTH: 12
<212> TYPE: PRT
<213> ORGANISM: Artificial sequence
<220> FEATURE:
<223> OTHER INFORMATION: CDR-H3

<400> SEQUENCE: 26

Pro Thr Thr Ala Thr Arg Ser Ser Ala Met Asp Tyr
1               5                   10

<210> SEQ ID NO 27
<211> LENGTH: 127
<212> TYPE: PRT
<213> ORGANISM: Artificial sequence
<220> FEATURE:
<223> OTHER INFORMATION: variable light sequence

<400> SEQUENCE: 27

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
                20                  25                  30
```

```
Met Ser Val Gly Glu Arg Val Thr Leu Thr Cys Lys Asn Ser Glu Asn
            35                  40                  45

Val Val Thr Tyr Val Ser Trp Tyr Gln Gln Lys Pro Glu Gln Ser Pro
 50                  55                  60

Lys Leu Leu Ile Tyr Gly Ala Ser Asn Arg Tyr Thr Gly Val Pro Asp
 65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
                100                 105                 110

Ser Tyr Pro Tyr Thr Phe Gly Gly Thr Lys Leu Asp Ile Lys Arg
            115                 120                 125

<210> SEQ ID NO 28
<211> LENGTH: 131
<212> TYPE: PRT
<213> ORGANISM: Artificial sequence
<220> FEATURE:
<223> OTHER INFORMATION: variable light sequence

<400> SEQUENCE: 28

Met Asp Phe Gln Val Gln Ile Phe Ser Phe Leu Leu Ile Ser Ala Ser
 1               5                  10                  15

Val Ile Met Ser Arg Gly Gln Ile Val Leu Thr Gln Ser Pro Ala Ser
                20                  25                  30

Met Ser Ala Ser Leu Gly Glu Arg Val Thr Met Thr Cys Thr Ala Ser
            35                  40                  45

Ser Ser Val Ser Ser Ser Tyr Leu Tyr Trp Tyr Gln Gln Lys Pro Gly
 50                  55                  60

Ser Ser Pro Lys Leu Trp Ile Tyr Ser Thr Asn Leu Ala Ser Gly
 65                  70                  75                  80

Val Pro Ala Arg Phe Ser Gly Ser Gly Ser Gly Thr Ser Tyr Ser Leu
                85                  90                  95

Thr Ile Ser Ser Met Gln Ala Glu Asp Ala Ala Thr Tyr Tyr Cys His
                100                 105                 110

Gln Tyr His Arg Ser Pro Pro Thr Phe Gly Gly Gly Thr Lys Leu Glu
            115                 120                 125

Ile Lys Arg
    130

<210> SEQ ID NO 29
<211> LENGTH: 140
<212> TYPE: PRT
<213> ORGANISM: Artificial sequence
<220> FEATURE:
<223> OTHER INFORMATION: variable heavy sequence

<400> SEQUENCE: 29

Met Glu Cys Asn Trp Ile Leu Pro Phe Ile Leu Ser Val Thr Ser Gly
 1               5                  10                  15

Val Tyr Ser Glu Val Gln Leu Gln Gln Ser Gly Thr Val Leu Ala Arg
                20                  25                  30

Pro Gly Ala Ser Val Lys Met Ser Cys Lys Ala Ser Gly Tyr Thr Phe
            35                  40                  45

Thr Ser Tyr Trp Met His Trp Met Lys Gln Arg Pro Gly Gln Gly Leu
 50                  55                  60

Glu Trp Ile Gly Thr Ile Tyr Pro Gly Asn Ser Asp Thr Asn Tyr Asn
```

```
                65                  70                  75                  80
Gln Lys Phe Lys Gly Lys Ala Lys Leu Thr Ala Val Thr Ser Thr Asn
                    85                  90                  95
Thr Ala Tyr Met Glu Leu Ser Ser Leu Thr Asn Glu Asp Ser Ala Val
                    100                 105                 110
Tyr Tyr Cys Ser Arg Pro Thr Thr Ala Thr Arg Ser Ser Ala Met Asp
            115                 120                 125
Tyr Trp Gly Gln Gly Thr Ser Val Thr Val Ser Ser
            130                 135                 140

<210> SEQ ID NO 30
<211> LENGTH: 12
<212> TYPE: PRT
<213> ORGANISM: Artificial sequence
<220> FEATURE:
<223> OTHER INFORMATION: CDR-L1
<220> FEATURE:
<221> NAME/KEY: MISC_FEATURE
<223> OTHER INFORMATION: Xaa1 is Lys or Thr; Xaa4 is Glu or Ser; Xaa5 is
      Asn or Ser; Xaa7 is Val or Ser; Xaa9 is Ser or is absent; and
      Xaa12 is Ser or Tyr (Formula Ia)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 30

Xaa Ala Ser Xaa Xaa Val Xaa Ser Xaa Tyr Leu Xaa
1               5                   10

<210> SEQ ID NO 31
<211> LENGTH: 12
<212> TYPE: PRT
<213> ORGANISM: Artificial sequence
<220> FEATURE:
<223> OTHER INFORMATION: CDR-L1
<220> FEATURE:
<221> NAME/KEY: MISC_FEATURE
<223> OTHER INFORMATION: Xaa1 is Lys or Thr; Xaa4 is Glu or Ser; Xaa5 is
      Asn or Ser; Xaa7 is Val or Ser; and Xaa12 is Ser or Tyr
<220> FEATURE:
<221> NAME/KEY: MISC_FEATURE
<223> OTHER INFORMATION: Xaa8 and Xaa11 are any suitable amino acid
      residue, Xaa8 is Thr or Ser, Xaa11 is Val or Leu, or Xaa8 is Thr
      or Ser and Xaa11 is Val or Leu
<220> FEATURE:
<221> NAME/KEY: MISC_FEATURE
<223> OTHER INFORMATION: Xaa9 is Ser, absent, or any suitable amino acid
      residue other than Ser (e.g., Gly)
<220> FEATURE:
<221> NAME/KEY: MISC_FEATURE
<223> OTHER INFORMATION: Xaa2 Xaa3 Xaa6 Xaa10 and Xaa11 are each defined
      by the corresponding positions in Formula I (e.g., Xaa2 is Ala),
      optionally except for one or more of the following: Xaa2 is any
      suitable residue other than Ala; Xaa3 is any suitable residue
      other than Ser; Xaa6 is any suitable residue other than Val; Xaa10
``` is any suitable residue other than Tyr; and Xaa11 is any suitable
    residue other than Leu (Formula II)
<220> FEATURE:
<221> NAME/KEY: misc_feature
<222> LOCATION: (1)..(12)
<223> OTHER INFORMATION: Xaa can be any naturally occurring amino acid

<400> SEQUENCE: 31

Xaa Xaa Xaa Xaa Xaa Xaa Xaa Xaa Xaa Xaa Xaa Xaa
1               5                   10

<210> SEQ ID NO 32
<211> LENGTH: 7
<212> TYPE: PRT
<213> ORGANISM: Artificial sequence
<220> FEATURE:
<223> OTHER INFORMATION: CDR-L2
<220> FEATURE:
<221> NAME/KEY: MISC_FEATURE
<223> OTHER INFORMATION: Xaa1 is Gly or Ser; Xaa2 is Ala or Thr; Xaa5 is
      Arg or Leu; and Xaa6 is Tyr or Ala (Formula IIIa)
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 32

Xaa Xaa Ser Asn Xaa Xaa Ser
1               5

<210> SEQ ID NO 33
<211> LENGTH: 7
<212> TYPE: PRT
<213> ORGANISM: Artificial sequence
<220> FEATURE:
<223> OTHER INFORMATION: CDR-L2
<220> FEATURE:
<221> NAME/KEY: MISC_FEATURE
<223> OTHER INFORMATION: Xaa1 is Gly or Ser, Xaa2 is Ala or Thr, Xaa5 is
      Arg or Leu, and Xaa6 is Tyr or Ala
<220> FEATURE:
<221> NAME/KEY: MISC_FEATURE
<223> OTHER INFORMATION: Xaa7 is any suitable residue (such as an Ala
      residue or another flexible residue), Thr, or Ser
<220> FEATURE:
<221> NAME/KEY: MISC_FEATURE
<223> OTHER INFORMATION: Xaa3 is a Ser and Xaa4 is any suitable residue
      other than Asn, Xaa3 is any suitable residue other than Ser and
      Xaa4 is Asn, or Xaa3 is any suitable residue other than Ser and
      Xaa4 is any suitable residue other than Asn (Formula IV)
<220> FEATURE:
<221> NAME/KEY: misc_feature
<222> LOCATION: (1)..(7)
<223> OTHER INFORMATION: Xaa can be any naturally occurring amino acid

<400> SEQUENCE: 33

Xaa Xaa Xaa Xaa Xaa Xaa Xaa
1               5

<210> SEQ ID NO 34
<211> LENGTH: 9
<212> TYPE: PRT
<213> ORGANISM: Artificial sequence
<220> FEATURE:
<223> OTHER INFORMATION: CDR-L3
<220> FEATURE:
<221> NAME/KEY: MISC_FEATURE
<223> OTHER INFORMATION: Xaa1 is Gly or His, Xaa3 is Gly or Tyr, Xaa5 is
      Ser or Arg, Xaa6 is Tyr or Ser, and Xaa8 is Tyr or Pro (Formula Va)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 34

Xaa Gln Xaa His Xaa Xaa Pro Xaa Thr
1               5

<210> SEQ ID NO 35
<211> LENGTH: 9
<212> TYPE: PRT
<213> ORGANISM: Artificial sequence
<220> FEATURE:
<223> OTHER INFORMATION: CDR-L3
<220> FEATURE:
<221> NAME/KEY: MISC_FEATURE
<223> OTHER INFORMATION: Xaa1 is Gly or His, Xaa3 is Gly or Tyr, Xaa5 is
      Ser or Arg, Xaa6 is Tyr or Ser, and Xaa8 is Tyr or Pro
<220> FEATURE:
<221> NAME/KEY: MISC_FEATURE
<223> OTHER INFORMATION: Xaa4 is Tyr, His, or another suitable residue
      (e.g., another cycloalkenyl-associated residue)
<220> FEATURE:
<221> NAME/KEY: MISC_FEATURE
<223> OTHER INFORMATION: Xaa2, Xaa7, and Xaa9 are defined according to
      corresponding positions in Formula V except in for one or more of
      the following: Xaa2 is any suitable residue other than Gln, Xaa7
      is any suitable residue other than Pro, and Xaa9 is any suitable
      residue other than Thr (Formula VI)
<220> FEATURE:
<221> NAME/KEY: misc_feature
<222> LOCATION: (1)..(9)
<223> OTHER INFORMATION: Xaa can be any naturally occurring amino acid

<400> SEQUENCE: 35

Xaa Xaa Xaa Xaa Xaa Xaa Xaa Xaa Xaa
1               5

<210> SEQ ID NO 36
<211> LENGTH: 10
<212> TYPE: PRT
<213> ORGANISM: Artificial sequence
<220> FEATURE:
<223> OTHER INFORMATION: CDR-H1
<220> FEATURE:
<221> NAME/KEY: MISC_FEATURE
<223> OTHER INFORMATION: Xaa4 is any suitable residue other than Glu
      (e.g., Leu), Xaa6 is any suitable residue other than Phe (e.g.,
      Ser), or Xaa4 and Xaa6 represent any suitable residue other than
      Glu and Phe, respectively (Formula VII)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 36

```
Gly Phe Ser Xaa Thr Xaa Tyr Gly Val His
1               5                   10

<210> SEQ ID NO 37
<211> LENGTH: 10
<212> TYPE: PRT
<213> ORGANISM: Artificial sequence
<220> FEATURE:
<223> OTHER INFORMATION: CDR-H1
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid

<400> SEQUENCE: 37

Xaa Xaa Xaa Glu Xaa Phe Xaa Xaa Xaa Xaa
1               5                   10

<210> SEQ ID NO 38
<211> LENGTH: 16
<212> TYPE: PRT
<213> ORGANISM: Artificial sequence
<220> FEATURE:
<223> OTHER INFORMATION: CDR-H2
<220> FEATURE:
<221> NAME/KEY: MISC_FEATURE
<223> OTHER INFORMATION: Xaa7 is any suitable residue other than Asn
      (Formula IX)
<220> FEATURE:
<221> NAME/KEY: misc_feature
<222> LOCATION: (7)..(7)
<223> OTHER INFORMATION: Xaa can be any naturally occurring amino acid

<400> SEQUENCE: 38

Val Ile Trp Ser Gly Gly Xaa Thr Asp Tyr Asn Ala Ala Phe Ile Ser
1               5                   10                  15

<210> SEQ ID NO 39
<211> LENGTH: 16
<212> TYPE: PRT
<213> ORGANISM: Artificial sequence
<220> FEATURE:
<223> OTHER INFORMATION: CDR-H2
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (8)..(16)
<223> OTHER INFORMATION: Xaa can be any naturally occurring amino acid

<400> SEQUENCE: 39

Xaa Xaa Xaa Xaa Xaa Xaa Asn Xaa Xaa Xaa Xaa Xaa Xaa Xaa Xaa Xaa
1               5                   10                  15

<210> SEQ ID NO 40
<211> LENGTH: 13
<212> TYPE: PRT
<213> ORGANISM: Artificial sequence
<220> FEATURE:
<223> OTHER INFORMATION: CDR-H3
<220> FEATURE:
<221> NAME/KEY: MISC_FEATURE
```

```
<223> OTHER INFORMATION: Xaa11 is any suitable residue other than Met
      and Xaa12 is Asp, Xaa11 is Met and Xaa12 is any suitable residue
      other than Asp, or Xaa11 and Xaa12 represent any suitable residues
      other than Met and Asp, respectively (Formula XI)
<220> FEATURE:
<221> NAME/KEY: misc_feature
<222> LOCATION: (11)..(12)
<223> OTHER INFORMATION: Xaa can be any naturally occurring amino acid

<400> SEQUENCE: 40

Asn Pro Arg Pro Gly Asn Tyr Arg Tyr Gly Xaa Xaa Tyr
1               5                   10

<210> SEQ ID NO 41
<211> LENGTH: 13
<212> TYPE: PRT
<213> ORGANISM: Artificial sequence
<220> FEATURE:
<223> OTHER INFORMATION: CDR-H3
<220> FEATURE:
<221> NAME/KEY: misc_feature
<222> LOCATION: (1)..(13)
<223> OTHER INFORMATION: Xaa can be any naturally occurring amino acid

<400> SEQUENCE: 41

Xaa Xaa Xaa Xaa Xaa Xaa Xaa Xaa Xaa Xaa Xaa Xaa Xaa
1               5                   10

<210> SEQ ID NO 42
<211> LENGTH: 10
<212> TYPE: PRT
<213> ORGANISM: Artificial sequence
<220> FEATURE:
<223> OTHER INFORMATION: CDR-H1
<220> FEATURE:
<221> NAME/KEY: MISC_FEATURE
<223> OTHER INFORMATION: Xaa2 is a cycloalkenyl residue, typically an
      aromatic residue, and more typically Phe or Tyr
<220> FEATURE:
<221> NAME/KEY: MISC_FEATURE
<223> OTHER INFORMATION: Xaa3 is selected from Ser, Thr, Ala, Asn, and
      Gln and more typically Ser, Thr, and Ala or even more typically
      Ser or Thr
<220> FEATURE:
<221> NAME/KEY: MISC_FEATURE
<223> OTHER INFORMATION: Xaa6 is Pro or Ser
<220> FEATURE:
<221> NAME/KEY: MISC_FEATURE
<223> OTHER INFORMATION: Xaa8 is Gly or Trp
<220> FEATURE:
<221> NAME/KEY: MISC_FEATURE
<223> OTHER INFORMATION: Xaa9 is selected from Met, Ile, Leu, Val and
      Phe or more typically from Met, Ile, Leu, and Val (Formula XIII)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 42

Gly Xaa Xaa Phe Thr Xaa Tyr Xaa Xaa His
1               5                   10

<210> SEQ ID NO 43
<211> LENGTH: 10
<212> TYPE: PRT
```

```
<213> ORGANISM: Artificial sequence
<220> FEATURE:
<223> OTHER INFORMATION: CDR-H1
<220> FEATURE:
<221> NAME/KEY: MISC_FEATURE
<223> OTHER INFORMATION: Xaa2, Xaa3, Xaa6, Xaa8, and Xaa9 are as defined
      in Formula XIII and Xaa1, Xaa4, Xaa5, Xaa7, and Xaa10 represent
      the same residues as found in the corresponding positions in
      Formula XIII except for one or more of the following: Xaa1 is any
      suitable residue other than Gly; Xaa4 is any suitable residue
      other than Phe; Xaa5 is any suitable residue other than Thr; Xaa7
      is any suitable residue other than Tyr; and Xaa10 is any suitable
      residue other than His (Formula XIV)
<220> FEATURE:
<221> NAME/KEY: misc_feature
<222> LOCATION: (1)..(10)
<223> OTHER INFORMATION: Xaa can be any naturally occurring amino acid

<400> SEQUENCE: 43

Xaa Xaa Xaa Xaa Xaa Xaa Xaa Xaa Xaa Xaa
1               5                   10
```

We claim:

1. A method of treating melanoma in a human subject, comprising administering to the subject
   (a) a KIR2DL1 and KIR2DL2/3 cross-reactive anti-KIR antibody or antibody fragment that binds to KIR2DL1 or KIR2DL2/3 on a natural killer(NK) cell and blocks KIR2DL1- and KIR2DL2/3-mediated inhibition of NK cell cytotoxicity, thereby potentiating NK cell cytotoxicity, wherein the $V_H$ chain of the antibody or antibody fragment comprises the $V_H$ CDRs of a $V_H$ chain having the amino acid sequence set forth in SEQ ID NO: 13 and the $V_L$ chain of the antibody or antibody fragment comprises the $V_L$ CDRs of a $V_L$ chain having the amino acid sequence set forth in SEQ ID NO: 15, and
   (b) human interleukin-2 (IL-2),
thereby treating the melanoma,
   wherein the administration of said anti-KIR antibody or antibody fragment and said IL-2 elicits an NK cell-mediated anti-tumor immune response, and
   further wherein the administered dosage of said anti-KIR antibody or antibody fragment in the absence of said human IL-2 does not elicit a detectable effect on tumor size, wherein the administered dosage of said human IL-2 in the absence of said anti-KIR antibody or antibody fragment does not elicit a statistically significant effect on tumor size, and wherein said administered dosage of said anti-KIR antibody or antibody fragment and said human IL-2 results in a statistically significant reduction of tumor size.

2. The method of claim 1, wherein the method does not include administration of rituximab and/or alemtuzumab to the subject.

3. The method of claim 1, wherein the KIR2DL1 and KIR2DL2/3 cross-reactive anti-KIR antibody or antibody fragment and the IL-2 are the sole pharmaceutically active agents administered to the subject for the treatment.

4. The method of claim 1, wherein the administration of said anti-KIR antibody or antibody fragment and said IL-2 elicits a synergistic effect on NK cell-mediated anti-tumor immunity.

5. The method of claim 1, wherein the melanoma cells are cutaneous melanoma cells, ocular melanoma cells, and/or lymph node-associated melanoma cells.

6. The method of claim 1, wherein the melanoma is metastatic.

7. The method of claim 1, wherein the antibody or antibody fragment comprises a $V_H$ chain having at least 90% sequence identity to the amino acid sequence set forth in SEQ ID NO: 13 and a $V_L$ chain having at least 90% sequence identity to the amino acid sequence set forth in SEQ ID NO: 15.

* * * * *